US010864170B2

(12) United States Patent
Fahmy et al.

(10) Patent No.: US 10,864,170 B2
(45) Date of Patent: Dec. 15, 2020

(54) POLYMERIC BILE ACID NANOCOMPOSITIONS TARGETING THE PANCREAS AND COLON

(71) Applicant: Yale University, New Haven, CT (US)

(72) Inventors: Tarek M. Fahmy, New Haven, CT (US); Jung Seok Lee, New Haven, CT (US); Dongin Kim, Glastonbury, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/757,608

(22) PCT Filed: Sep. 2, 2016

(86) PCT No.: PCT/US2016/050291
§ 371 (c)(1),
(2) Date: Mar. 5, 2018

(87) PCT Pub. No.: WO2017/041053
PCT Pub. Date: Mar. 9, 2017

(65) Prior Publication Data
US 2018/0243226 A1  Aug. 30, 2018

Related U.S. Application Data

(60) Provisional application No. 62/214,648, filed on Sep. 4, 2015.

(51) Int. Cl.
A61K 47/28 (2006.01)
A61K 9/51 (2006.01)
A61K 51/12 (2006.01)
A61P 3/10 (2006.01)
A61K 9/00 (2006.01)
A61K 45/00 (2006.01)
A61K 47/69 (2017.01)
A61P 1/18 (2006.01)
A61P 1/00 (2006.01)
A61P 29/00 (2006.01)
A61K 9/08 (2006.01)
A61K 31/436 (2006.01)
A61K 38/28 (2006.01)
A61K 49/18 (2006.01)

(52) U.S. Cl.
CPC .......... *A61K 9/5146* (2013.01); *A61K 9/0053* (2013.01); *A61K 9/0095* (2013.01); *A61K 9/08* (2013.01); *A61K 9/5153* (2013.01); *A61K 31/436* (2013.01); *A61K 38/28* (2013.01); *A61K 45/00* (2013.01); *A61K 47/6935* (2017.08); *A61K 49/1824* (2013.01); *A61K 51/1244* (2013.01); *A61P 1/00* (2018.01); *A61P 1/18* (2018.01); *A61P 3/10* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 3,266,987 A | 8/1966 | Crowley | |
| 4,460,563 A | 7/1984 | Calanchi | |
| 4,794,000 A | 12/1988 | Ecanow | |
| 5,120,727 A | 6/1992 | Kao | |
| 5,162,333 A | 11/1992 | Failli | |
| 5,202,332 A | 4/1993 | Hughes | |
| 5,385,908 A | 1/1995 | Nelson | |
| 5,484,790 A | 1/1996 | Failli | |
| 5,530,006 A | 6/1996 | Waranis | |
| 5,559,112 A | 9/1996 | Skotnicki | |
| 5,567,709 A | 10/1996 | Skotnicki | |
| 5,780,462 A | 7/1998 | Lee | |
| 5,989,591 A | 11/1999 | Nagi | |
| 6,015,809 A | 1/2000 | Zhu | |
| 6,146,663 A | 11/2000 | Bissery | |
| 6,149,663 A | 11/2000 | Strandberg | |
| 2012/0276095 A1 | 11/2012 | Langermann | |
| 2014/0356384 A1 | 12/2014 | Hubbell | |

FOREIGN PATENT DOCUMENTS

| CA | 2966422 | 5/2016 |
|---|---|---|
| CN | 102351967 | 2/2012 |
| CN | 102351967 B * | 1/2014 |

(Continued)

OTHER PUBLICATIONS

Alexis, Frank, et al. "Factors affecting the clearance and biodistribution of polymeric nanoparticles."Molecular pharmaceutics;5.4 (2008): 505-515. (Year: 2008).*
CA Plus Abstract for CN-102351967-B, Original document published Jan. 2014 (Year: 2014).*
Machine translation of CN-102351967-B, Original document published Jan. 2014 (Year: 2014).*
EUDRAGIT(R) functional polymer webpage at https://healthcare.evonik.com/product/health-care/en/products/pharmaceutical-excipients/EUDRAGIT/, accessed Apr. 15, 2020 (Year: 2020).*
Capurso, et al., "Development of a nanoparticulate formulation of retinoic acid that suppresses Th17 cells and upregulates regulatory T cells", Self/Nonself, 1(4):335-340 (2010).

(Continued)

*Primary Examiner* — Nissa M Westerberg
(74) *Attorney, Agent, or Firm* — Pabst Patent Group LLP

(57) ABSTRACT

Pharmaceutical composition containing poly(bile) acid (PBA) polymers for oral delivery of agent(s) show enhanced uptake by the pancreas, liver, and colon. These nanoparticles show significant retention in the pancreas and colon and are therefore useful for selective delivery. The examples demonstrate efficacy of oral administration of insulin to treat diabetes, and oral induction of tolerance by administration of insulin or ovalbumin in combination with rapamycin. Diabetic animals treated with the insulin or insulin with rapamycin showed normalization of blood glucose levels.

25 Claims, 31 Drawing Sheets

(56) References Cited

FOREIGN PATENT DOCUMENTS

| WO | 9504738 | 2/1995 | | |
|---|---|---|---|---|
| WO | 9516691 | 6/1995 | | |
| WO | 9522972 | 8/1995 | | |
| WO | 2002089820 | 11/2002 | | |
| WO | 2005084637 | 9/2005 | | |
| WO | WO-2006038591 A1 | * | 4/2006 | ......... G01D 5/34792 |
| WO | 2008147482 | 12/2008 | | |
| WO | 2009038591 | 3/2009 | | |

OTHER PUBLICATIONS

Chae, et al., "Deoxycholic acid-conjugated chitosan oligosaccharide nanoparticles for Parkefficient gene carriers", J Control Res,, 109(1-3):330-344 (2005).

Damge, et al., "Poly(alkly cyanoacrylate) nanospheres for oral administration of insulin", Journal of Pharmaceutical Sciences, 86(12):1403-1409 (1997).

Elbarbry, et al., "Liquid chromatographic determination of mycophenolic acid and its metabolites in human kidney transplant plasma: pharmacokinetic application", J Chromatogr B Analyt Technol Biomed Life Sci, 859(2): 276-81 (2007).

Ginzler, et al., "Mycophenolate mofetil or intravenous cyclophosphamide for lupus nephritis", N Engl J Med, 353(21):2219-28 (2005).

Hoffman, et al., "Bile acid solubility and precipitation in vitro and in vivo: the role of conjugation, pH, and Ca2+ ions", J. Lipid Res., 33:617-26 (1992).

Jonsson, et al., "Inosine monophosphate dehydrogenase (IMPDH) inhibition in vitro suppresses lymphocyte proliferation and the production of immunoglobulins, autoantibodies and cytokines in splenocytes from MRLIpr/Ipr mice.", Clin Exp Immunol, 124(3): 486-91 (2001).

Jonsson, et al., Mycophenolic acid inhibits inosine 5'-monophosphate dehydrogenase and suppresses immunoglobulin and cytokine production of B cells Int Immunopharmacol, 3(1):31-7 (2003).

Karnell, et al., Mycophenolic acid differentially impacts B cell function depending on the stage of differentiation J Immunol, 187(7): 3603-12 (2011).

Kossena, et al., "Separation and characterization of the colloidal phases produced on digestion of common formulation lipids and assessment of their impact on the apparent solubility of selected poorly water soluble drugs", J. Pharm. Sci., 92:634-8 (2002).

Lagaraine, et al., Mycophenolic acid-treated human dendritic cells have a mature migratory phenotype and inhibit allogeneic responses via direct and indirect pathways Int Immunol, 17(4):351-63 (2005).

Lagaraine, et al., "Induction of human CD4+ regulatory T cells by mycophenolic acid treated dendritic cells", J Leukoc Biol, 84(4):1057-64 (2008).

Lipsky, "Mycophenolate mofetil.", Lancet, 348:L1357-1359 (1996).

Mehling, et al., "Induction of human CD4+ regulatory T cells by mycophenolic acid-treated dendritic cells", J Immunol, 165(5):2374-81 (2000).

Mishra, et al., "Efficient hepatic delivery of drugs: novel strategies and their significance", BioMed Res Intl, vol. 2013, Article ID 382184, 20 pages (2013).

Opal and Depalo, Anti-inflammatory cytokines Chest, 117(4):1162-72 (2000).

Park, et al., "Heparin-deoxycholic acid chemical conjugate as an anticancer drug carriers and its antitumor acstivity", J Cont Rel., 114(3):300-6 (2006).

Quemeneur, et al., "Mycophenolic Acid Inhibits IL-2-Dependent T Cell Proliferation, But Not IL-2-Dependent Survival and Sensitization to Apoptosis", J Immunol, 169(5):2747-55 (2002).

Ring, et al., "Targeting of Autoantigens to DEC205+ Dendritic Cells In Vivo Suppresses Experimental Allergic Encephalomyelitis in Mice", J. Immuno., 191 (6) 2938-47 (2013).

Ruoslahti, et al., "Specialization of tumour vasculature", Nat. Rev. Cancer, 2:83-90 (2002).

Samstein, et al., "The use of deoxycholic acid to enhance the oral bioavailability of biodegradable nanoparticles", Biomaterials, 29:703-8 (2008).

Silva-Sánchez, "ESAT-6 Targeting to DEC205+ Antigen Presenting Cells Induces Specific-T Cell Responses against ESAT-6 and Reduces Pulmonary Infection with Virulent *Mycobacterium tuberculosis*", PLoS ONE 10(4): e0124828.

Sjoestrom, et al., "Structures of nanoparticles prepared from oil-in-water emulstons", Pharmaceuts Res., 12(1):39-48 (1995).

Spiering, et al., "DEC205+ Dendritic Cell-Targeted Tolerogenic Vaccination Promotes Immune Tolerance in Experimental Autoimmune Arthritis", J Immunol., 194(10):4804-13 (2015).

Tosi, et al., "Nanoparticles as Blood-Brain Barrier Permeable CNS Targeted Drug Delivery Systems", SfN Neurosci San Diego (USA), 1:84 (2010).

Wadia, et al., "Nanoparticles as Blood-Brain Barrier Permeable CNS Targeted Drug Delivery Systems", Hum Immunol, 70(9):692-700 (2009).

International Search Report for PCT/US2007/081305 dated Jul. 21, 2007.

International Search Reoport for PCT/US2016/050291 dated Nov. 25, 2016.

* cited by examiner

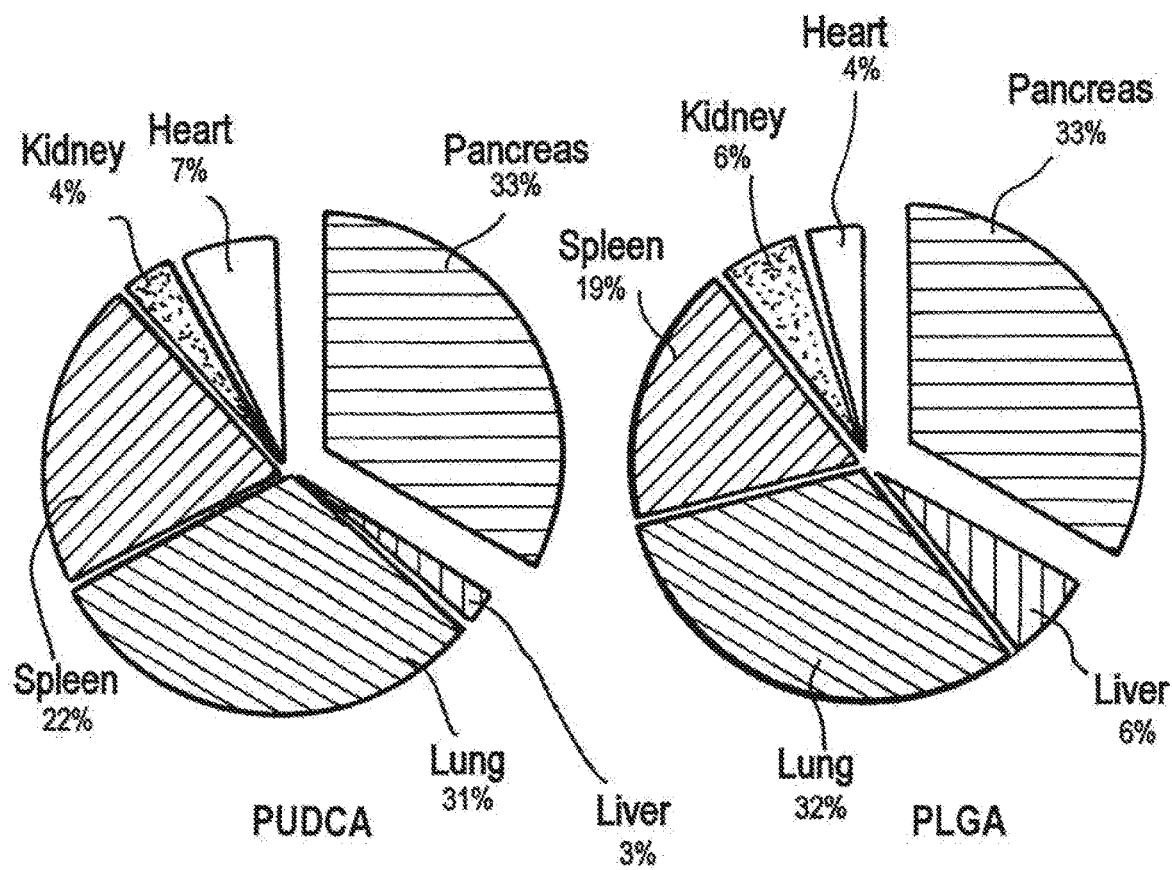
FIG. 5E
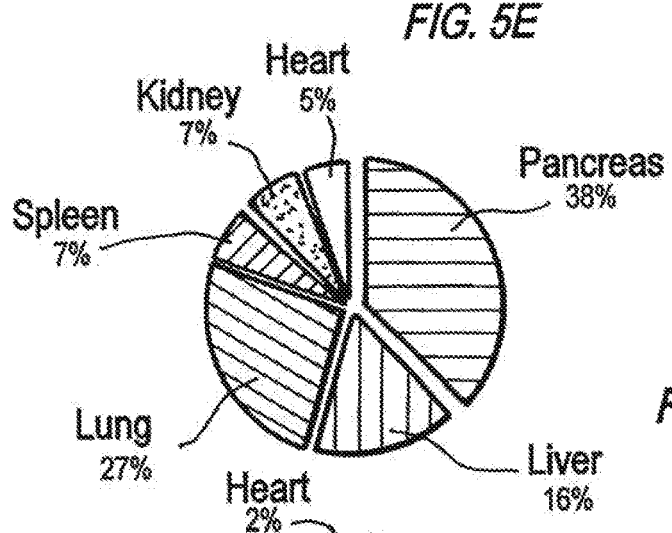
FIG. 5F
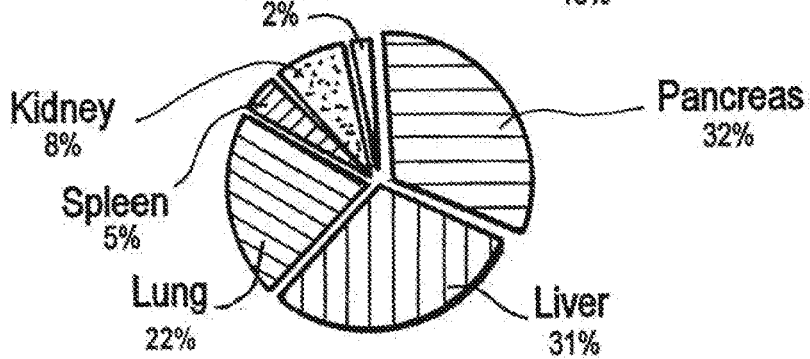

POLYMERIC BILE ACID NANOCOMPOSITIONS TARGETING THE PANCREAS AND COLON

CROSS REFERENCE TO RELATED APPLICATIONS

This application claims priority to U.S. Ser. No. 62/214,648 entitled "Polymeric Bile Acid Nanocompositions Targeting the Pancreas and Colon" filed Sep. 4, 2015 by Tarek Fahmy, Jung Seok Lee, and Dongin Kim.

STATEMENT REGARDING FEDERALLY SPONSORED RESEARCH OR DEVELOPMENT

This invention was made with Government Support under Agreement 0747577 awarded to Tarek Fahmey by National Science Foundation and under AI056363 awarded by the National Institutes of Health. The Government has certain rights in the invention.

FIELD OF THE INVENTION

The invention is generally directed to polymeric bile acid nanocompositions which are orally administered for targeted delivery of agent to the pancreas, liver, and colon.

BACKGROUND OF THE INVENTION

Oral delivery of peptides and drugs is one of the greatest challenges for drug delivery due to the many obstacles present in the gastrointestinal tract. These obstacles include: (1) the acidity and presence of digestive enzymes in the stomach, which are optimized to degrade many molecules; (2) the low absorption of therapeutics from the intestinal lumen due to the tight junctions in the epithelial lining; (3) the deactivation or extrusion of many drugs in the epithelial lining; and (4) the exposure of the intestinal lining to toxic levels of the drug resulting in dose-limiting side effects (Samstein et al., *Biomaterials*, 29:703-708 (2008)). These barriers significantly decrease the bioavailability of drugs and peptides administered orally while simultaneously limiting the maximum tolerable dosage, thereby compelling intravenous administration of therapeutics. However, oral delivery remains the most attractive drug delivery route due to its ease and convenience, resulting in improvements in quality of life for patients and reduced administrative costs.

An objective in designing a drug delivery system for oral administration is to maintain drug levels in the therapeutic range for sustained periods of time. The delivery system must protect the drug at low pH, facilitate absorption in the intestinal tract, bypass unwanted metabolic degradation, and limit intestinal cell exposure. Particulate systems for oral delivery have been attempted to address some of these issues. They can theoretically provide protection from degradation and metabolic deactivation, as well as limit intestinal exposure. Nanoparticles of synthetic poly-esters such as poly(lactic acid), poly(glycolic acid), and their copolymers poly(lactide-co-glycolide) (PLGA) are often chosen due to their biocompatibility and versatility in encapsulating a variety of drugs and biologics, as well as the ability to tune the dynamics of drug release by varying monomer ratios and polymer molecular weight. Oral delivery of PLGA particles and uptake by intestinal cells has also been well studied.

However, absorption efficiency of particulates is typically very low, with estimates of only 1% absorbed after oral administration. In addition, PLGA particles are degraded via acid-catalyzed ester hydrolysis and therefore release much of their contents at the low pH of the stomach.

Targeted delivery of active agents and/or imaging agents to internal organs following oral administration remains a challenge as harsh biochemical environment, inherent to the stomach, specifically the highly acidic pH and the presence of proteolytic enzymes, degrades and inactivates many therapeutic agents. There remains a need for improved oral delivery systems that increase the bioavailability of orally delivered drugs to target organs, preferably ones which are formed of materials that are generally regarded as safe and do not require expensive manufacturing, and which are broadly applicable for delivery without the use of targeting agents.

Therefore, it is an object of the present invention to provide a highly efficient oral delivery system that delivers active agents and/or imaging agents to internal organs, especially the pancreas and colon, without the use of targeting agents.

It is a further object of the present invention to provide methods of making the highly efficient oral delivery systems.

It is yet another object of the present invention to provide methods of using the highly efficient oral delivery systems.

It is a further object of the present invention to provide formulations for selective uptake to organs such as the liver and spleen.

It is another object of the present invention to provide formulations for inducing tolerance, especially formulations which can be administered orally, and even more so formulations which then show selective uptake to the liver and spleen.

SUMMARY OF THE INVENTION

Pharmaceutical composition containing nanoparticles of poly(bile) acid (PBA) polymer, and methods of making and using thereof, are described herein. The PBA nanoparticles are typically formed from polymeric bile acid chains and do not include other polymers or blends of polymers. The PBA nanoparticles may encapsulate one or more agent(s). The pharmaceutical compositions may contain excipients, including, but not limited to, emulsifiers, surfactants, suspending agents, antioxidants, chelating agents, humectants, and preservatives.

Typically, the PBA nanoparticles are formed of PBA polymers with molecular weight ranging between 500 Da and 50,000 Da. The size of the nanoparticles ranges from between 1 and 1000 nm, preferably from between 60 and 600 nm, more preferably between 100 and 400 nm.

The PBA nanoparticles do not have to include targeting agents (moieties) because they preferentially localize to pancreas, liver, or colon, in the absence of targeting moieties, after oral administration. Therefore, the PBA nanoparticles are selectively taken up by target tissues, such as the pancreas, liver, or colon, without the need for targeting moieties to these tissues. It may be desirable to include targeting moieties, however, to target to specific cells types such as dendritic cells, which are present in the tissues demonstrating selective or enhanced uptake. For example, in the case where the nanoparticles are used to induce tolerance, the PBA nanoparticles include an agent such as rapamycin and antigen to which tolerance is to be induced, and the PBA nanoparticle has bound thereto a targeting molecule specific to dendritic cells.

Generally, the nanoparticles encapsulate one or more therapeutic, prophylactic, diagnostic, and/or imaging agents.

The formulation provides a means to orally deliver many agents that are normally administerable only by injection. In some embodiments, the agent is a therapeutic agent for treatment of Type 1 Diabetes (T1D), Type 2 Diabetes (T2D). In other embodiments, the agent is a therapeutic agent for suppressing or resolving inflammation in the pancreas, liver, or colon, such as in inflammatory bowel disease (IBD). In yet other embodiments, the agent is a therapeutic for suppressing or treating neoplasms of the pancreas, liver, or colon. In another embodiment, the agent is an immunomodulatory, such as rapamycin, TGF-beta, rapamycin (analogs include everolimus, ridaforolimus, remsirolimus, umirolimus, zotarolimus), retinoic acid, TLR agonists, cyclosporin, methotrexate, a steroid, azathioprine, and tacrolimus to induce tolerance or an adjuvant such as Cpg to cause immunostimulation, in combination with an antigen. Any combination of therapeutic agent(s) may be encapsulated, optionally in combination with an imaging agent.

Following oral administration of the pharmaceutical composition, untargeted PBA nanoparticles are typically more efficient at delivering agents to target tissues, than are the untargeted nanoparticles formed of poly(lactic-co-glycolic) acid (PLGA). For example, the orally delivered PBA nanoparticles can deliver at least two times greater amount of one or more agent(s) to pancreas, liver, or colon, when compared to the amount of the same agent(s) delivered to these organs by the same number of orally delivered untargeted PLGA nanoparticles encapsulating the same amount of the agent(s). The PBA nanoparticles increase bioavailability of orally delivered drugs in the pancreas, liver, and colon, when compared to the bioavailability of the same drugs delivered orally at the same dose in free form, or encapsulated in PLGA nanoparticles.

Generally, the PBA nanoparticles targeting pancreas, liver, or colon, after oral administration, are formulated to deliver an effective amount of the agent to the pancreas, liver, or colon to alleviate one or more symptoms of a disease or disorder. In some embodiments, the PBA nanoparticles targeting pancreas, liver, or colon, deliver between 0.1 ng to 200 µg agent/NP of the agent to the target tissue, so that the total dosage is dependent upon the administered volume of NPs. The PBA nanoparticles can release the agents over time, by sustained release, or through a singular burst release. For example, the one or more agent(s) encapsulated in the PBA nanoparticles can be released over a period of time ranging from between one hour and a few weeks, or can be released within the first 24 hours of reaching the target organ.

Methods of making NPs using self-assembly and aggregation of bile acid have been developed. Two methods for making the bile acid assemblies include fabrication of branched polymeric bile acid units (as opposed to linear chains), and encapsulation through guest/host interactions in cavities that form with such branched building blocks; and supramolecular self-assembly via fluorinated bile acid units. Fluorination introduces a "fluorophobic effect". This is distinctly different from hydrophobic or hydrophilic interactions, and results in self-assembly into a complex larger structure without the need for special formulation.

A method of preventing, suppressing or treating one or more symptoms of a disorder, disease or condition may include administering to a subject in need thereof an oral dosage unit of the pharmaceutical composition containing the PBA nanoparticles encapsulating the one or more agent (s). These may be delivered to target tissue, such as pancreas, liver, or colon, or cells such as dendritic cells; wherein the one or more agent(s) are released. In preferred embodiments, the methods are directed to preventing, suppressing or treating symptoms of type 1 or type 2 diabetes ("T1D", "T2D"), irritable bowel disease ("IBD"), pancreatitis, hepatitis, colitis, and neoplasms of the pancreas, liver, or colon.

The formulations may also be used as oral vaccines to a protein, small molecule, sugar, nucleic acid or combination there, or to induce tolerance to one or more antigens such as autoimmune antigens (for example, diabetes, lupus, myasthenia gravis, multiple sclerosis, psoriasis, gout), allergenic antigens (for example, food, insect, drug).

Examples demonstrate effective oral drug delivery of proteins such as insulin. Soluble insulin given orally (same frequency and route) had very little effect. Insulin administered in polylactide-co-glycolide particles ("PLGA") has no effect. Insulin in PUDCA is the only group in which the sugar level remains below the diabetic line for the 21 days (i.e., curative). Blank PUDCA (no insulin) causes an initial decrease in blood glucose but it then rises. This is in part because the bile acid has inherent immunosuppressive, anti-inflammatory effects.

The examples show treatment or cure of Type I diabetes. FIGS. 5d and 5e show oral administration of Bile acid particles (Polyursodeoxycholic acid) ("PUDCA"), loaded with the antigen (insulin). The particles are administered orally 7 times (once a day for a week) in animals with diabetes and the blood glucose level is monitored over 21 days. In the control saline group (PBS), the blood glucose level increases back to above 250 mg/dl i.e diabetic range. FIG. 5e establishes survival of the diabetic mice. FIG. 5 g-J, establish the mechanism of action on cytotoxic cells (FIG. 5g), regulatory cells (5h), IFN release from cells stimulated after animals are euthanized (5j), and antigen-specific IFN release from cells that that have been treated with PUDCA and OValbumin as antigen. FIG. 5 J shows induction of tolerance.

In summary, the examples demonstrate induction of tolerance two different antigens (insulin) (FIG. 5 d-h) and with Ovalbumin (FIG. 5j). FIG. 4 shows the immunsuppressive effect of PUDCA loaded with rapamycin in Cyclophosmamide induced diabetes.

In other embodiments, the methods of using the pharmaceutical compositions may include methods of non-invasively imaging the target organ as a whole, or distinct microenvironments within the target organ, such as pockets of inflammation, leaky vasculature, or neoplasms, alone or in combination with therapy.

BRIEF DESCRIPTION OF THE DRAWINGS

FIG. 5E is a pie chart showing the percent biodistribution of DiR-loaded PLGA and PUDCA nanoparticles four hours after their oral administration. Although the biodistribution is unchanged between the two polymeric particles, data in FIGS. 4C and 5A demonstrate that PUDCA nanoparticles deliver at least 3.5 times greater amount of dye to the pancreas than do PLGA nanoparticles. FIG. 5F is a pie chart showing biodistribution of NP by percentage of total detected fluorescence.

DETAILED DESCRIPTION OF THE INVENTION

I. Definitions

Figure 1:
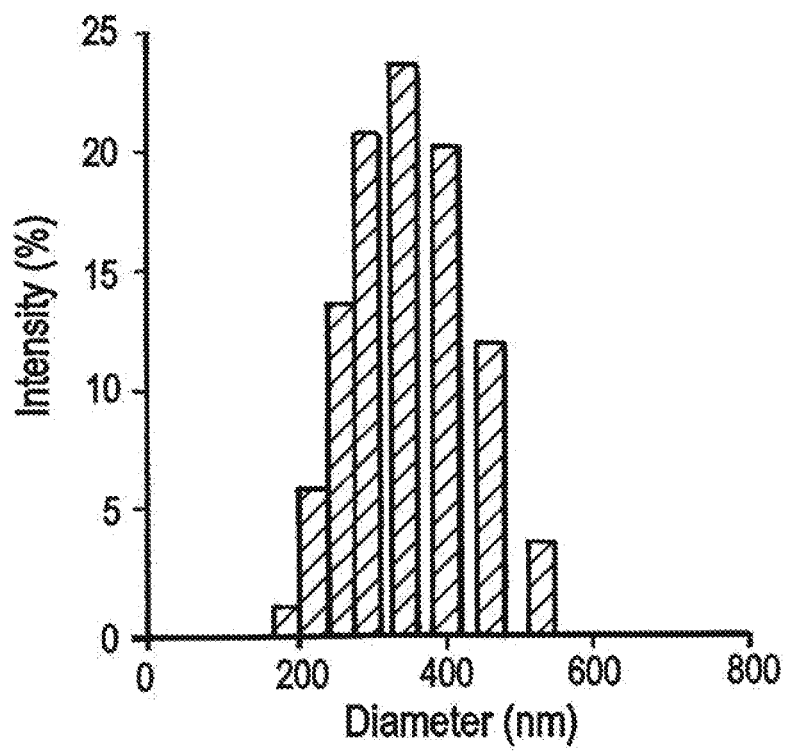
FIG. 1 is a histogram showing size distribution of poly (bile) acid (PBA) nanoparticles as intensity (%) versus diameter (nm).

As used herein, the term "nanoparticle" generally refers to a particle having a diameter from about 10 nm up to, but not including, about 1000 nm, preferably from about 60 nm to about 450 nm. The particles can have any shape. Typically, the nanoparticles are spherical and the size is presented as diameter measured in nm.

As used herein, the term "encapsulated" refers to the agent, for example, a therapeutic and/or an imaging agent, encapsulated within, surrounded by, and/or dispersed throughout a polymeric matrix of the nanoparticle. Alternatively or additionally, the agent can be associated with a polymeric matrix by hydrophobic interactions, charge interactions, van der Waals forces, etc.

As used herein, the term "untargeted" refers to nanoparticles formed of a polymer, such as PBA or PLGA, without additional elements, such as targeting moieties, having an increased affinity to a particular cell type or organ.

As used herein, the term "targeting moiety" refers to any molecule such as an antibody, ligand, receptor binding moiety, or an active fragment thereof, or an agonist, antagonist, or tissue- or cell-specific targeting molecule, that is used to attach the nanoparticle to a cell in the target organ.

As used herein, the term "active agent" or "biologically active agent" are used interchangeably herein to refer to a chemical or biological compound that induces a desired pharmacological and/or physiological effect, wherein the effect may be prophylactic, therapeutic and/or diagnostic. The terms also encompass pharmaceutically acceptable, pharmacologically active derivatives of active agents, including, but not limited to, salts, esters, amides, prodrugs, active metabolites, and analogs.

As used herein, the term "excipient", or "pharmaceutically acceptable excipient", refers to a pharmacologically inactive substance added to the composition to further facilitate administration of the composition.

As used herein, "oral administration" refers to delivery of the disclosed composition to a subject via an oral route. Oral administration can be achieved via oral gavage, or by swallowing of the composition in liquid or solid form. The liquid forms of orally administered compositions can be in a form of a solution, capsule or a gel. Solid forms of orally administered compositions include capsules, tablets, pills, powders, and granules.

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a microbial infection may refer to inhibiting survival, growth, and/or spread of the microbe. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, "tolerance" means the inability of the immune system to mount an adaptive (T or B-mediated) response to a given antigen.

As used here, "tolerogenic" means the condition or capability of stimulating or increasing tolerance.

As used herein "Treg" includes any T cell that confers suppression. Thus the term encompasses traditional CD4, Foxp3+ Tregs, as well as other CD4 cells that do not express Foxp3 but can be regulatory by secreting IL-10 (Tr1 cells) among other signals, and CD8 Tregs (Foxp3+ and −) which have also been identified.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

II. Compositions

The compositions described herein include nanoparticles formed of poly(bile) acid polymers, having therapeutic, prophylactic and/or diagnostic agents incorporated therein or thereon, and, optionally, pharmaceutically acceptable excipients.

A. Polymers

Generally, the monomers of bile acids suitable for forming poly(bile) acid polymers, are defined by Formula I:

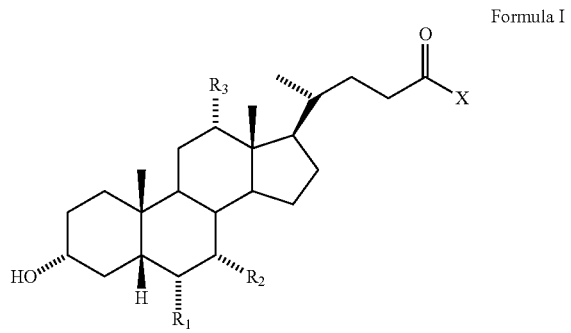

Formula I wherein:
$R_1$, $R_2$, and $R_3$ are independently hydrogen or hydroxyl group, and
X is a hydroxyl group at low pH (2-5) that is deprotonated at pH above 5.5.

The fully protonated hydroxyl group at position X renders the monomers insoluble in water, and the loss of the proton improves the water solubility of the monomers.

The structure of bile acid monomer cholic acid (CA) is shown in Formula II:

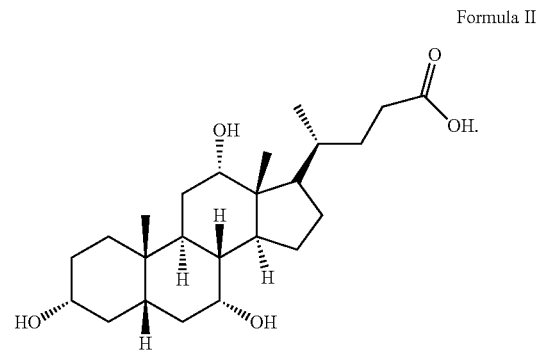

Formula II.

The structure of bile acid monomer lithocholic acid (LCA) is shown in Formula III:

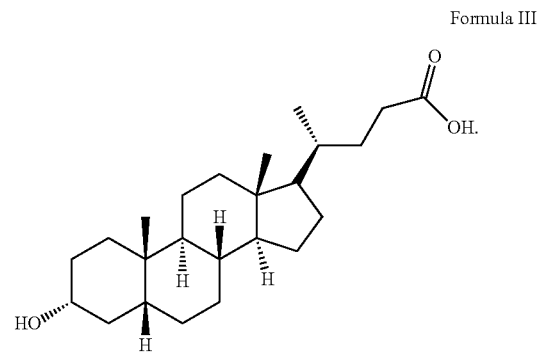

The structure of bile acid monomer deoxycholic acid (DCA) is shown in Formula IV:

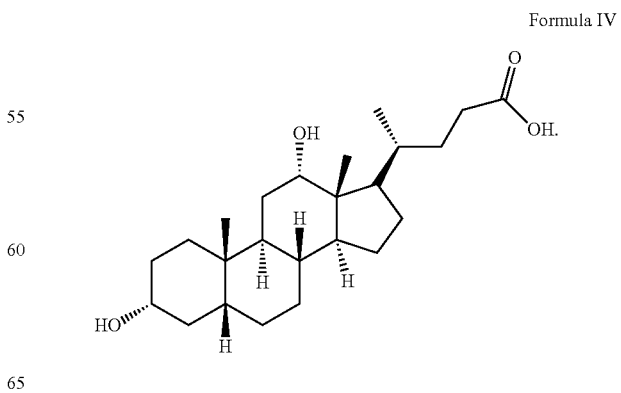

The structure of bile acid monomer cheno-deoxycholic acid (CDCA) is shown in Formula V:

Formula V

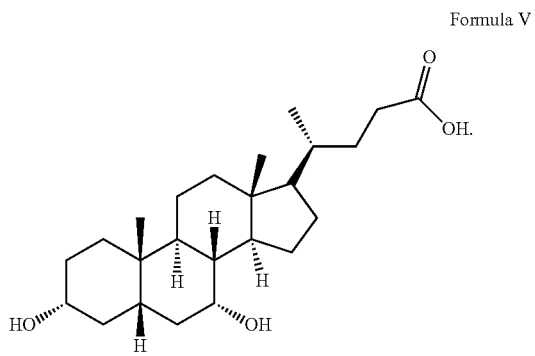

The structure of bile acid monomer urso-deoxycholic acid (UDCA) is shown in Formula VI:

Formula VI

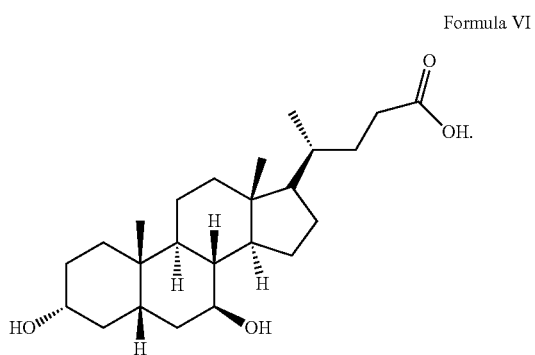

Other suitable bile acids include, but are not limited to, glycocholic acid, taurocholic acid, glycodeoxycholic acid, taurodeoxycholic acid, lithocholic acid, taurolitholic acid, taurochenodeoxycholic acid, tauroursodeoxycholic acid, glycolithocholic acid, glycochenodeoxycholic acid, and taurine conjugates of 3-alpha-7-alpha-12-alpha-22-xi-tetrahydroxy-5-beta-cholestan-26-oic acid (tetrahydroxystero-cholanic acid) and 3-alpha-12 alpha-22 xi-trihydroxy-5-beta-cholestan-26-oic acid.

The above-listed monomers are esterified to produce the poly(bile) acid (PBA) polymers having a molecular weight between 500 and 50,000 Daltons. Room temperature polymerization of bile acids can be carried out using a mixture of diisopropyl carbodiimide (DIC), and a 1:1 salt of dimethyl amino pyridine and p-toluenesulfonic acid (DMAP/PTSA) in mild reaction conditions and without significant cross-linking. Carboiimide activation leads to preferential esterification at carbon 3 and linear polymeric chains. Applied to UDCA, the polymerized UDCA can be defined by Formula VII:

Formula VII

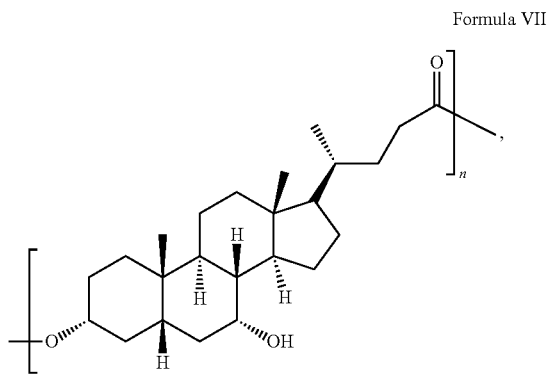

wherein n is a number ranging from between 2-600, corresponding to a polymer Mw average in the range 1000-240, 000.

The degree of branching can vary from a generation 0 (no branches) to higher unlimited number of generations.

The polymers may be formed from the same monomer, such as UDCA, forming poly(UDCA), or PUDCA. In other embodiments, the polymers may be formed from a mix of bile acid polymers, forming copolymers or monomers coating a polymer bile acid cores. In these embodiments, the monomers or polymers may be mixed in any combination, and at any ratio, to form polymeric blends of bile acid polymers ranging in molecular weight from between 800 and 250 000 Dalton. Typically, the polymers are linear, but other structures to the polymeric chains, such as branched, or forked, or dendrimeric could be used. A dendrimer of poly bile acids (dendritic PUDCA, for example), will have pH stimuli response similar to the linear chain counterparts. This dendritic system will be in a swollen or open state at physiological pH or pH above 6.0. Therefore, it can be easily loaded with drug through non-covalent association with the dendritic polymer or by entrapment in the interstitial cavities formed in the branched system. Low pH will shrink the system, protecting the encapsulant and/or releasing it slowly. As such, a dendritic bile acid polymer may serve as a nanoparticle itself, without the formulation conditions used with linear polymers.

In some embodiments, the monomers, or the formed polymeric chains, may include moieties with one or more radionuclides, or optical (bioluminescent, chemiluminscent, fluorescent or other high extinction coefficient or high quantum yield optical tracers. Similarly, non-invasive contrast agents such as T1 MR agents in the class of heavy metals (gadolinium, dysprosium etc.) or T2 contrast agents (iron oxide, manganese oxide, etc.), iodinated agents for X-ray attenuation (CT) and other modalities. The inherent ability of these systems to respond to changes in the pH range of 7 to 2 has significant implications for delivery of therapeutics both to low pH endocytic compartments within cells and/or sites of inflammation characterized by low pH microenviroment or the surrounding environment of tumors. The polymeric chains of these embodiments can be used to form traceable PBA nanoparticles, eliminating the need of encapsulating imaging/tracing agents, and enhancing the imaging modalities due to local retention of the imaging agent (confinement of the probe) in the area.

The water solubility of bile acids rises exponentially with increasing pH (Hoffman et al., J. Lipid Res., 33:617-626 (1992)). The polymeric chains of PBA and nanoparticles made therefrom also aggregate at low pH and become increasingly soluble/dispersed as the pH increases above 5.5. These polymers and nanoparticles are particularly suited for oral drug delivery, as they can protect the agent(s) encapsulated with the nanoparticles from the destructive environment of the stomach. The agent(s)s can then be safely released at the neutral pH in the intestines and target organs, as the polymers begin to dissolve releasing the agent(s).

The nanoparticles can have a mean geometric diameter that is less than 600 nm, but greater than 10 nm, more preferably between 60 and 450 nm, or greater than 50 nm but less than 500 nm. In some embodiments, the mean geometric diameter of a population of nanoparticles is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75 and 250 nm. In some embodiments, 30%, 40%, 50%, 60%, 70%, 80%, 90%, or more of the nanoparticles of a population of nanoparticles have a diameter that is between 50 and 500 nm.

Exemplary structural properties and loading capacity of the nanoparticles are presented in Table 1 in Example 1, below.

The PBA nanoparticles are pH responsive. The polymer backbone shrinks, and the nanoparticles aggregate, in a low pH microenvironment (pH 2-5), and expands at higher pH (pH 6-7.5) to release an encapsulated agent. The PBA polymer allows for encapsulation of both hydrophilic and hydrophobic drugs, peptides, proteins, oligonucleotides. The encapsulated agents are released over time in the higher pH microenvironment of the gut lumen, or generally in organs with pH above 5.5-6.0.

B. Therapeutic, Prophylactic and Diagnostic Agents to be Encapsulated.

The PBA nanoparticles may encapsulate one or more therapeutic, nutritional, diagnostic, and prophylactic compounds. These may be proteins, peptides, carbohydrates, polysaccharides, nucleic acid molecules, organic molecules, and low molecular weight inorganic compounds.

Therapeutic and prophylactic agents include antibiotics, antivirals, anti-parasitics (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, and taxol) and anti-proliferatives, antibodies and bioactive fragments thereof (including humanized, single chain, and chimeric antibodies), antigen and vaccine formulations, hormones and other peptide drugs, cytokines, immunomodulatory agents (suppressive or stimulatory), and anti-inflammatories. Small molecules having a molecular weight of 2000 Daltons or less include anti-inflammatory agents such as steroids, including methyl prednisone, dexamethasone, non-steroidal anti-inflammatory agents such as COX-2 inhibitors, steroidal anti-inflammatory agents, gold compound anti-inflammatory agents, anti-angiogenic agents, salicylate anti-inflammatory agents, ranibizumab, minocycline, anti-VEGF agents, including aflibercept, and rapamycin.

The formulations can also be used to administer proteins such as insulin and insulin analogus, as well as other small proteins, unlike many other delivery systems. As demonstrated by the examples, insulin can be effectively delivered orally to normalize blood glucose levels in diabetic animals.

Exemplary diagnostic materials include paramagnetic molecules, fluorescent compounds, magnetic molecules, and radionuclides.

C. Tolerogenic Compositions

Compositions for delivering tolerogenic (tolerizing) antigen, an immunosuppressant (e.g., rapamycin), or preferably the combination thereof, to dendritic cells or antigen presenting cells (APCs) in the liver are provided. In some embodiments, the tolerogenic antigen and the immunosuppressant are co-delivered, more preferably co-loaded into the same particle for simultaneous co-delivery, to the same cell. APCs can then became tolerogenic and migrate to peripheral lymphoid lymph nodes where it is believed they activate, induce proliferation, induce differentiation, or combination thereof of Tregs such as CD4+Foxp3+ cells. These Tregs can then suppress activation and antibody production by B cells specific for the tolerogenic antigen. It is desirable that the antigen and immunosuppressive drug be spatially localized to the same liver dendritic cell or liver endothelial cell for initiation of the tolergenic program. Therefore, in the most preferred embodiments, the antigen and immunosuppressive drug are loaded into, dispersed within, conjugated to, or otherwise displayed on or in same particle. Co-delivery of immunosuppressant with antigen in the same particle can have two effects: 1) concentrating the antigen and drug dose in the same cell, and 2) ensuring that the same antigen-presenting cells are suppressed. This strategy can reduce or prevent broad immunosuppression or antigen-specific immunogenicity.

Immunosuppressant is delivered with the antigen to the same antigen presenting cell to improve the immunosuppressive effect (e.g., tolerance induction) of the drugs. In some embodiments, two immunosuppressants are co-delivered, such as mycophenolic acid and rapamycin. Preferably the particle accumulates in the liver. In some embodiments, the particle includes a targeting moiety, for example a targeting moiety that increases (or further increases) the accumulation of the particle in the liver or directs the particles to specific cells, such as dendritic cells in the liver.

In alternative embodiments, the antigen and the immunosuppressive drug are loaded into, dispersed within, conjugated to, or otherwise displayed on or in separate particles.

A. Antigens

The particles can include one or more antigens, preferably a tolerogenic antigen. A suitable antigen is selected based on the desired therapeutic outcome and the disease, disorder, or condition being treated. Exemplary antigens are known in the art. See, for example, U.S. Published Application No. 2014/0356384 which discusses:

The tolerogenic antigen can be derived from a therapeutic agent protein to which tolerance is desired. Examples are protein drugs in their wild type, e.g., human factor VIII or factor IX, to which patients did not establish central tolerance because they were deficient in those proteins; or nonhuman protein drugs, used in a human. Other examples are protein drugs that are glycosylated in nonhuman forms due to production, or engineered protein drugs, e.g., having non-native sequences that can provoke an unwanted immune response. Examples of tolerogenic antigens that are engineered therapeutic proteins not naturally found in humans include human proteins with engineered mutations, e.g., mutations to improve pharmacological characteristics. Examples of tolerogenic antigens that comprise nonhuman glycosylation include proteins produced in yeast or insect cells.

The tolerogenic antigen can be derived from proteins that are administered to humans that are deficient in the protein. Deficient means that the patient receiving the protein does not naturally produce enough of the protein. Moreover, the proteins may be proteins for which a patient is genetically deficient. Such proteins include, for example, antithrombin-III, protein C, factor VIII, factor IX, growth hormone, somatotropin, insulin, pramlintide acetate, mecasermin (IGF-1), β-gluco cerebrosidase, alglucosidase-α, laronidase (α-L-iduronidase), idursuphase (iduronate-2-sulphatase), galsulphase, agalsidase-β (α-galactosidase), α-1 proteinase inhibitor, and albumin.

The tolerogenic antigen can be derived from therapeutic antibodies and antibody-like molecules, including antibody fragments and fusion proteins with antibodies and antibody fragments. These include nonhuman (such as mouse) antibodies, chimeric antibodies, and humanized antibodies. Immune responses to even humanized antibodies have been observed in humans (Getts D R, Getts M T, McCarthy D P, Chastain E M L, & Miller S D (2010), mAbs, 2(6):682-694.). Accordingly, embodiments include a fusion molecule for tolerogenesis comprising an erythrocyte-binding moiety and at least one antigen, antigenic fragment, or antigenic mimotope of one or more of these proteins, with the erythrocyte-binding moiety specifically binding, for instance, glycophorin A or a target chosen from the group consisting of Band 3, glycophorin B, glycophorin C or other members of the Erythrocyte Target Group. The erythrocyte-binding moiety may be, for instance, chosen from the group consisting of antibodies, antibody fragments, scFvs, peptide ligands and aptamers.

The tolerogenic antigen can be derived from proteins that are nonhuman. Examples of such proteins include adenosine deaminase, pancreatic lipase, pancreatic amylase, lactase, botulinum toxin type A, botulinum toxin type B, collagenase, hyaluronidase, papain, L-Asparaginase, rasburicase, lepirudin, streptokinase, anistreplase (anisoylated plasminogen streptokinase activator complex), antithymocyte globulin, crotalidae polyvalent immune Fab, digoxin immune serum Fab, L-arginase, and L-methionase.

The tolerogenic antigen can be derived from human allograft transplantation antigens. Examples of these antigens are the subunits of the various MHC class I and MHC class II haplotype proteins, and single-amino-acid polymorphisms on minor blood group antigens including RhCE, Kell, Kidd, Duffy and Ss.

The tolerogenic antigen can be a self-antigen against which a patient has developed an autoimmune response or may develop an autoimmune response. Examples are proinsulin (diabetes), collagens (rheumatoid arthritis), myelin basic protein (multiple sclerosis).

For example, Type 1 diabetes mellitus (T1D) is an autoimmune disease whereby T cells that recognize islet proteins have broken free of immune regulation and signal the immune system to destroy pancreatic tissue. Numerous protein antigens that are targets of such diabetogenic T cells have been discovered, including insulin, GAD65, chromogranin-A, among others. In the treatment or prevention of T1D, it would be useful to induce antigen-specific immune tolerance towards defined diabetogenic antigens to functionally inactivate or delete the diabetogenic T cell clones.

Tolerance and/or delay of onset or progression of autoimmune diseases may be achieved for various of the many proteins that are human autoimmune proteins, a term referring to various autoimmune diseases wherein the protein or proteins causing the disease are known or can be established by routine testing.

The tolerogenic antigen can be one or more of the following proteins, or a fragment or peptide derived therefrom. In type 1 diabetes mellitus, several main antigens have been identified: insulin, proinsulin, preproinsulin, glutamic acid decarboxylase-65 (GAD-65), GAD-67, insulinoma-associated protein 2 (IA-2), and insulinoma-associated protein 2β (IA-213); other antigens include ICA69, ICA12 (SOX-13), carboxypeptidase H, Imogen 38, GLIMA 38, chromogranin-A, FISP-60, caboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor. In Addison's disease, main antigens include 21-hydroxylase, 17α-hydroxylase, and P450 side chain cleavage enzyme (P450scc); other antigens include ACTH receptor, P450c21 and P450c17. In premature ovarian failure, main antigens include FSH receptor and α-enolase. In autoimmune hypophysitis, or pituitary autoimmune disease, main antigens include pituitary gland-specific protein factor (PGSF) 1 a and 2; another antigen is type 2 iodothyronine deiodinase. In multiple sclerosis, main antigens include myelin basic protein, myelin oligodendrocyte glycoprotein and proteolipid protein. In rheumatoid arthritis, a main antigen is collagen II. In immunogastritis, a main antigen is $H^+$, $K^+$-ATPase. In pernicious angemis, a main antigen is intrinsic factor. In celiac disease, main antigens are tissue transglutaminase and gliadin. In vitiligo, a main antigen is tyrosinase, and tyrosinase related protein 1 and 2. In myasthenia gravis, a main antigen is acetylcholine receptor. In pemphigus vulgaris and variants, main antigens are desmoglein 3, 1 and 4; other antigens include pemphaxin, desmocollins, plakoglobin, perplakin, desmoplakins, and acetylcholine receptor. In bullous pemphigoid, main antigens include BP180 and BP230; other antigens include plectin and laminin 5. In dermatitis herpetiformis Duhring, main antigens include endomysium and tissue transglutaminase. In epidermolysis bullosa acquisita, a main antigen is collagen VII. In systemic sclerosis, main antigens include matrix metalloproteinase 1 and 3, the collagen-specific molecular chaperone heat-shock protein 47, fibrillin-1, and PDGF receptor; other antigens include Scl-70, U1 RNP, Th/To, Ku, Jol, NAG-2, centromere proteins, topoisomerase I, nucleolar proteins, RNA polymerase I, II and III, PM-Slc, fibrillarin, and B23. In mixed connective tissue disease, a main antigen is UlsnRNP. In Sjogren's syndrome, the main antigens are nuclear antigens SS-A and SS-B; other antigens include fodrin, poly(ADP-ribose) polymerase and topoisomerase. In systemic lupus erythematosus, main antigens include nuclear proteins including SS-A, high mobility group box 1 (HMGB1), nucleosomes, histone proteins and double-stranded DNA. In Goodpasture's syndrome, main antigens include glomerular basement membrane proteins including collagen IV. In rheumatic heart disease, a main antigen is cardiac myosin. Other autoantigens revealed in autoimmune polyglandular syndrome type 1 include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega.

The tolerogenic antigen can be a foreign antigen against which a patient has developed an unwanted immune response. Examples are food antigens. Embodiments include testing a patient to identify foreign antigen and creating a molecular fusion that comprises the antigen and treating the patient to develop immunotolerance to the antigen or food. Examples of such foods and/or antigens are provided. Examples are from peanut: conarachin (Ara h 1), allergen II (Ara h 2), arachis agglutinin, conglutin (Ara h 6); from apple: 31 kda major allergen/disease resistance protein homolog (Mal d 2), lipid transfer protein precursor (Mal d 3), major allergen Mal d 1.03D (Mal d 1); from milk: a-lactalbumin (ALA), lactotransferrin; from kiwi: actinidin (Act c 1, Act d 1), phytocystatin, thaumatin-like protein (Act d 2), kiwellin (Act d 5); from mustard: 2S albumin (Sin a 1), 11 S globulin (Sin a 2), lipid transfer protein (Sin a 3), profilin (Sin a 4); from celery: profilin (Api g 4), high molecular weight glycoprotein (Api g 5); from shrimp: Pen a 1 allergen (Pen a 1), allergen Pen m 2 (Pen in 2), tropomyosin fast isoform; from wheat and/or other cereals: high molecular weight glutenin, low molecular weight glutenin, alpha- and gamma-gliadin, hordein, secalin, avenin; from strawberry: major strawberry allergy Fra a 1-E (Fra a 1), from banana: profilin (Mus xp 1).

Many protein drugs that are used in human and veterinary medicine induce immune responses, which create risks for the patient and limit the efficacy of the drug. This can occur with human proteins that have been engineered, with human proteins used in patients with congenital deficiencies in production of that protein, and with nonhuman proteins. It would be advantageous to tolerize a recipient to these protein drugs prior to initial administration, and it would be advantageous to tolerize a recipient to these protein drugs after initial administration and development of immune response. In patients with autoimmunity, the self-antigen(s) to which autoimmunity is developed are known. In these cases, it would be advantageous to tolerize subjects at risk prior to development of autoimmunity, and it would be advantageous to tolerize subjects at the time of or after development of biomolecular indicators of incipient autoimmunity. For example, in Type 1 diabetes mellitus, immunological indicators of autoimmunity are present before broad destruction of beta cells in the pancreas and onset of clinical disease involved in glucose homeostasis. It would be advantageous to tolerize a subject after detection of these immunological indicators prior to onset of clinical disease.

B. Immunosuppressants

The particle can include one or more immunosuppressants (also referred to herein as immunosuppressant agents, immunosuppressant drugs, immunosuppressive agents, and immunosuppressive drugs). Immunosuppressants are known in the art and include glucocorticoids, cytostatics (such as alkylating agents, antimetabolites, and cytotoxic antibodies), antibodies (such as those directed against T-cell receptors or 11-2 receptors), drugs acting on immunophilins (such as cyclosporine, tacrolimus, and sirolimus) and other drugs (such as interferons, opioids, TNF binding proteins, mycophenolate, and other small molecules such as fingolimod). The dosage ranges for immunosuppressant agents are known in the art. The specific dosage will depend upon the desired therapeutic effect, the route of administration, and on the duration of the treatment desired. For example, when used as an immunosuppressant, a cytostatic maybe administered at a lower dosage than when used in chemotherapy.

Immunosuppressants include, but are not limited to, FK506, prednisone, methylprednisolone, cyclophosphamide, thalidomide, azathioprine, and daclizumab, physalin B, physalin F, physalin G, seco-steroids purified from *Physalis angulata* L., 15-deoxyspergualin, MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane, paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea.

Other immunosuppressive agents include, for example, antibodies against other immune cell surface markers (e.g., CD40) or against cytokines, other fusion proteins, e.g., CTLA4Ig, or other immunosuppressive drugs (e.g., cyclosporin A, FK506-like compounds, rapamycin compounds, or steroids).

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds, as well as other methods in which Rapamycin has been administered are known in the art (See, e.g. WO 95/22972, WO 95/16691, WO 95/04738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

Rapamycin analogs include, for example, everolimus, ridaforolimus, remsirolimus, umirolimus, and zotarolimus.

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506 like compounds include, for example, those described in WO 00/01385. Preferably, the language "rapamycin compound" as used herein does not include FK506-like compounds.

C. Other Active Agents

The following are agents that may be used in combinations with antigen and immunosuppressant such as rapamycin, alone or in combination with antigen without immunosuppressant for immunomodulation.

In one embodiment, the immunosuppressant is a TNF-α blocker. In another embodiment, the immunosuppressant increases the amount of adenosine in the serum, see, for example, WO 08/147482. In a preferred embodiment, the immunosuppressant is CD73-Ig, recombinant CD73, or another agent (e.g. a cytokine or monoclonal antibody or small molecule) that increases the expression of CD73, see for example WO 04/084933. In another embodiment the immunosuppressant is Interferon-beta.

The compositions can be used in combination or succession with compounds that increase Treg activity or production. Exemplary Treg enhancing agents include, but are not limited to, glucocorticoid fluticasone, salmeterol, antibodies to IL-12, IFN-γ, and IL-4; vitamin D3, and dexamethasone, and combinations thereof. The compounds can increase or promote the activity of Tregs, increase the production of cytokines such as IL-10 from Tregs, increase the differentiation of Tregs, increase the number of Tregs, or increase the survival of Tregs. See also U.S. Published Application No. 2012/0276095.

Antibodies, small molecules and other compounds that reduce the bioactivity of proinflammatory cytokines can also be used. In some embodiments, the compounds reduce the bioactivity of IL-1, IL-6, IL-8, TNF-α (tumor necrosis factor alpha), TNF-β (lymphotoxin α, LT) or a combination thereof.

In one embodiment, the active agent is a therapeutic used to treat autoimmune diseases such as rheumatoid arthritis and lupus.

Another major category within biologics is tumor necrosis factor (TNF) blockers, which counteract high levels of inflammatory proteins. Etanercept (Enbrel), infliximab (Remicade) and adalimumab (Humira) are the most widely used. Another promising group is interleukin-1 (IL-1) blockers like anakinra (Kineret).

In some embodiments, the agent is an anti-inflammatory cytokine or chemokine, for example, transforming growth factor-beta (TGF-beta), interleukin (IL)-1 receptor antagonist, IL-4, IL-6, IL-10, IL-11, and IL-13. Specific cytokine receptors for IL-1, tumor necrosis factor-alpha, and IL-18 also function as pro-inflammatory cytokine inhibitors. The nature of anti-inflammatory cytokines and soluble cytokine receptors are known in the art and discussed in Opal and DePalo, Chest, 117(4):1162-72 (2000).

Retinoic acid is an additional therapeutic compound that can be used as an antinflammatory agent. See, for example, Capurso, et al., Self/Nonself, 1:4, 335-340 (2010).

Mycophenolate mofetil (MMF) and its active metabolite mycophenolic acid (MPA) are both very effective immunosuppressive agents. MMF has been used to treat autoimmune and inflammatory skin diseases. Lipsky, Lancet, 348: L1357-1359 (1996) and has become a valuable therapeutic option in children with autoimmune disease. Filler, et al., *Pediatric Rheumatol.*, 8:1 (2010). Mycophenolic acid (MPA) is a relatively new adjuvant drug that selectively inhibits T and B lymphocyte proliferation by suppressing de novo purine synthesis. Other steroid sparing immunosuppressive agents include azathioprine, methotrexate and cyclophosphamide.

MPA is the active form of mycophenolate mofetil, which is currently used as an immunosuppressant in humans for lupus and other autoimmune disease therapy (Ginzler, et al., *N Engl J Med*, 353(21):2219-28 (2005)). MPA has broad immunosuppressive effects on several immune cell types. MPA blocks the de novo synthesis pathway of guanine nucleotides. T and B cell proliferation is acutely impaired by MPA because these cells lack the biosynthetic salvage pathways that could circumvent impaired de novo guanine production (Jonsson, et al., *Clin Exp Immunol*, 124(3): 486-91 (2001); Quemeneur, et al., *J Immunol*, 169(5):2747-55 (2002); Jonsson, et al., *Int Immunopharmacol*, 3(1):31-7 (2003); and Kamen, et al., *J Immunol*, 187(7): 3603-12 (2011). Furthermore, MPA can impair the activation of dendritic cells and their ability to stimulate alloantigen responses (Mehling, et al., *J Immunol*, 165(5):2374-81 (2000); Lagaraine, et al., *Int Immunol*, 17(4):351-63 (2005); and Wadia, et al., *Hum Immunol*, 70(9):692-700 (2009)), and promote the development of tolerogenic dendritic cells (Lagaraine, et al., *J Leukoc Biol*, 84(4):1057-64 (2008)). Like many immunosuppressant drugs, MPA is very hydrophobic, with a reported partition coefficient (log P value) of 3.88 (Elbarbry, et al., *J Chromatogr B Analyt Technol Biomed Life Sci*, 859(2): 276-81(2007)).

An immunosuppressant can be any small molecule that suppresses the function of the immune system or that increases susceptibility to infectious diseases. In certain embodiments, the immunosuppressant is an inhibitor of T cell proliferation, an inhibitor of B cell proliferation, or an inhibitor of T cell and B cell proliferation. In certain embodiments the T cell or B cell proliferation inhibitors inhibit or regulate the synthesis of guanine monophosphate. For example, the immunosuppressant can be mycophenolic acid.

Alternatively, the immunosuppressant is a prodrug of mycophenolic acid including, but not limited to, mycophenolate mofetil (marketed under the trade names CELL-CEPT® by the Swedish company F. Hoffmann-La Roche Ltd.

A salt of the immunosuppressant may also be used, for example, a salt of mycophenolic acid includes, but is not limited to, the mycophenolate sodium (marketed under the trade name MYFORTIC® by Novartis. In some embodiments, the immunosuppressant is a purine analogue including, but not limited to, azathioprine (marketed under a variety of trade names including AZASAN® by Salix and IMURAN® by GlaxoSmithKline) or mercaptopurine (marketed under the trade name PURINETHOL® ((Mercaptopurine). In some embodiments the immunosuppressant is an antimetabolite that inhibits the use and/or the synthesis of purines, such as a purine nucleoside phosphorylase inhibitor.

Additionally, or alternatively, anti-inflammatory agents can be used. The anti-inflammatory agent can be non-steroidal, steroidal, or a combination thereof. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Nonsteroidal anti-inflammatory drugs (NSAIDs), are often administered to help ease symptoms like pain, swelling and stiffness. The most common used NSAIDs are ibuprofen and naproxen. Disease-modifying anti-rheumatic drugs (DMARDs), are agents which slow down- or even halt—the progress of a disease. The workhorse of this group is methotrexate. Other DMARDs include sulfasalazine (brand name Azulfidine) and leflunomide (Arava).

The more popular corticosteroids include prednisolone, hydrocortisone, methylprednisolone, dexamethasone, cortisone, triamcinolone, and betamethasone.

D. Liver or Dendritic CellTargeting Moiety

In some embodiments, one or more targeting moieties (also referred to herein as targeting molecules, and targeting signals) can be loaded into, attached to the surface of, and/or enclosed within the particle. Exemplary target molecules include proteins, peptides, nucleic acids, lipids, saccharides, or polysaccharides that bind to one or more targets associated with a tissue, cell, or extracellular matrix of the liver. Preferably, the targeting moiety is displayed on and preferably conjugated to the exterior surface of the particle. Preferably, the targeting moiety increases or enhances targeting of the particles to the liver, or tissue or cells thereof including liver cells and endothelial cells.

Various techniques can be used to engineer the surface of particles, such as covalent linkage of molecules (ligands) to nanosystems (polymers or lipids) (Tosi, et al., *SfN Neurosci San Diego* (USA), 1:84 (2010)).

The degree of specificity with which the particles are targeted can be modulated through the selection of a targeting molecule with the appropriate affinity and specificity. For example, antibodies are very specific. These can be polyclonal, monoclonal, fragments, recombinant, or single chain, many of which are commercially available or readily obtained using standard techniques. The targeting molecules may be conjugated to the terminus of one or more PEG chains present on the surface of the particle.

In some embodiments, the targeting moiety is an antibody or antigen binding fragment thereof that specifically recognizes a liver cell or tissue marker. Fragments are preferred since antibodies are very large, and can have limited diffusion through tissue. Suitable targeting molecules that can be used to direct the particle to cells and tissues of interest, as well as methods of conjugating target molecules to nanoparticles, are known in the art. See, for example, Ruoslahti, et al. *Nat. Rev. Cancer,* 2:83-90 (2002).

Targeting molecules can also include neuropilins and endothelial targeting molecules, integrins, selectins, adhesion molecules, cytokines, and chemokines.

In some embodiments, the targeting moiety is an antibody or an antibody binding domain in combination with an antibody binding domain. The antibody can be polyclonal, monoclonal, linear, humanized, chimeric or a fragment thereof. The antibody can be antibody fragment such as Fab, Fab', F(ab'), Fv diabody, linear antibody, or single chain antibody. Antibody binding domains are known in the art and include, for example, proteins as Protein A and Protein G from *Staphylococcus aureus*. Other domains known to bind antibodies are known in the art and can be substituted.

Targeting molecules can be covalently bound to particle using a variety of methods known in the art. In preferred embodiments the targeting moiety is attached to the particle by PEGylation or a biotin-avidin bridge.

Liver targeting moieties are known in the art. See, for example, U.S. Published Application No. 2014/0017329, which discusses, glycyrrhetinic acid (GA), lactobionic acid (LA), and combinations thereof are liver targeting agents.

Other lipid targeting moieties are discussed in Mishra, et al., *BioMed Research International*, Volume 2013, Article ID 382184, 20 pages. See, for example Table 1, which is reproduced below:

TABLE 1

Receptors For Liver Targets (adapted from Mishra, et al. supra)

| Hepatocytes | Endothelial cell | Kupffer cells | Hepatic stellate cells |
| --- | --- | --- | --- |
| Asialoglycoprotein receptor (ASGP-R) | Mannose/N-acetyl glucose amine R | Mannose/N-acetyl glucose amine R | M6P/IGF II R |
| HDL-R | Scavenger R (Class A1 and A11) | Galactose particle R | $\alpha_2$ macroglobulin R |
| LDL-R | Fc R immune complexes | Galactose specific R | Ferritin R |
| IgA-R | Matrix compound (hyaluronan fibronectin, denatured collagen PIIINP) | Fc R (immune complexes, opsonized material) | Uroplasminogen R |
| Scavenger R (Class BI) | | Scavenger R (Class AI, BI, BII, MARCO CD36 and macrosialin) | Thrombin R |
| Transferrin R | | LDL R matrix compounds (fibronectin) | RBP R matrix compounds (intregrin, collagen type VI, fibronectin $CD_{44}$) |

TABLE 1-continued

Receptors For Liver Targets (adapted from Mishra, et al. supra)

| Hepatocytes | Endothelial cell | Kupffer cells | Hepatic stellate cells |
|---|---|---|---|
| Insulin R | | Complement R (C3b and C1q) LPS R $\alpha_2$ macroglobulin R | |

*R: Receptor.

In preferred embodiments, the particles are targeted to the liver using a targeting moiety that enhances accumulation of the particles in the liver.

A particularly preferred target is DEC205+. DEC205+ a cell receptor with a m.w. of 205 kDa (DEC205) (Ring, et al., J. Immuno., doi:10.4049/jimmunol.1202592 (11 pages) (2013)). It is expressed by epithelial call and dendritic cells (DCs) and facilitates antigen presentation. Compositions for targeting DEC205+ are known in the art and include, for example, anti-DEC205+ antibody and fragments and fusions thereof (see, e.g., Silva-Sanchez, PLoS ONE 10(4): e0124828. doi:10.1371/journal.pone.0124828; Spiering, et al., J Immunol., 194(10):4804-13 (2015). doi: 10.4049/jimmunol.1400986. Epub 2015 Apr. 10). It is believed that DEC205-targeted nanoparticles utilize DEC205-mediated endocytosis to gain entry into target cells, which reduces their capacity to activate antigen-specific CD4 T cells. DCs that take up antigen via DEC205 are known to cross present via MHC class I, which can promote CD8 T cell deletional tolerance in mouse models of autoimmune diabetes and EAE.

In other embodiments, another C-type lectin receptor is targeted by the targeting moiety. In a particular example, the C-type lectin is Clec 9A.

In some embodiments, density of the targeting ligand is modulated to tune the tolerance inducing effect of the carrier.

D. Pharmaceutical Compositions

The nanoparticles can be formulated in liquid or solid form, for oral administration as a single or multiple dosage unit 1. Dosage Units The compositions described herein are typically formulated in dosage unit form for ease of administration and uniformity of dosage. It will be understood, however, that the total daily usage of the compositions will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and other factors well known in the medical arts.

In certain embodiments, dosage units contain PBA nanoparticles encapsulating active and/or imaging agents in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

2. Excipients

Excipients and/or carriers may be chosen based on the dosage form to be administered, the active agents being delivered, etc. Suitable excipients include surfactants, emulsifiers, emulsion stabilizers, anti-oxidants, emollients, humectants, chelating agents, suspending agents, thickening agents, occlusive agents, preservatives, stabilizing agents, pH modifying agents, solubilizing agents, solvents, flavoring agents, colorants, fragrances, and other excipients. As used herein, "excipient" does not include any bile acid or polymer thereof.

Suitable emulsifiers include, but are not limited to, straight chain or branched fatty acids, polyoxyethylene sorbitan fatty acid esters, sorbitan fatty acid esters, propylene glycol stearate, glyceryl stearate, polyethylene glycol, fatty alcohols, polymeric ethylene oxide-propylene oxide block copolymers, and combinations thereof.

Suitable surfactants include, but are not limited to, anionic surfactants, non-ionic surfactants, cationic surfactants, and amphoteric surfactants.

Suitable suspending agents include, but are not limited to, alginic acid, bentonite, carbomer, carboxymethylcellulose and salts thereof, colloidal oatmeal, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, EDTA, and combinations thereof.

Suitable humectants include, but are not limited to, glycerin, butylene glycol, propylene glycol, sorbitol, triacetin, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Excipients may include suspending agents such as sterile water, phosphate buffered saline, saline, or a non-aqeuous solution such as glycerol.

Particles can be provided as dry powders following spray drying or lyophilization.

Particles may be compressed into tablets, which may in turn be coated with a material such as an EUDRAGIT® to prevent release of the particles after passage through the stomach.

Particles may also be encapsulated in hard or soft gels, such as gelatin and alginate capsules and the enteric formulated soft gels sold by Banner Pharmaceuticals.

Particles may also be formulated for administration to mucosal surfaces, such as the mouth, nasal cavity, oral cavity, pulmonary system, rectal or vaginal surfaces.

Particles may also be provided in a kit, where the material to be delivery is provided separately from the dosage unit, then combined in powder or dry form or in solution prior to use. The agent to be delivered can be entrapped, encapsulated or bound to the bile salt polymers chemically or physically.

III. Methods of Making Nanoparticles

The PBA nanoparticles described herein can be prepared by a variety of methods.

1. Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. The nanoparticles with different sizes and morphologies can be obtained by this method. This method is useful for relatively stable polymers like PBA, polyesters and polystyrene.

2. Interfacial Polycondensation

Interfacial polycondensation is used to encapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid nanoparticles containing core material.

The solvent evaporation process can be used to entrap a liquid core material in a polymer such as PBA, PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a nanoparticles composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of microparticles or nanoparticles that have a more optimized release of the encapsulated material.

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid particles containing core material.

4. Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

5. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

6. Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

7. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=-24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

8. Fluorine-Mediated Supramolecular Assemblies:

Fluorinated bile acid units (either linear or branched) can be synthesized by reaction of a terminal carboxylate or hydroxyl group with an alkylfluorate anhydride (AFAA). The product can extracted into water initiating a fluorophobic effect, in which spontaneous aggregation of the fluorinated building blocks takes place preferentially and differently from a hydrophobic effect. Such assembly is dependent on both the thermal energy, extent of fluorination, enabling some thermodynamic and kinetic control over the final morphology. Fluorophobic-mediated self-assembly will provide the cohesive forces for aggregation and may serve as an intrinsically imageable system through 19F NMR. Fluorinated bile acids will also have a distinctly different biodistribution and clearance time which may serve to enhance the residence time of the system in the GI tract or in the pancreatic regions.

IV. Methods of Use

The particles are particularly useful for oral delivery, and show enhanced uptake by target organ such as the pancreas, liver, or colon. The pharmaceutical compositions can contain untargeted or targeted PBA nanoparticles encapsulating therapeutic and/or diagnostic/imaging agent.

Oral administration can be achieved via oral gavage, or by swallowing of the composition in liquid, or solid form. The liquid forms of orally administered compositions can be in a form of a solution or a liquid gel. Solid forms of orally administered compositions can be in the form of capsules, soft and hard gels, tablets, pills, powders, and granules.

Although described with reference to oral administration, it is understood that the same delivery may be achieved by delivery to a mucosal surface such as the mouth, nasal cavity, lung, lung, rectum or vagina.

The desired dosage may be delivered orally once a day, or multiple times a day. For example, the desired dosage may be delivered orally three times a day, two times a day, once a day, every other day, every third day, every week, every two weeks, every three weeks, or every four weeks. In certain embodiments, the desired dosage may be delivered using multiple daily administrations (e.g., two, three, four, five, six, seven, eight, nine, ten, eleven, twelve, thirteen, fourteen, or more administrations).

Oral administration of the PBA nanoparticles is particularly advantageous where a pH response is useful. The targeted delivery of the PBA nanoparticles and the pH-responsive release of an encapsulated therapeutic agent enable treatment with lower doses of the therapeutic to achieve the same efficacy as with a free drug, and lower side effects. The encapsulated agents are protected from the harsh acidic environment of the stomach and are released in the gut lumen, or released via exocytosis following uptake by macrophages, dendritic or antigen-presenting cells at sites of pancreatic or intestinal inflammation, the liver, spleen or pancreas. Therefore, the PBA nanoparticles improve the bioavailability of encapsulated agents after oral administration, by protecting the agents from degradation in the stomach, and delivering the agents to the site of action. The PBA nanoparticles increase bioavailability of orally delivered drugs in the pancreas, liver, and colon, when compared to the bioavailability of the same drugs delivered orally at the same dose in free form, or encapsulated in PLGA nanoparticles.

A. Disorders to be Treated.

A method of preventing, suppressing or treating a disease or condition may include administering to a subject in need thereof an oral dosage unit of the pharmaceutical composition containing the untargeted PBA nanoparticles encapsulating the one or more agent(s); delivering an effective amount of one or more agent(s), optionally to targeted tissue such as pancreas, liver, or colon; wherein the agent is released from the PBA nanoparticles at the target tissues, resulting in prevention, suppression or treatment of the disease.

The formulations are particularly useful for treatment of neoplasma of the colon, liver, spleen, pancreas, or adjacent areas. The formulations are also very useful in treating diseases of the gastrointestinal tract, including ulcers, irritable bowel disease (IBD), and colon cancers. The formulations are useful in treatment of inflammatory diseases and autoimmune and allergenic disease. The formulations are also efficacious in treating diseases such as diabetes.

Autoimmune and Inflammatory Diseases and Conditions

It will be appreciated that the compositions and methods disclosed herein have a broad range of applications including, but not limited to, treatment of autoimmune disease, therapies for transplant rejection, adjuvants for enhancement of immunosuppressive function, and cell therapies involving Tregs or tolerogenic DCs.

In some embodiments, the compositions and methods are used to treat chronic and persistent inflammation, which can be a major cause of the pathogenesis and progression of an autoimmune diseases or inflammatory condition. Accordingly, methods of treating inflammatory and autoimmune diseases and disorders can include administering to a subject in need thereof, an effective amount of a particle formulation or a pharmaceutical composition thereof, to reduce or ameliorate one or more symptoms of the disease or condition. Some of the applications are discussed in more detail below.

Representative inflammatory or autoimmune diseases and disorders that may be treated using the disclosed compositions and methods include, but are not limited to, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

Inhibition of Epitope Spreading

Epitope spreading refers to the ability of B and T cell immune response to diversify both at the level of specificity, from a single determinant to many sites on an auto antigen, and at the level of V gene usage (Monneaux, F. et al., *Arthritis & Rheumatism,* 46(6): 1430-1438 (2002). Epitope spreading is not restricted to systemic autoimmune disease. It has been described in T cell dependent organ specific diseases such as IDDM and multiple sclerosis in humans and EAE induced experimental animals with a variety of myelin proteins.

Epitope spreading involves the acquired recognition of new epitopes in the same self molecule as well as epitopes residing in proteins that are associated in the same macromolecular complex. Epitope spreading can be assessed by measuring delayed-type hypersensitivity (DTH) responses, methods of which are known in the art.

Therefore, in some embodiments, a method for inhibiting or reducing epitope spreading in a subject includes administering to the subject an effective amount of nanocarrier. In a preferred embodiment the particle formulation inhibits epitope spreading in individuals with multiple sclerosis.

Allergies

A similar methodology can be used to treat allergies, substituting the allergen of interest for the autoimmune stimulus. Typically, particles are administered to a subject in an effective amount to reduce or inhibit an allergy or allergic reaction.

Allergies are abnormal reactions of the immune system that occur in response to otherwise harmless substances. Allergies are among the most common of medical disorders. It is estimated that 60 million Americans, or more than one in every five people, suffer from some form of allergy, with similar proportions throughout much of the rest of the world. Allergy is the single largest reason for school absence and is a major source of lost productivity in the workplace.

An allergy is a type of immune reaction. Normally, the immune system responds to foreign microorganisms or particles by producing specific proteins called antibodies. These antibodies are capable of binding to identifying molecules, or antigens, on the foreign particle. This reaction between antibody and antigen sets off a series of chemical reactions designed to protect the body from infection. Sometimes, this same series of reactions is triggered by harmless, everyday substances such as pollen, dust, and animal danders. When this occurs, an allergy develops against the offending substance (an allergen.)

Mast cells, one of the major players in allergic reactions, capture and display a particular type of antibody, called immunoglobulin type E (IgE) that binds to allergens. Inside mast cells are small chemical-filled packets called granules. Granules contain a variety of potent chemicals, including histamine.

Immunologists separate allergic reactions into two main types: immediate hypersensitivity reactions, which are predominantly mast cell-mediated and occur within minutes of contact with allergen; and delayed hypersensitivity reactions, mediated by T cells (a type of white blood cells) and occurring hours to days after exposure.

Inhaled or ingested allergens usually cause immediate hypersensitivity reactions. Allergens bind to IgE antibodies on the surface of mast cells, which spill the contents of their granules out onto neighboring cells, including blood vessels and nerve cells. Histamine binds to the surfaces of these other cells through special proteins called histamine receptors. Interaction of histamine with receptors on blood vessels causes increased leakiness, leading to the fluid collection, swelling and increased redness. Histamine also stimulates pain receptors, making tissue more sensitive and irritable. Symptoms last from one to several hours following contact. In the upper airways and eyes, immediate hyper-sensitivity reactions cause the runny nose and itchy, bloodshot eyes typical of allergic rhinitis. In the gastrointestinal tract, these reactions lead to swelling and irritation of the intestinal lining, which causes the cramping and diarrhea typical of food allergy. Allergens that enter the circulation may cause hives, angioedema, anaphylaxis, or atopic dermatitis.

Allergens on the skin usually cause delayed hypersensitivity reaction. Roving T cells contact the allergen, setting in motion a more prolonged immune response. This type of allergic response may develop over several days following contact with the allergen, and symptoms may persist for a week or more.

Allergens enter the body through four main routes: the airways, the skin, the gastrointestinal tract, and the circulatory system. Airborne allergens cause the sneezing, runny nose, and itchy, bloodshot eyes of hay fever (allergic rhinitis). Airborne allergens can also affect the lining of the lungs, causing asthma, or conjunctivitis (pink eye). Exposure to cockroach allergens has been associated with the development of asthma. Airborne allergens from household pets are another common source of environmental exposure. Allergens in food can cause itching and swelling of the lips and throat, cramps, and diarrhea. When absorbed into the bloodstream, they may cause hives (urticaria) or more severe reactions involving recurrent, non-inflammatory swelling of the skin, mucous membranes, organs, and brain (angioedema). Some food allergens may cause anaphylaxis, a potentially life-threatening condition marked by tissue swelling, airway constriction, and drop in blood pressure. Allergies to foods such as cow's milk, eggs, nuts, fish, and legumes (peanuts and soybeans) are common. Allergies to fruits and vegetables may also occur. In contact with the skin, allergens can cause reddening, itching, and blistering, called contact dermatitis. Skin reactions can also occur from allergens introduced through the airways or gastrointestinal tract. This type of reaction is known as atopic dermatitis. Dermatitis may arise from an allergic Dermatitis may arise from an allergic response (such as from poison ivy), or exposure to an irritant causing nonimmune damage to skin cells (such as soap, cold, and chemical agents). Injection of allergens, from insect bites and stings or drug administration, can introduce allergens directly into the circulation, where they may cause system-wide responses (including anaphylaxis), as well as the local ones of swelling and irritation at the injection site.

These can be treated by administration of anti-inflammatories, or by inducing tolerance to the antigen, as discussed in more detail below.

Diabetes

Diabetes, or diabetes mellitus, is due to either the pancreas not producing enough insulin or the cells of the body not responding properly to the insulin produced. There are three main types of diabetes mellitus:

Type 1 Diabetes results from the pancreas' failure to produce enough insulin or active insulin; this form was previously referred to as "insulin-dependent diabetes mellitus" (IDDM) or "juvenile diabetes", Type 2 Diabetes begins with insulin resistance, a condition in which cells fail to respond to insulin properly. As the disease progresses a lack of insulin may also develop; this form was previously referred to as "non insulin-dependent diabetes mellitus" (NIDDM) or "adult-onset diabetes"; and Gestational diabetes, the third main form, occurs when pregnant women, without a previous history of diabetes, develop a high blood sugar level.

Type 1 diabetes must be managed with insulin injections. Type 2 diabetes may be treated with medications with or without insulin. Gestational diabetes usually resolves after the birth of the baby.

People with type 1 diabetes need insulin therapy to survive. Many people with type 2 diabetes or gestational diabetes also need insulin therapy. Medications used for treating T2D include over 20 types of injectable insulin, and orally administered drugs such as meglitinides, sulfonylureas, metformin, canagliflozin, dapagliflozin, thiazolidinediones, pioglitazone, rosiglitazone, acarbose, pramlintide, exenatide, liraglutide, long-acting exenatide, albiglutide, dulaglutide, and dipeptidyl peptidase-4 (DPP-IV) inhibitors (sitagliptin, saxagliptin, linagliptin). These agents are collectively referred to as "anti-diabetics".

The compositions can be used to treat the inflammation of the pancreas (pancreatitis), the liver (hepatitis), or the colon (IBD). The PBA nanoparticles encapsulating a therapeutic and/or imaging agent, can pass through the fenestrated vasculature of an inflamed tissue, and are retained longer within the inflamed tissue, due to their size, compared to biologics or small molecule drugs (1-10 nm). They are also effectively internalized by antigen-presenting cells (such as macrophages and dendritic cells), making the PBA nanoparticles suitable for agent delivery to inflamed tissues and the cells of the immune system.

Two forms of pancreatitis, acute and chronic pancreatitis, can be treated with oral administration of the PBA compositions.

Acute pancreatitis is a sudden inflammation that lasts for a short time. It may range from mild discomfort to a severe, life-threatening illness. In severe cases, acute pancreatitis can result in bleeding into the gland, serious tissue damage, infection, and cyst formation. Severe pancreatitis can also harm other vital organs such as the heart, lungs, and kidneys.

Chronic pancreatitis is long-lasting inflammation of the pancreas. It most often happens after an episode of acute pancreatitis. Heavy alcohol drinking is another big cause. Damage to the pancreas from heavy alcohol use may not cause symptoms for many years, but then the subject may suddenly develop severe pancreatitis symptoms. Subjects with acute pancreatitis are treated with IV fluids and pain medications in the hospital. Chronic pancreatitis can be difficult to treat. It involves pain relief and improved nutrition. Subjects are generally given pancreatic enzymes or insulin.

The inflammation of the liver (hepatitis) is characterized by the presence of inflammatory cells in the tissue of the organ. Hepatitis may occur with limited or no symptoms, but often leads to jaundice (a yellow discoloration of the skin, mucous membrane, and conjunctiva), poor appetite, and malaise. Hepatitis is acute when it lasts less than six months and chronic when it persists longer.

Acute hepatitis can be self-limiting (healing on its own), can progress to chronic hepatitis, or, rarely, can cause acute liver failure. Chronic hepatitis may have no symptoms, or may progress over time to fibrosis (scarring of the liver) and cirrhosis (chronic liver failure). Cirrhosis of the liver increases the risk of developing hepatocellular carcinoma.

Viral hepatitis is the most common cause of liver inflammation. Other causes include autoimmune diseases and ingestion of toxic substances (notably alcohol), certain medications (such as paracetamol), some industrial organic solvents, and plants. Antiretroviral drugs such as tenofovir and entecavir are used for the treatment of chronic hepatitis B.

Inflammatory Bowel Disease.

Inflammatory bowel disease (IBD) is a broad term that describes conditions with chronic or recurring immune response and inflammation of the gastrointestinal tract. The two most common inflammatory bowel diseases are ulcerative colitis and Crohn's disease. Inflammation affects the entire digestive tract in Crohn's disease and only the large intestine in ulcerative colitis. Both illnesses are characterized by an abnormal response to the body's immune system.

Crohn's disease is treated with medications designed to suppress the immune system's abnormal inflammatory response that causes the symptoms. Suppressing inflammation offers relief from common symptoms like fever, diarrhea, and pain, and healing of the intestinal tissues. Combination therapy could include the addition of a biologic to an immunomodulator. As with all therapies, there are risks and benefits of combination therapies. Combining medications with immunomodulatory therapies can increase the effectiveness of IBD treatment.

Examples of agents used to treat IBD symptoms include, but are not limited to, sulfasalazine, mesalamine, olsalazine, and balsalazide that contain 5-aminosalicylate acid (5-ASA), corticosteroids, immunomodulators, antibiotics, and biologic therapies.

Neoplasms.

The compositions described herein can be used to treat various neoplasms of the pancreas, liver, or colon and other cancers in or adjacent to the gastrointestinal tract. The pancreatic neoplasms include, but are not limited to, primary pancreatic neoplasms such as pancreatic ductal adenocarcinoma, cystic neoplasm, intraductal papillary nucinous neoplasm. Endocrine neoplasms include insulinoma, gastrinoma, glucagonoma, and somatostatinoma.

Neoplasms of the liver include benign and malignant neoplasms, including, but not limited to, hepatocellular adenoma, focal nodular hyperplasia, dysplastic nodule, hemangioma, hepatocellular carcinoma, carcinosarcoma, hepatoblastoma, angiosarcoma, hemangioendothelioma, primary lymphomas. Biliary benign and malignant neoplasms include, but are not limited to, bile duct cyst, peribiliary gland hamartoma, biliary cystadenoma, biliary cystadenocarcinoma, and cholangiocarcinoma (Goodman, *Modern Pathology,* 20:S49-S60 (2007)).

About 95% of colorectal cancers arise from adenomas (tumors of benign neoplastic epithelium with variable potential for malignancy), which can be classified as polypoid, non-polypoid, or mixed types. Moreover, subjects with long-lasting IBD colitis have a higher risk of developing colorectal cancer, than has the general population (Facciorusso et al., *World J. Gastroenterol.,* 21(17):5149-5157 (2015)).

Treatment of the neoplasms may include targeted delivery of the PBA nanoparticles encapsulating anti-proliferative, chemotherapeutic, immunomodulatory, radiologic agents, or kinase inhibitors, to the pancreas, liver or colon. Because the PBA nanoparticles are also able to enter portal circulation in the liver, they are particularly suited to target liver neoplasms.

Delivery of Antigen and Induction of Tolerance

Methods of inducing tolerance are provided. The methods are generally based on the principle that immune suppressive drug and/or antigen can be targeted to the liver using the disclosed particles and will be taken up by liver dendritic cells (DC) and/or liver endothelial cells (EC). The liver is an organ of interest for targeting agents for induction of tolerance against those agents. It is believed that compositions loaded with antigen of interest and/or in combination with an immunosuppressive agent, will facilitate peripheral tolerance against the antigen of interest. The targeting can be passive (i.e retention in the liver) or active (i.e targeted to specific cells in the liver). Accordingly, a liver targeting moiety is optional.

Particles carrying antigen and/or immunosuppressive drug are preferably spatially localized to the same liver dendritic cell or liver endothelial cell for initiation of tolerance. Therefore, although different particles carrying antigen in one set and immunosuppressive agent in another set and injected together are contemplated, nanoparticles carrying both agents and targeted to liver dendritic cells or endothelial cells are preferred.

A preferred strategy generally includes administration of particles including an antigen and immunosuppressive agent that are retained in the liver and taken up by liver antigen presenting cell or endothelial cells. Tolergenic dendritic cells then circulate throughout the body to induce tolerance (peripheral tolerance) to the encapsulated antigen. Exemplary cells that can serve as live antigen presenting cells include liver dendritic cells (DCs), liver endothelial cells, Kupffer cells, Hepatic stellate cells, hepatocytes, and other cells that present antigens to the liver.

Liver DCs or ECs drain to local lymph nodes (Celiac). They acquire a tolerogenic program that induces the expansion of antigen-specific regulatory T cells (Tregs). APCs can also present antigen to T cells in the sinusoids without migrating out. Furthermore, the antigen may be processed by the DC while it is in the liver or the lymph nodes, or even while migrating between them. Generally, intracellular accumulation, trafficking or retention of the carrier in liver cells is important for tolerance induction.

Antigen-presenting cells also express anti-inflammatory markers or markers signifying the initiation of a tolerogenic phenotype. Tregs migrate from the lymph nodes into circulation and induce system-wide tolerance.

A preferred strategy can be summarized in five steps:
1) Homing to liver;
2) Uptake by dendritic cells and/or APCs in the liver;
3) Drainage to local lymphatics;
4) Expansion of regulatory T cells;
5) Migration into the bloodstream and initiation of peripheral tolerance.

The methods disclosed herein generally include administering a subject in need thereof an effective amount of the disclosed particles, most typically in a pharmaceutical composition, to induce or increase tolerance to an antigen of interest. In particular embodiments, the composition increases the number or activity of regulatory T cells. Accordingly, pharmaceutical compositions including particles including a tolerogenic antigen and/or an immunosuppressive agent present in the composition in an effective amount to induce liver dendritic cells and/or liver endothelial cells to acquire a tolerogenic phenotype, induce the expansion of antigen-specific regulatory T cells (Tregs), or a combination thereof, and method of use thereof are provided.

Robust tolerance may be achieved through induction of antigen-specific Tregs, polyclonal Tregs, Tr1 cells, other CD4 cells expressing PD-L1 or CTLA-4, CD8 cell deletion/anergy, even Bregs. Thus, in some embodiments, the composition is administered in an effective amount to acquire a tolerogenic program that reduces or prevents immunogenicity against a desired antigen, for example, the antigen delivered by the particle.

Administration is not limited to the treatment of an existing condition or disease but can also be used to prevent or lower the risk of developing such diseases in an individual, i.e., for prophylactic use. The compositions can be utilized in prophylactic vaccines or therapies, or therapeutic vaccines or therapies, which can be used to initiate or enhance a subject's immune tolerance to a pre-existing antigen, or to a new antigen.

The desired outcome of a prophylactic, therapeutic or de-sensitized immune response may vary according to the disease, according to principles well known in the art. Similarly, immune tolerance may completely treat a disease, may alleviate symptoms, or may be one facet in an overall therapeutic intervention against a disease.

Potential candidates for prophylactic vaccination include individuals with a high risk of developing autoimmunity against a certain self-antigen, and patients receiving recombinant protein therapy (FVIII or FIX).

B. Imaging

In other embodiments, the methods of using the pharmaceutical compositions may include methods of non-invasively imaging the target organ as a whole, or distinct microenvironments within the target organ, such as pockets of inflammation, leaky vasculature, or neoplasms. In these embodiments, the methods include administering to a subject in need thereof an oral dosage unit of the pharmaceutical composition containing the untargeted PBA nanoparticles encapsulating an effective amount of an imaging agent; delivering the effective amount of the imaging agent to target tissue, such as pancreas, liver, or colon; optionally releasing the effective amount of the imaging agent from the nanoparticles at the target tissues; which results in enhanced detection of target tissue, or a distinct microenvironment within the target tissue, via non-invasive imaging.

Imaging modalities suitable for detecting the PBA nanoparticles, and/or the agents therein include positron-emission tomography (PET), computed tomography (CT), magnetic resonance imaging (MRI), ultrasound imaging (US), and optical imaging. Suitable imaging agents (tracers) include radionuclide-labeled small molecules, such as F-18 fluorodeoxyglucose, superparamagnetic iron oxide (SPIO), gadolinium, europium, diethylene triamine pentacetic acid (DTPA), 1,4,7,10-tetraazacyclododecane-1,4,7,10-tetraacetic acid (DOTA) and their derivatives, gas, and fluorescent tracers. Such uitable modalities with respective tracers are known in the art (Baum et al., *Theranostics*, 2(5)437-447 (2012)).

C. Combined Therapy and Diagnosis

In other embodiments the methods of preventing, suppressing or treating a disease or condition, and methods of non-invasively imaging the target organ or tissue, are combined. In this embodiment, the pharmaceutical compositions contain untargeted PBA nanoparticles encapsulating both a therapeutic and a diagnostic/imaging agent. The method may include administering to a subject in need of prevention, suppression, or treatment of disease in and imaging of a target tissue an oral dosage unit of the pharmaceutical composition containing the untargeted PBA nanoparticles encapsulating an effective amount of one or more active agent(s) and an effective amount of an imaging agent; delivering the PBA nanoparticles to target tissue, such as pancreas, liver, or colon; releasing the effective amount of the one or more agent(s) and, optionally, the effective amount of the imaging agent, from the PBA nanoparticles at the target tissues, resulting in prevention, suppression or treatment of the disease, and enhanced detection of target tissue, or a distinct microenvironment within the target tissue, via non-invasive imaging.

The present invention will be further understood by reference to the following non-limiting examples.

EXAMPLES

Bile acid is a critical component of the enterohepatic circulation system facilitating absorption and degradation of ingested food stuffs. Bile recirculation from the intestines to the liver is the basis for of healthy digestion and enhancement of orally ingested food products. In the Examples, bile acid polymers were formulated as nanoparticles to function as effective oral carriers of encapsulated therapeutic agents enhancing their bioavailability, which is limited by the poor absorption due to degradation in the low pH and digestive enzymes of the GI tract. The nanoparticles fabricated from polymerized bile acid (ursodeoxycholic acid) survive the digestive tract and deliver several different types of payloads to the pancreas, a notoriously inaccessible site of debilitating diseases like type 1 diabetes (T1D). Poly(bile acid) (PBA) NPs traffic to the pancreas after oral delivery by a mechanism involving first protection of the payload in the stomach microenvironment, followed by enhanced intestinal egress, then efficient macrophage uptake and circulation to the pancreatic microenvironment. PBA NPs loaded with the immunosuppressive rapamycin prevent and treat the onset of type 1 diabetes (T1D) in a non-obese diabetic (NOD) mouse model. Insulin-loaded PBA NPs stabilized blood sugar levels indefinitely compared to subcutaneously injected insulin or PLGA formulations encapsulating insulin. One formulation (ursodeoxycholic acid) had immunosuppressive properties on its own and synergized its immunosuppressive effect with encapsulated rapamycin and enhanced the delivery of encapsulated insulin.

Example 1. Preparation and Characterization of PBA Nanoparticles

Materials and Methods

Polymerization of Bile Acids

Bile Acids (Bas) were polymerized into PBAs by an esterification reaction, and the polymerization was confirmed by nuclear magnetic resonance (NMR) and gel permeation chromatography (GPC). PBA, PLGA, or composite NPs encapsulating probes or therapeutics were formulated using a water/oil/water double emulsion technique as previously described (Kossena et al., *J. Pharm. Sci.*, 92:634-638 (2002)). NP morphology was assessed by scanning electron microscopy (SEM), and NP hydrodynamic diameter and surface charge were measured by a Malvern Zetasizer (Worcestershire, UK). Dye leakage from NPs was monitored in acidic media (citrate buffer solution, pH 2.0) at 37° C. in the presence of pepsin (10 mg/mL). Further details are described in Supplementary Information.

PBA or PLGA (inherent viscosity 0.55-0.75 dL/g, carboxyl terminal) or the mixture (50:50) NPs encapsulating dyes (1,1'-dioctadecyl-3,3,3',3'-Tetramethylindotricarbocyanine Iodide (Dir) or coumarin 6 (C6)) or drugs (rapamycin or insulin) were formulated using an water/oil/water (w/o/w) double emulsion technique. Polymers or the mixture (100 mg) was dissolved in 2 mL chloroform containing 1 mg of Dir or 10 mg of C6 or 10 mg of rapamycin. Pure PBS (100 μL) or the PBS containing mouse insulin (10 μg) was added drop-wise to the chloroform polymer solution while vortexing and homogenized using an IKA T25 Digital Ultra-Turrax. This dispersant phase was then added drop-wise to a continuous phase of 5% poly-vinyl alcohol (PVA) and homogenized. The mixture was then added drop-wise to 200 mL of 0.2% PVA and left stirring for 2 h to evaporate the solvent. NPs were collected by centrifugation at 12,000 RPM for 20 min at 4° C. and then washed 3 times with deionized water. The particles were lyophilized and stored at −20° C.

Bile acids cholic acid, lithocholic acid, deoxycholic acid, cheno-deoxycholic acid, and urso-deoxycholic acid were selected to prepare double-emulsion-type (W/O/W) NPs after each BA was polymerized by esterification according to Scheme 1. After synthesis and purification, polymers were characterized by nuclear magnetic resonance (NMR) and gel permeation chromatography (GPC) to analyze polyesterification and to determine molecular weights, respectively (Table 1). Bile acids (BA)s (5.4 mmol), para-toluenesulfonic acid (0.652 mmol), and 4-dimethylaminopyridine (DMAP, 0.652 mmol) were added in 60 mL of a 5:1 anhydrous methylene chloride to anhydrous pyridine solvent mixture and stirred at 40° C. to yield a clear solution. To the reaction mixture, 6.92 mmol of diisopropyl carbodiimide was added and the reaction was allowed to proceed for 2 h in the nitrogen atmosphere. The polyester product, PBAs, was precipitated into 400 mL of cold anhydrous methanol, collected by centrifugation and dried to retain a white powder.

The molecular weights (MWs) of PBAs (10 mg/mL in chloroform) were evaluated with GPC using a Waters HPLC system equipped with a model 1515 isocratic pump, a 717 plus autosampler, and a 2414 refractive index (RI) detector with Waters Styragel columns HT6E and HT2 in series. Chloroform was utilized as the mobile phase with a flow rate of 1 mL/min, and both the columns and RI detector were maintained at 40° C. MW values were determined relative to a calibration curve generated from narrow polydispersity polystyrene standards from Aldrich Chemical. Empower II GPC software was used to run GPC instrumentation and subsequent chromatographic analysis.

The polymerization resulted from esterification of bile acid monomers using para-toluene sulfonic acid (PTSA), 4-dimethylaminopyridine (DMAP), and N,N'-diisopropylcarbodiimide (DIC). The schematic of the esterification reaction using urso-deoxycholic acid (UDCA) monomer forming a linear poly(bile acid) polymer is presented below:

Scheme 1

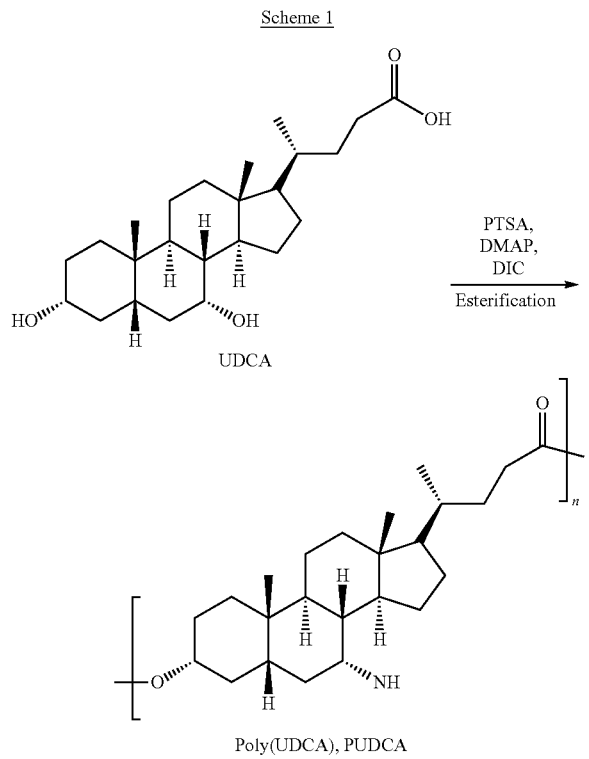

Poly(UDCA), PUDCA

Poly(Bile Acid) Nanoparticle Formation
NMR Analysis $^1$H and 2D-(COSY, DQFCOSY, HSQC and HMBC) NMR spectral data for UDCA and PUDCA were recorded on an Agilent (USA) NMR spectrometer at 600 MHz with a 3 mm cold probe or 400 MHz, and $^{13}$C NMR data was measured using a 100 MHz magnetic field. Chloroform-d$_1$ (99.96%, Cambridge Isotope Laboratories, Inc.) was used as the deuterated NMR solvent and solvent reference signals ($\delta_H$ 7.25, $\delta_C$ 76.98) for all NMR experiments. The complete polymerization of UDCA monomer via coupling of the carboxylic acid group at C-24 with 2 separate secondary alcohol groups at C-3 and C-7 was unambiguously supported by analyses of the NMR spectral data, including two-dimensional (COSY, DQFCOSY, HSQC and HMBC) NMR.

Statistical Analysis

Throughout the Examples, the experimental comparisons with multiple groups used ANOVA analysis with Bonferroni's post test. Two-tailed Student's t tests were performed for some comparisons, as indicated in the figure captions. A P value of 0.05 or less was considered statistically significant.

Results

The formed poly(bile acid) (PBA) polymers and their respective nanoparticles (NPs) were characterized for molecular weight, size (mean diameter), polydispersity index, Zeta-potential (mV), and dye-loading capacity. The results are summarized in Table 1 below. PLGA, and nanoparticles formed of PLGA, were used for comparison. PBA nanoparticle size distribution is presented in FIG. 1.

TABLE 2

Characteristics of synthesized PBA polymers and their respective nanoparticles.

| | Polymers | | | NPs | | | |
|---|---|---|---|---|---|---|---|
| | Mn[a] | Mw[b] | PDI[c] | Mean diameter (nm) | PDI[d] | Zeta-potential (mV) | NIR dye loading (%)[e] |
| PLGA | 2451 | 4184 | 1.707 | 328.8 ± 3.4 | 0.304 | −27.5 ± 2.8 | 0.699 ± 0.045 |
| PCA | 1972 | 2962 | 1.502 | 360.3 ± 11.2 | 0.296 | −24.6 ± 3.1 | 0.702 ± 0.012 |
| PLCA | 1357 | 1598 | 1.177 | 337.9 ± 21.0 | 0.276 | −27.1 ± 10.4 | 0.730 ± 0.020 |
| PDCA | 1842 | 2523 | 1.370 | 311.9 ± 24.1 | 0.213 | −22.7 ± 1.5 | 0.687 ± 0.064 |
| PCDCA | 1741 | 2284 | 1.312 | 335.1 ± 9.8 | 0.011 | −27.8 ± 10.1 | 0.687 ± 0.014 |
| PUDCA | 2225 | 3210 | 1.443 | 344.3 ± 4.7 | 0.164 | −24.9 ± 4.4 | 0.674 ± 0.005 |
| Blend (PUDCA/ PLGA) | | | | 299.5 ± 14.3 | 0.131 | −22.2 ± 5.6 | 0.726 ± 0.019 |

[a]The number average molar mass (gel permeation chromatography, GPC)
[b]The weight average molar mass (GPC)
[c]Polydispersity index (GPC)
[d]Polydispersity index (dynamic light scattering, DLS)
[e](weight of dye/weight of nanoparticles) × 100
[f]Composite nanoparticle (PLGA:PUDCA = 50:50, w/w)

The complete polymerization of UDCA monomer via coupling of the carboxylic acid group at C-24 with alcohol groups was unambiguously supported by the 1H and two-dimensional NMR analyses.

Representative PBA NPs, PUDCA NPs, exhibited spherical morphology in scanning electron micrographs (SEM), and the NP diameter was calculated as 344.3±4.7 nm. To isolate the biological effects of PBA properties on NP bioavailability, NP formulation was optimized to normalize by other biophysical parameters, such as particle diameter and surface charge, that influence bioavailability. Table 1 summarizes these parameters; the average hydrodynamic diameter was 331.1±20.3 nm, and average zeta-potential was −25.3±2.3 mV. Additionally, all NP were formulated to encapsulate similar levels of near infrared dye, 1,1'-dioctadecyl-3,3,3',3'-tetramethylindotricarbocyanine iodide (Dir), in order to ensure that NP doses contained the same fluorescence intensities.

PBA NPs were compared with PLGA NPs, which have been extensively studied in oral delivery. The commensurate material properties of polymers and NPs ensured that differences in bioavailability following oral administration resulted from physical and biochemical properties of PBAs.

Example 2. PBA Nanoparticles Show Greater Stability, Increased Cell Permeability, and Enhanced Cellular Uptake, when Compared to PLGA Nanoparticles Materials and Methods Dye Release in the Stomach Environment: Dir-NPs were dispersed in the media (citrate buffer solution, pH 2.0) at 37° C. in the presence of pepsin (10 mg/mL). Each time point, samples were centrifuged and supernatant was used to measure the amount of Dir released from the particles. EUDRAGIT® was added to PLGA NP dispersions (5%) and compared.

Uptake of NPs in BMM Bone marrow cells were harvested from C57BL/6 mice and cultured in Roswell Park Memorial Institute (RPMI) media with macrophage colony-stimulating factor (MCSF, 10 ng/mL) at 37° C. in a humidified atmosphere with 5% CO2. After 7 d, BMMs were seeded in a 96-well plate at a density of $1\times10^4$ cells per well and Dir-loaded NPs (Dir-NPs) were added to the medium. The cells were incubated for 2, 4, and 8 h and measured uptake of Dir-NPs using a plate reader after washing.

BMMs were also seeded at $7\times10^4$ cells/cm$^2$ on 0.4 μm pore transwell filters to monitor release of NPs from the cells. Dir-loaded NPs (1 mg/mL) were incubated with BMMs for 4 h and washed out prior to the experiment. The release media in the basolateral chamber was sampled and measured at each time point.

Intestinal permeability test Caco-2 cells were seeded at $7\times10^4$ cells/cm$^2$ on 0.4 μm pore transwell filters in Dulbecco's modified eagle media containing 10% fetal bovine serum (FBS), 100U/mL penicillin, 100 mg/mL streptomycin, and 0.1 mM non-essential amino acids. The cells were grown to confluency and allowed to mature for approximately 30 days at 37° C. and 5% CO2. Cell culture media was changed every 2-3 d. Prior to performing permeability studies, the transepithelial electrical resistance (TEER) was measured using an epithelial voltometer. Confluent cell layers with TEER values greater than 300×cm$^2$ were used for permeability and cytotoxicity studies. For permeability studies, a dispersion of 1 mg/mL Dir-loaded NPs or Dir solution was prepared in phenol-free Hank's balanced salt solution (HBSS) containing 25 mM glucose and added to the apical chamber of the transwell filter. HBSS containing 25 mM glucose (400 μL) was added to the basolateral chamber and 100 μL of the media in the basolateral chamber was sampled and replaced with 100 μL of fresh media at each time point of fluorescence measurement ($\lambda$ex: 750 nm, $\lambda$em: 790 nm). The rate of cumulative Dir transport to the basolateral chamber gave the flux, dQ/dt. The permeability (P) was calculated by dividing the flux by the initial concentration of total Dir in the apical chamber (CO) and the area of the transwell filter (A).

Results

Figure 2A:
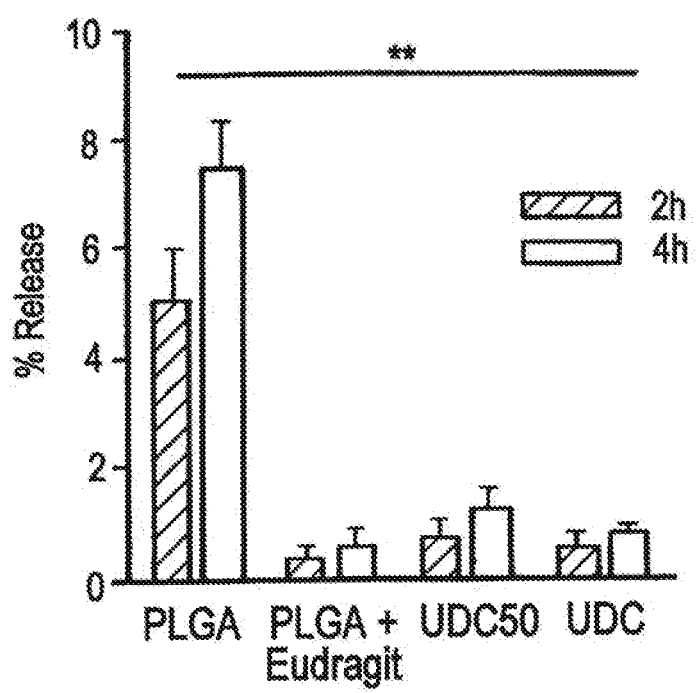
FIG. 2A is a bar graph showing percent release of DiR dye in in vitro stomach conditions (with stomach enzymes at pH 2.0) from nanoparticles formed of poly(lactic-co-glycolic) acid (PLGA), PLGA coated with EUDRAGIT, PLGA and poly(urso-deoxycholic acid) (UDC) blend (50:50) (UDC50), or PUDC alone at 2 hours or 4 hours.
Figure 2B:
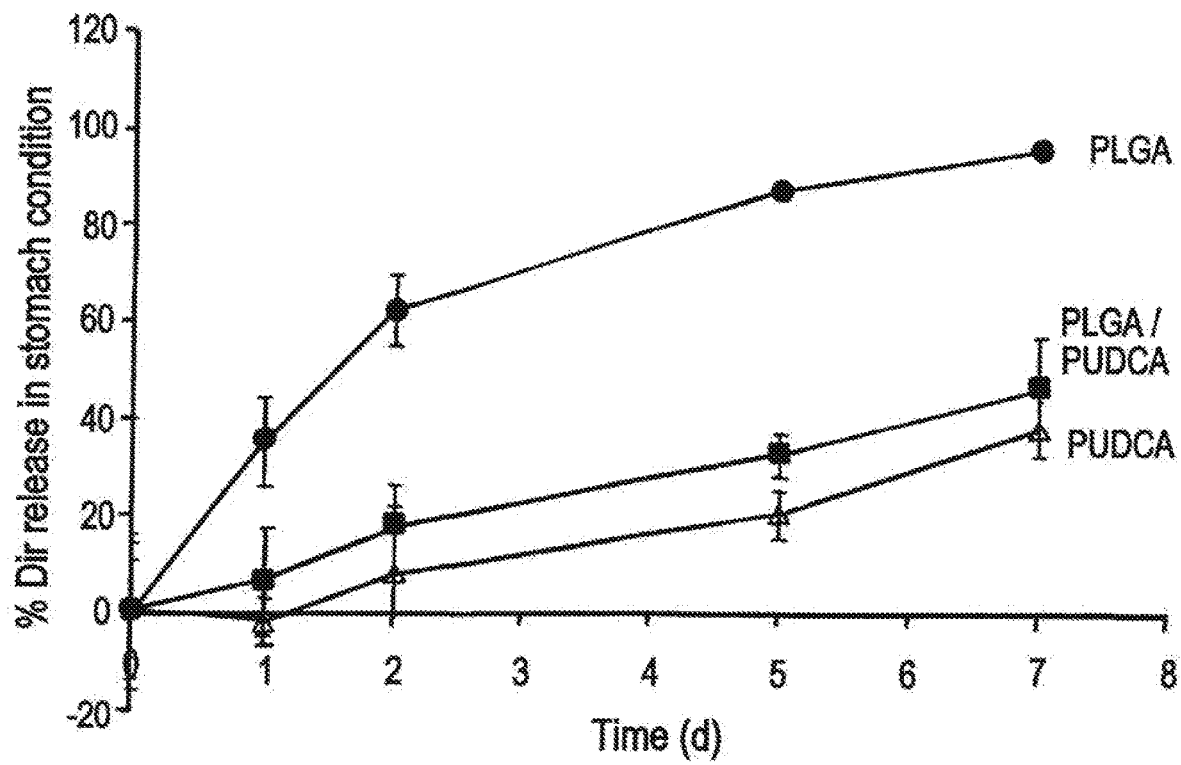
FIG. 2B is a line graph showing percent DiR release in stomach condition over time (days).

FIGS. 2A and 2B show that PUDCA nanoparticles were significantly more stable in stomach conditions when compared to the PLGA nanoparticles. The stability was measured as percent (%) release of DiR dye loaded into the nanoparticles. The percent release of the dye from PLGA nanoparticles at 2 hours or 4 hours incubation in stomach conditions was about 5.04±0.84%, or about 7.50±0.78% (p<0.0001) respectively, while that from PUDCA nanoparticles was about 0.82±0.10% at both time intervals This difference was statistically significant. At each time point, NPs were centrifuged and supernatant was collected to measure the amount of Dir released from the particles ($\lambda_{ex}$ 750 nm; $\lambda_{em}$ 790 nm). PLGA NPs showed 95% dye leakage over 7 days, while significantly slower dye release was found for PUDCA NPs. The particles prepared with a blend of PLGA and PUDCA had a release profile similar to that of PUDCA NPs (n=5).

Figure 2C:
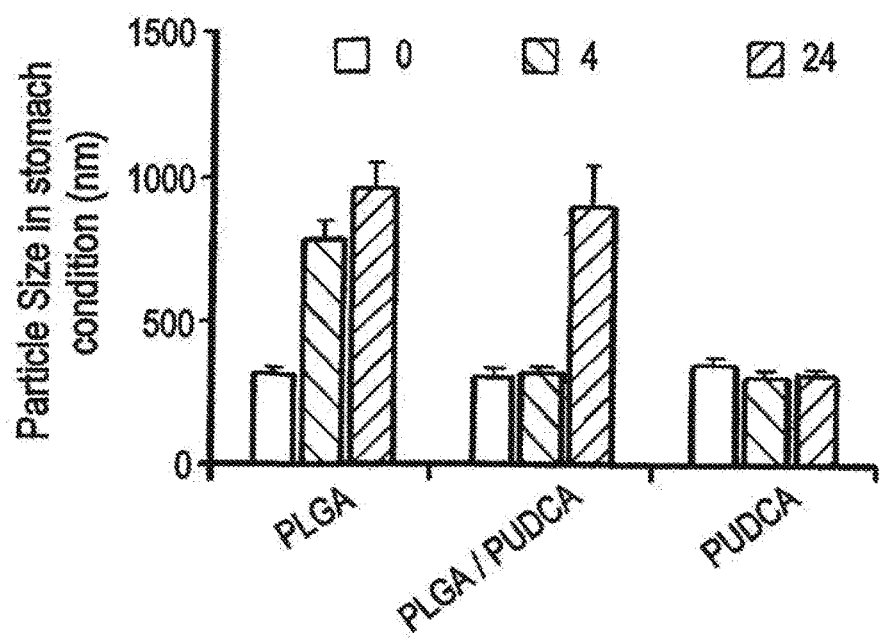
FIG. 2C is a bar graph of particle size (nm) for PLGA, PLGA/PUDCA, and PUDCA particles in stomach condition incubated for 0, 4, or 24 hours.

In stomach-mimicking media (a solution of pepsin in citrate buffer at pH 2.0, 37° C.), PLGA NPs leaked dye after 2 and 4 h incubations (FIG. 2A), and NPs aggregated due to particle destabilization by rapid hydrolysis (FIG. 2C), confirming previous findings that PLGA degradation is accelerated in acidic conditions. In contrast, dye leakage was minimized in PUDCA or composite NPs (fabricated as a 50/50 w/w mixture of PLGA and PUDCA), and these particles maintained their size for longer time periods. To reduce burst release of dye, PLGA NPs were coated with 5 wt % of EUDRAGIT®, a polyacrylate enteric coating that protects in low pH conditions, as a positive control.

Figure 2D:
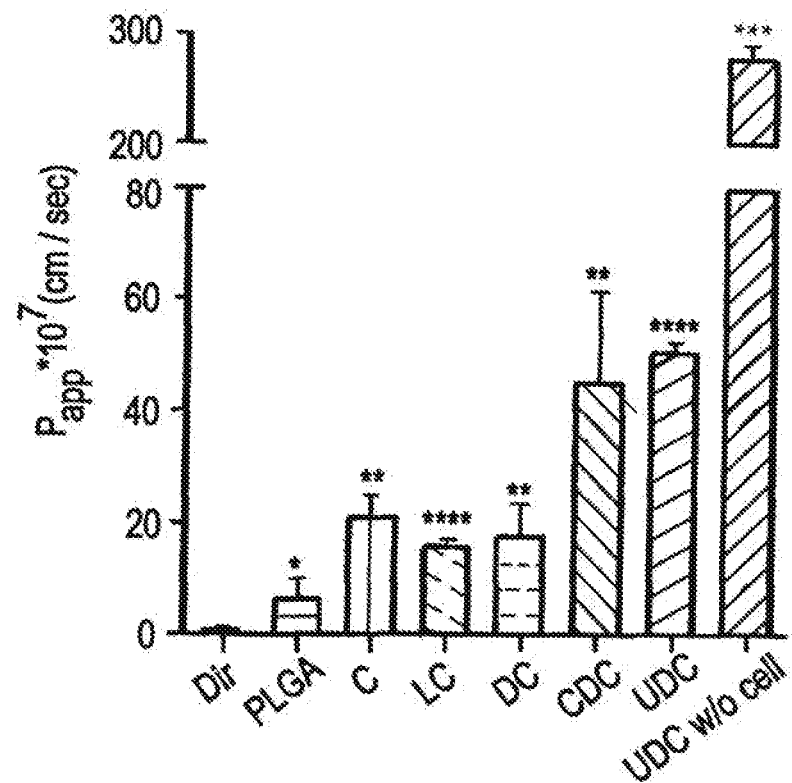
FIG. 2D is a bar graph showing resistance measurements in model human colonic cells (CaCo Cell line) in vitro. Permeability (apparent) measurements). (Papp*$10^{-7}$ (cm/secof the free dye DiR or nanoparticles formed of PLGA, poly(cholic acid) (C), poly(lithocholic acid) (LC), poly(deoxycholic acid) (DC), poly(cheno-deoxycholic acid) (CDC), or UDC and containing DiR. The permeability of the nanoparticles was measured in transwells though CaCo-2 cell monolayers.
Figure 2E:
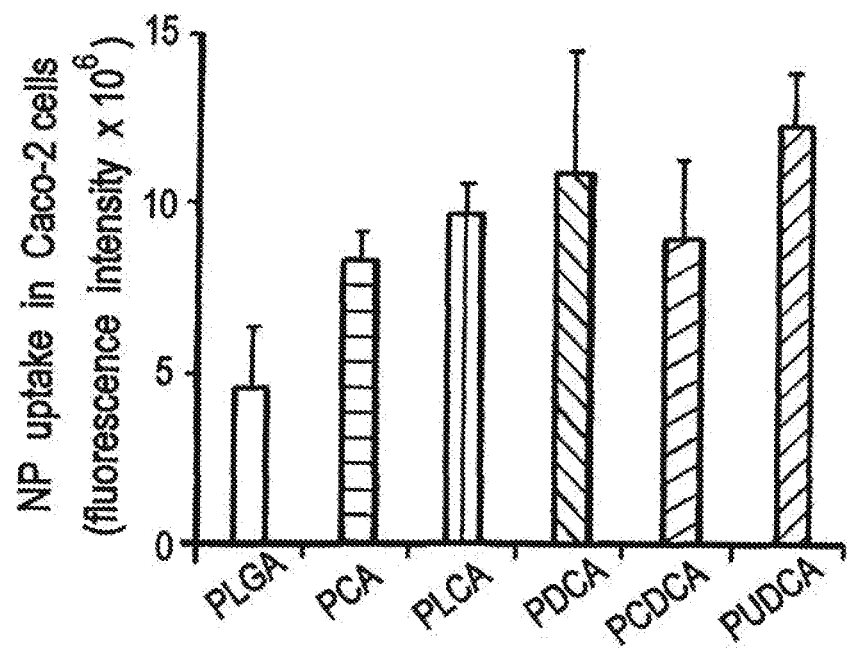
FIG. 2E is a bar graph showing NP uptake in Caco-2 cells. Caco-2 cells were seeded in a 96-well plate at a density of $1 \times 10^4$ cells per well and Dir-loaded NPs (Dir-NPs, 100 mg/mL) were added to the media to evaluate uptake of NPs in Caco-2 cells. Cells were incubated for 4 h and uptake of Dir-NPs was measured using a plate reader after washing.
Figure 2F:
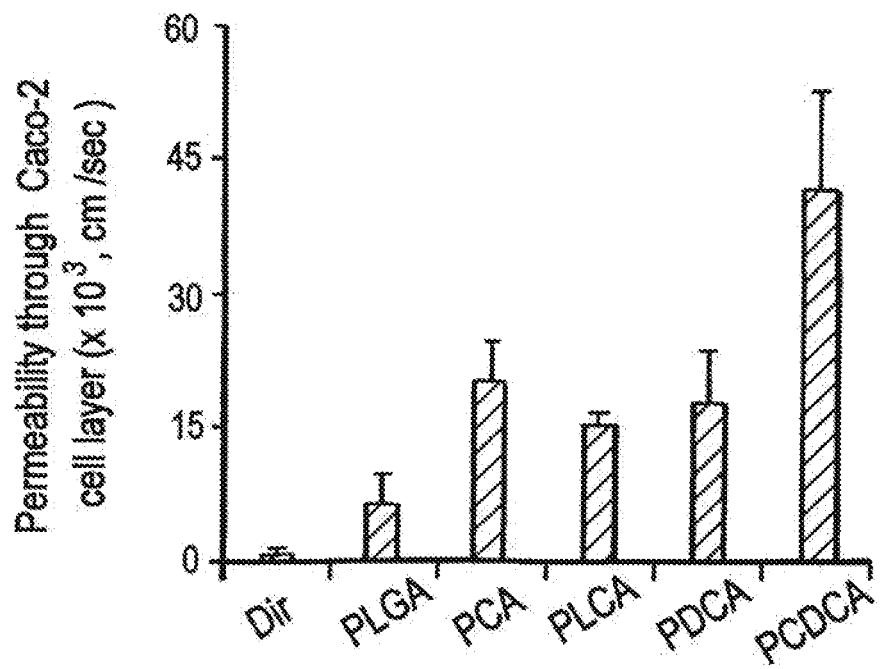
FIG. 2F is a bar graph showing permeability through Caco-2 cells layer ($\times 10^7$, cm/sec) of DiR, PLGA, and PAB NPs. For permeability studies, Caco-2 cells were seeded at $7 \times 10^4$ cells/cm$^2$ on 0.4 mm pore transwell filters for approximately 30 d at 37° C. and 5% $CO_2$. Dir-loaded NPs (1 mg/mL) or soluble Dir was added to the apical chamber of transwell filters and the media in the basolateral chamber was sampled to measure fluorescence intensity ($\lfloor$ex: 750 nm, $\lfloor$em: 790 nm).
Figure 2G:
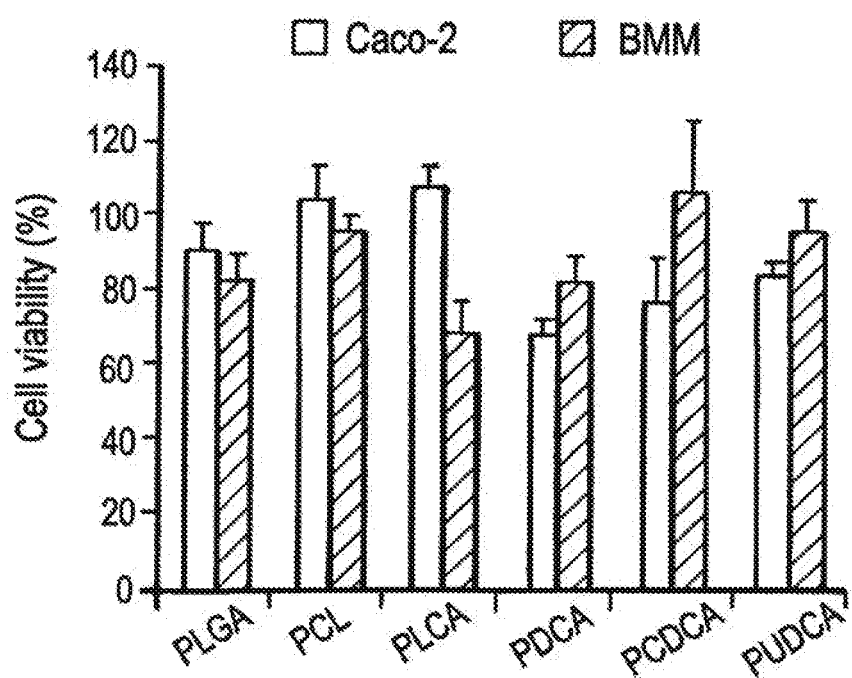
FIG. 2G is a bar graph showing cell viability (%) for Caco-2 and BMM cells incubated with PLGA or PAB NPs. Caco-2 cells or BMMs were seeded in a 96-well plate at a density of $1 \times 10^4$ cells per well and Dir-NPs (1 mg/mL) were added to the media. Cells were incubated for 4 h and the cell viability was measured using a CellTiter-Blue® Cell Viability Assay. PBA NPs exhibited faster uptake and greater permeability in Caco-2 cells than PLGA NPs. Moderate cytotoxicity in Caco-2 cells and BMMs was observed for NPs used in the study.
Figure 2H:
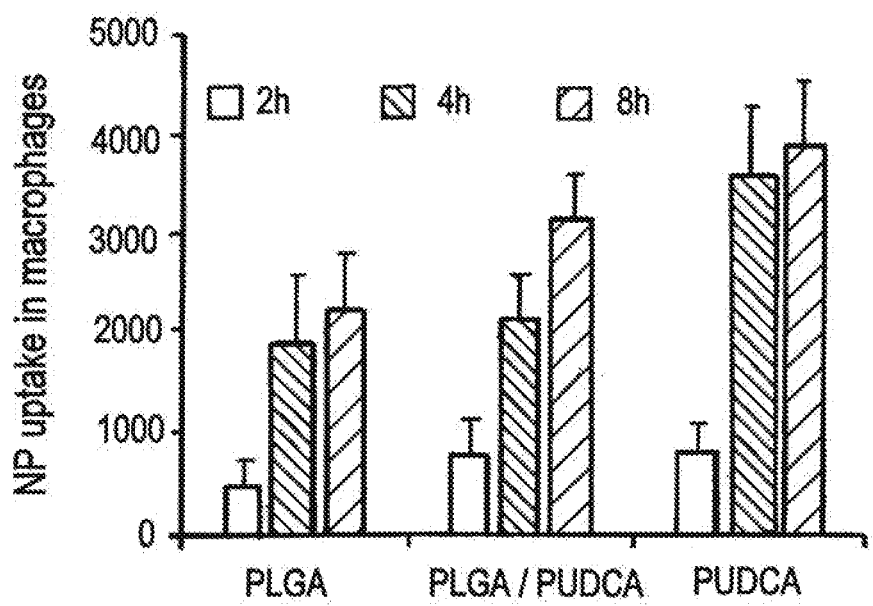
FIG. 2H is a bar graph showing fluorescence intensity of bone marrow derived macrophages (BMDM) after incubation with DiR-loaded PLGA, PLGA and UDC blend (50:50) (UDC50), or UDC nanoparticles for 2, 4 or 8 hours.
Figure 2I:
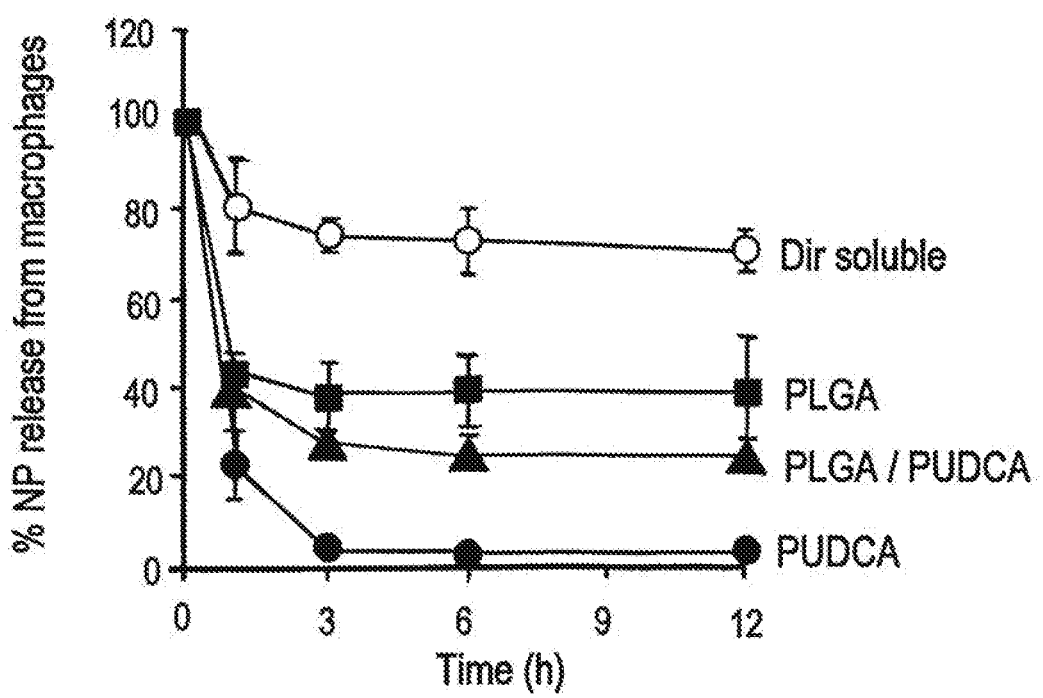
FIG. 2I is a line graph showing release of NPs from BMMs after cellular uptake.
Figure 2J:
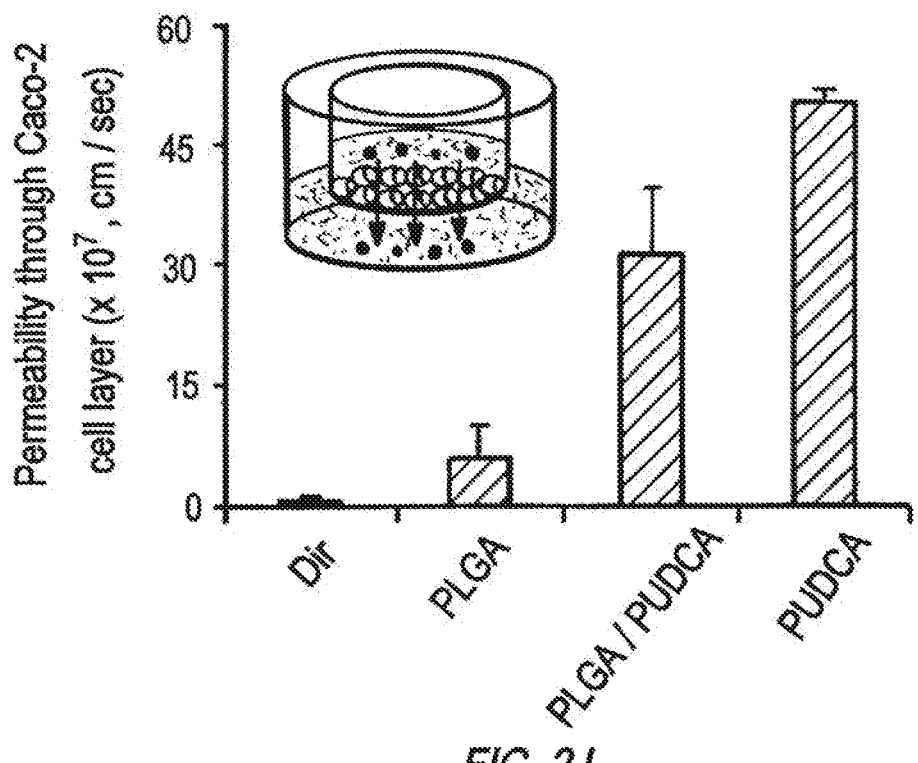
FIG. 2J is a bar graph showing permeability through Caco-2 cells layer ($\times 10^7$, cm/sec) of DiR, PLGA, PLGA/PUDCA, and PUDCA NPs.

In addition, permeability of PBA nanoparticles through a monolayer of CaCo2 cells in a transwell system was significantly greater than that of PLGA nanoparticles (FIG. 2D). Specifically, PUDCA nanoparticles showed five-fold faster absorption through the monolayer than did the PLGA nanoparticles (PUDCA: $50.63\times10^7$ cm/sec, PLGA: $6.45\times10^7$ cm/sec, p<0.0001). To assess another important metric of particle absorption into the intestinal layer, a transwell experiment in which Dir-loaded NPs passed through a Caco-2 monolayer, a common human intestinal model, was conducted. NPs formulated with PUDCA significantly enhanced intestinal permeability, while transport of free dye and PLGA NPs were significantly slower (FIG. 2J). Composite NPs (PLGA/PUDCA) exhibited kinetics between those made purely of PLGA or PUDCA.

Similarly, PUDCA nanoparticles are preferentially taken up by bone marrow derived macrophages (BMDM). The fluorescence intensity of BMDM incubated for 4 or 8 hours with 1 mg/ml PUDCA nanoparticles was significantly greater than that with 1 mg/ml PLGA nanoparticles (FIG. 2H) p=0.023.

Studies have shown that material properties of particles are critical to determine the particle-macrophage interaction and thus particle uptake in macrophages. FIG. 2H shows a composition-dependent uptake of NPs in BMMs as a function of incubation time. As the proportion of PUDCA in NPs increased, faster NP macrophage uptake was observed. Notably, the release of NPs from BMMs was also faster for PUDCA NPs (FIG. 2I), perhaps because PUDCA is a polymerized cholesterol, a cell membrane-friendly molecule, and may easily enter/escape cells by readily opening up cell membranes, in the same manner that BAs penetrate intestinal cell layers to enter the bloodstream. Indeed, BAs have been shown to disrupt tight junctions in the epithelial lining, enabling paracellular and transcellular transport pathways. Likewise, PUDCA NPs exhibited high uptake in Caco-2 cells (FIGS. 2E, 2F, and 2G) and rapid exocytosis, showing substantial permeability through Caco-2 cell layers.

Example 3. PBA Nanoparticles are Generally Non-Toxic

Materials and Methods

To evaluate the cytotoxicity of formulations, NP (1 mg/mL) were incubated with Caco-2 or NIH-3T3 cells, which were seeded in a 96-well plate at a density of $10^4$ cells per well and cultured at 37° C. in a humidified atmosphere with 5% CO2. The cells were incubated for 24 h and the number of viable cells was determined using an MTT colorimetric assay. The well plate was incubated for 4 h and the absorbance at 570 nm was recorded.

Results

Figure 3A:
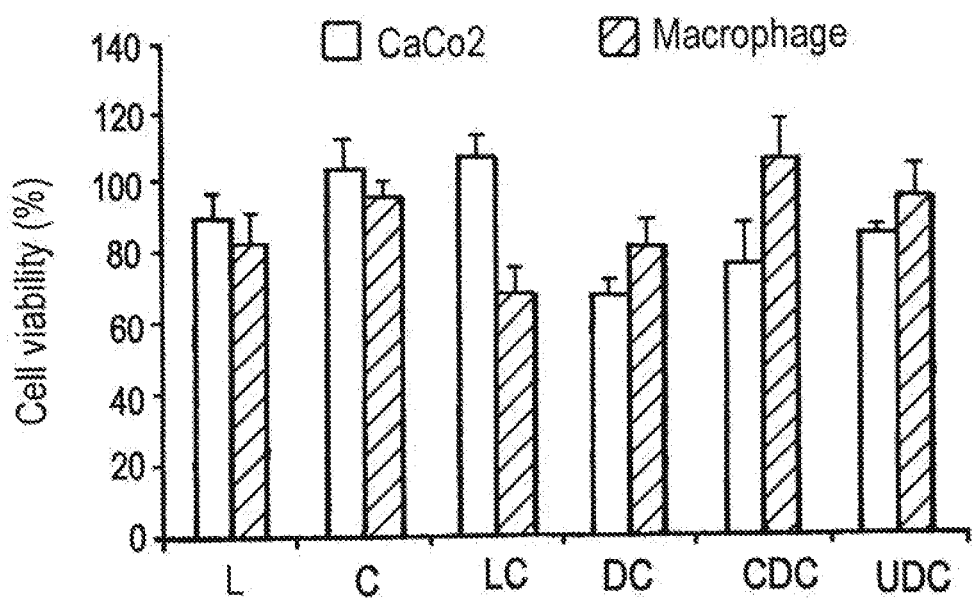
FIGS. 3A and 3B are bar graphs showing CaCo-2, Macrophage (FIG. 3A), and NIH-3T3 (FIG. 3B) cell viability (%) when incubated for 24 hours in culture with nanoparticles formed of PLGA (L), poly(cholic acid) (C), poly(lithocholic acid) (LC), poly(deoxycholic acid) (DC), poly(cheno-deoxycholic acid) (CDC), or poly(urso-deoxycholic acid) (UDC) as described with reference to FIG. 2.
Figure 3B:
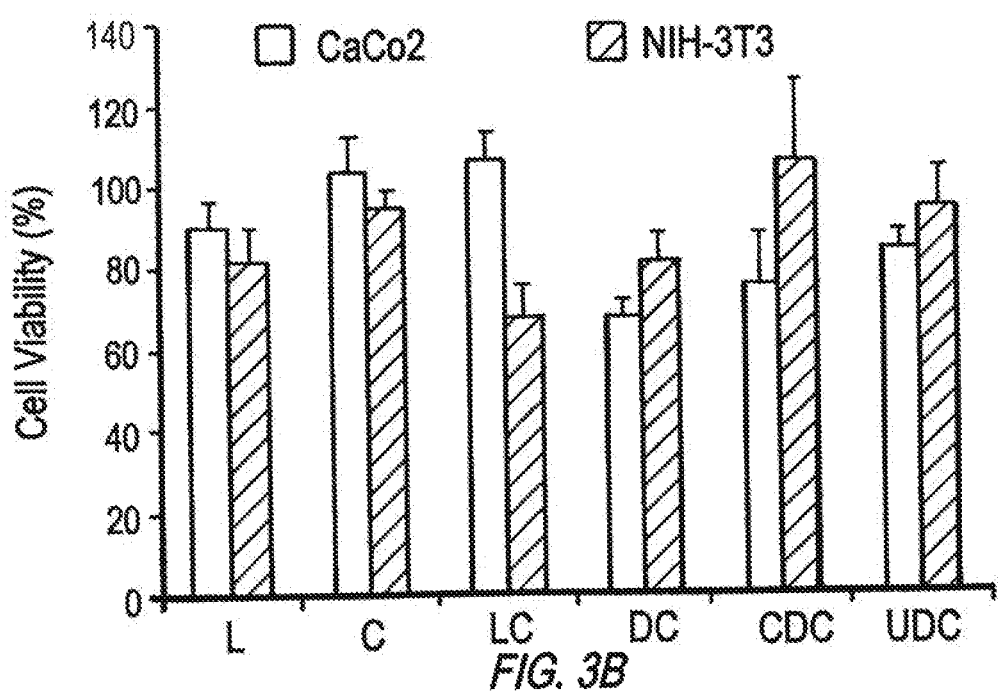

The results indicate that cell viability depends on the nanoparticle composition as well as the cell line (FIGS. 3A and 3B). Generally, PBA nanoparticles are non-toxic. Specifically, nanoparticles formed of PUDCA or PLGA have similar effect on cell viability (FIGS. 3A and 3B).

Example 4. Biodistribution of PBA Nanoparticles Following Oral Gavage

Materials and Methods

DiR-loaded nanoparticles formed of PLGA, poly(cholic acid) (C, or PCA), poly(lithocholic acid) (LC, or PLCA), poly(deoxycholic acid) (DC, or PDCA), poly(cheno-deoxycholic acid) (CDC, or PCDCA), or UDC (or PUDCA) at 5 mg/ml concentration were administered via oral gavage in a 300 µl volume. Four hours after administration, the mice were sacrificed and the DiR fluorescence from various organs quantified. The results are presented in FIGS. 4A-4C.

C57BL/6 mice (6-8-week-old) were housed in autoclaved micro-isolator cages that were placed in a positive pressure containment rack and maintained according to an approved protocol from the Yale University Institutional Animal Care and Use Committee. The mice were randomly assigned to experimental and control groups of 3-5 animals each. The mice were fasted for 4 h and treated with Dir- or C6-encapsulated NPs by oral injection (0.5 g/kg). Free Dir or C6 solubilized with TWEEN 20® served as a control.

Mice were sacrificed at time points of 4, 8, 12, or 24 h post-gavage, and a Bruker molecular imaging instrument (Carestream Health, Inc., Rochester, USA) was used to scan organs ex vivo to measure fluorescence intensity. Pancreas from mice that received iron oxide-loaded PUDCA NPs were fixed for histological analysis by hematoxylin and eosin (H&E) and Prussian Blue staining. Organs were also harvested from mice that received C6-loaded PUDCA NPs and stained with antibodies against F480 to analyze macrophages associated with the NPs by flow cytometry. Each formulation was also intravenously administered (i.v.) to mice via tail vein injection to evaluate biodistribution (100 mg/kg, 50 µL). Clodrosome (Clodronate-containing liposomes, 100 mg/kg, i.p.) was used to deplete macrophages.

Results

Figure 4A:
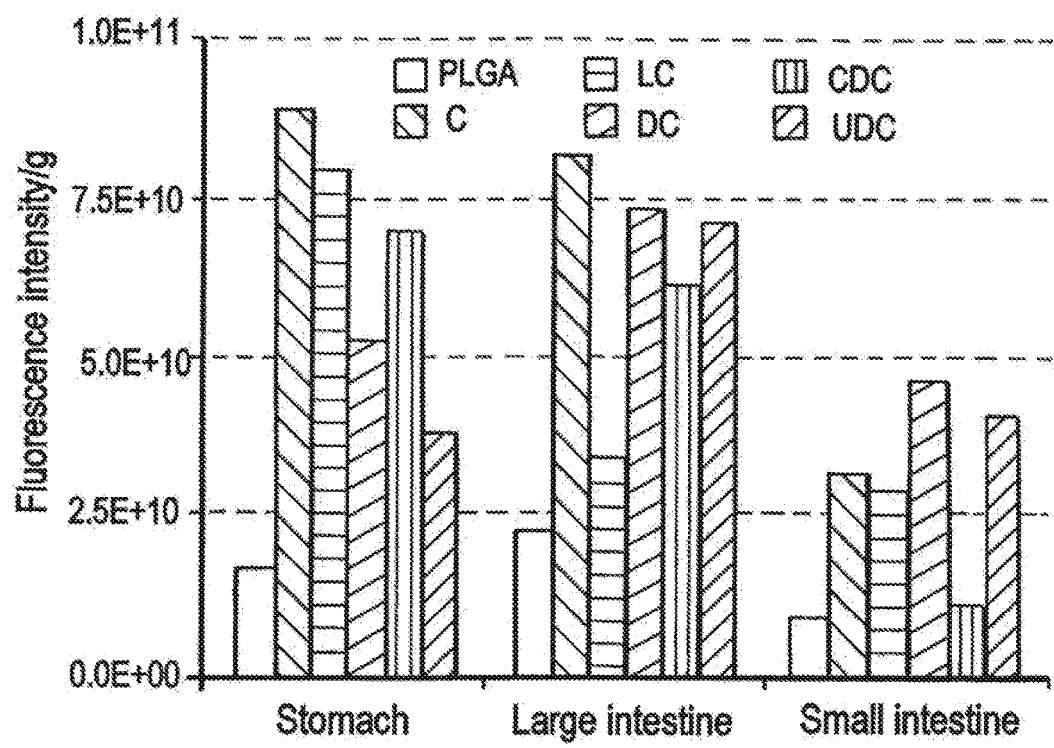
FIG. 4A is a bar graph showing fluorescence intensity per gram of stomach, large intestine, or small intestine tissue 4 hours after oral administration DiR-loaded nanoparticles formed of PLGA (L), poly(cholic acid) (C), poly(lithocholic acid) (LC), poly(deoxycholic acid) (DC), poly(cheno-deoxycholic acid) (CDC), or poly(urso-deoxycholic acid) (UDC). The nanoparticles were administered in 300 µl volume at a concentration of 5 mg/ml.

The nanoparticles made of PBA or PLGA were distributed throughout the gastrointestinal (GI) tract (FIG. 4A). Generally, the fluorescence intensity from the PBA nanoparticles per gram of tissue was greater than that for the PLGA nanoparticles in the three tissues examined—stomach, large intestine, or small intestine. Out of all the PBA nanoparticles, the PUDCA nanoparticles showed the lowest retention in the stomach, indicating that these may be more suitable for oral drug delivery (FIG. 4A).

Figure 4B:
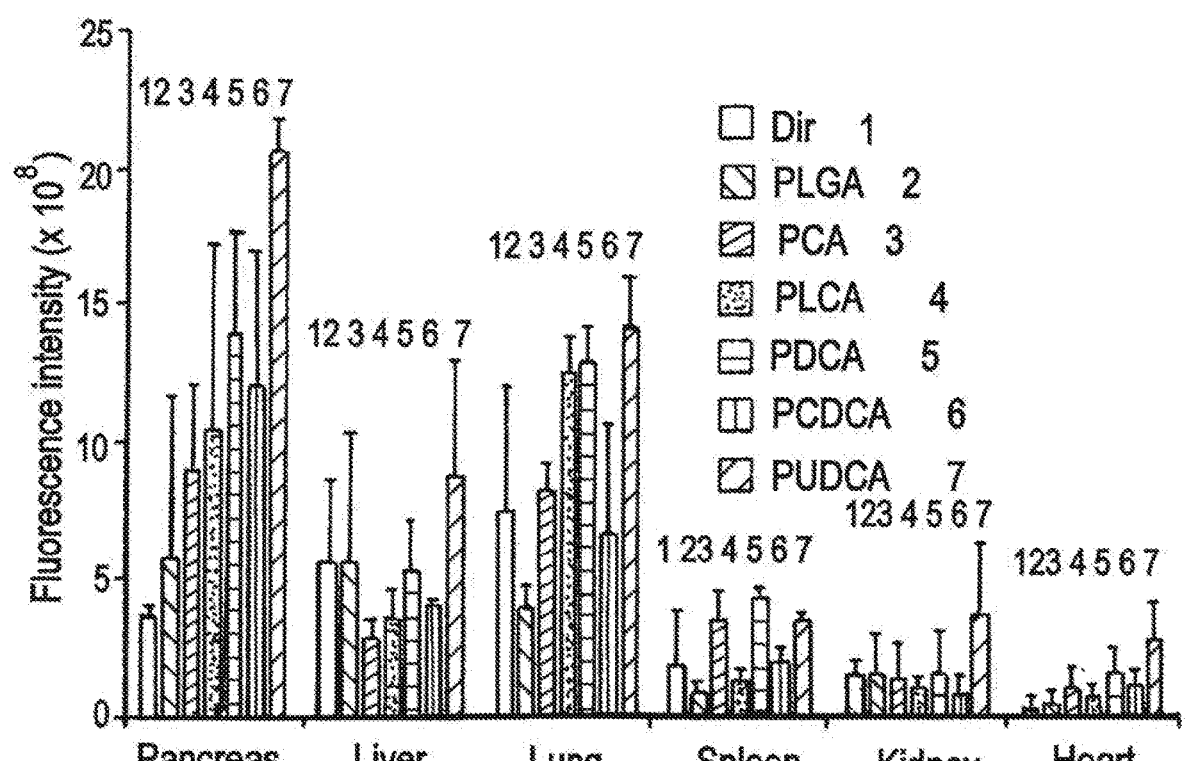
FIG. 4B is a bar graph showing fluorescence intensity of pancreas, liver, lung, spleen, kidney, and heart, four hours after oral administration of 5 mg/ml nanoparticles formed of PLGA (2), poly(cholic acid) (PCA, 3), poly(lithocholic acid) (PLCA, 4), poly(deoxycholic acid) (PDCA, 5), poly(cheno-deoxycholic acid) (PCDCA, 6), or poly(urso-deoxycholic acid) (PUDCA, 7), or free DiR dye (1).
Figure 4C:
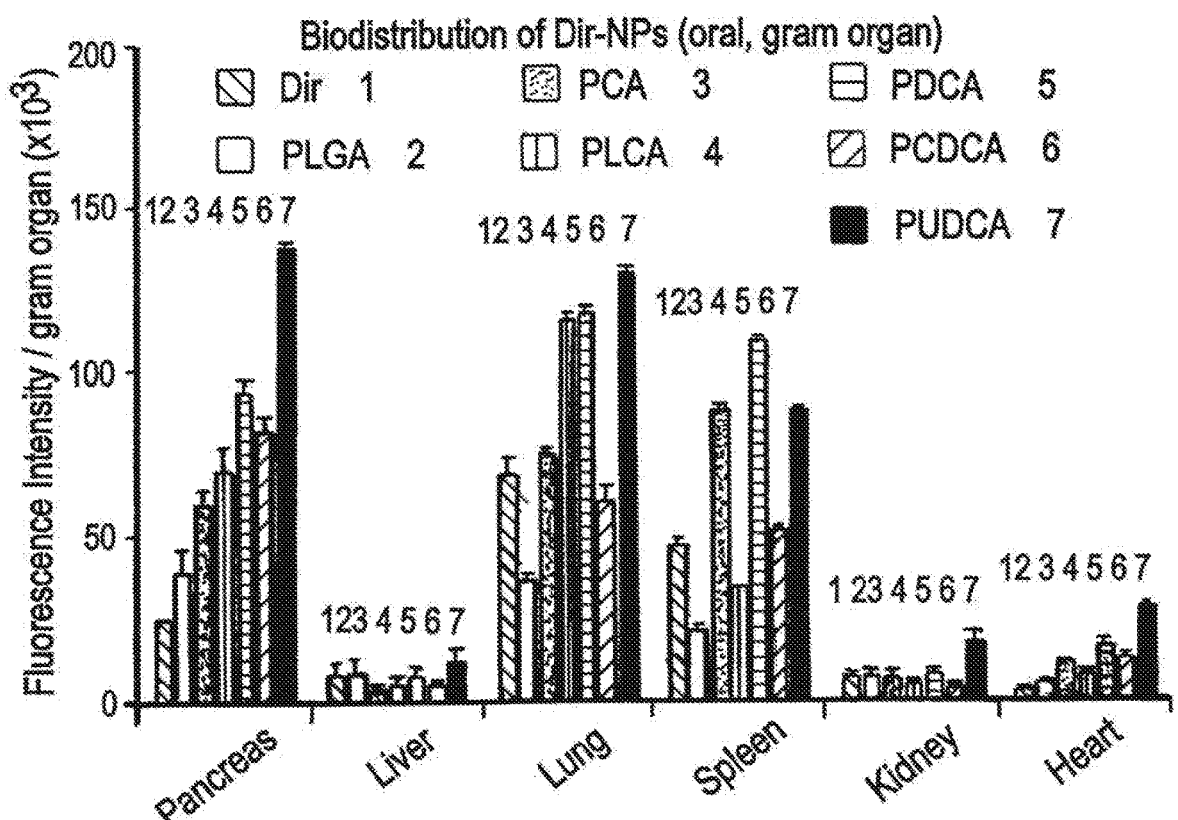
FIG. 4C is a bar graph of the data in FIG. 4B normalized per gram of pancreas, liver, lung, spleen, kidney, and heart.

Following oral delivery of the nanoparticles, the fluorescence from the nanoparticles was detected in the pancreas, liver, lung, spleen, kidney, and the heart (FIGS. 4B and 4C). When the fluorescence intensity was normalized per gram of tissue (FIG. 4C), the data revealed that PBA nanoparticles were more efficient at targeting the pancreas than were the PLGA nanoparticles. Also, the fluorescence intensity per gram of tissue from PUDCA nanoparticles was greater in all tissues when compared to that of the PLGA nanoparticles.

Figure 4D:
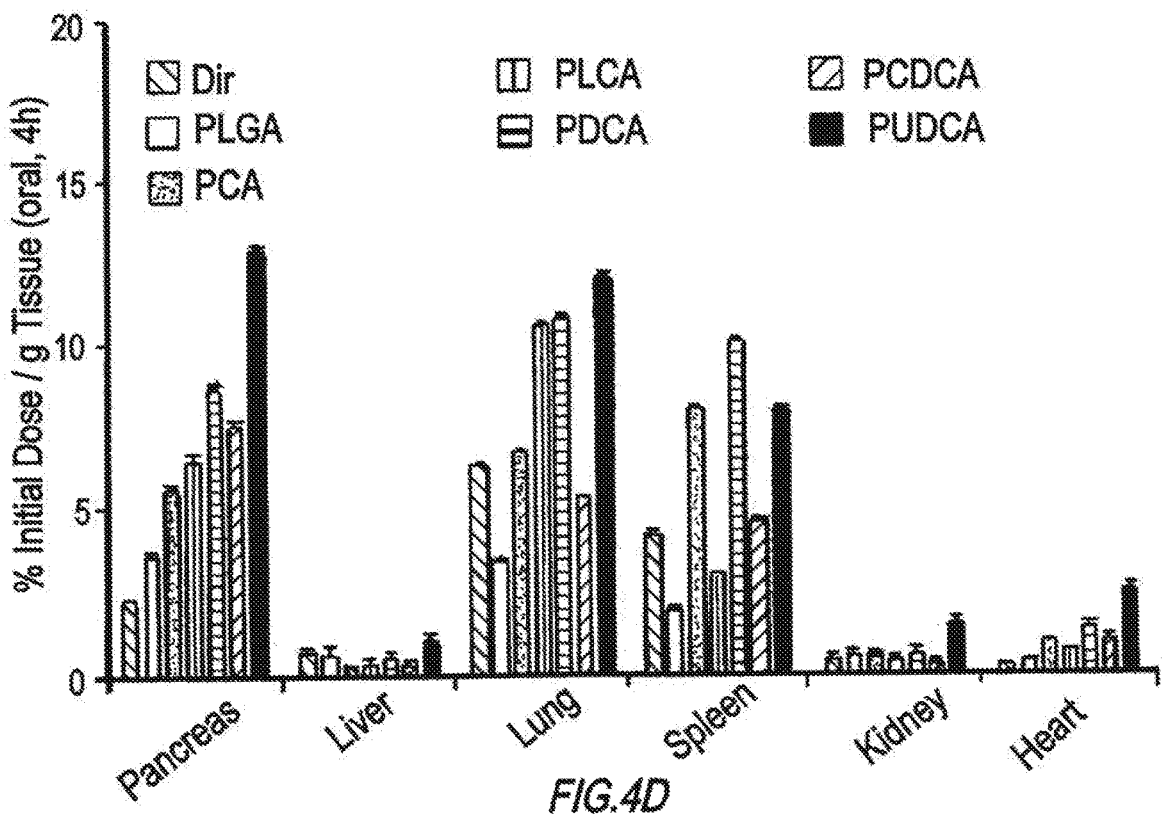
FIG. 4D is a bar graph showing biodistribution (% initial dose/g tissue) of PBA NPs in organs 4 hours after oral gavage.
Figure 4E:
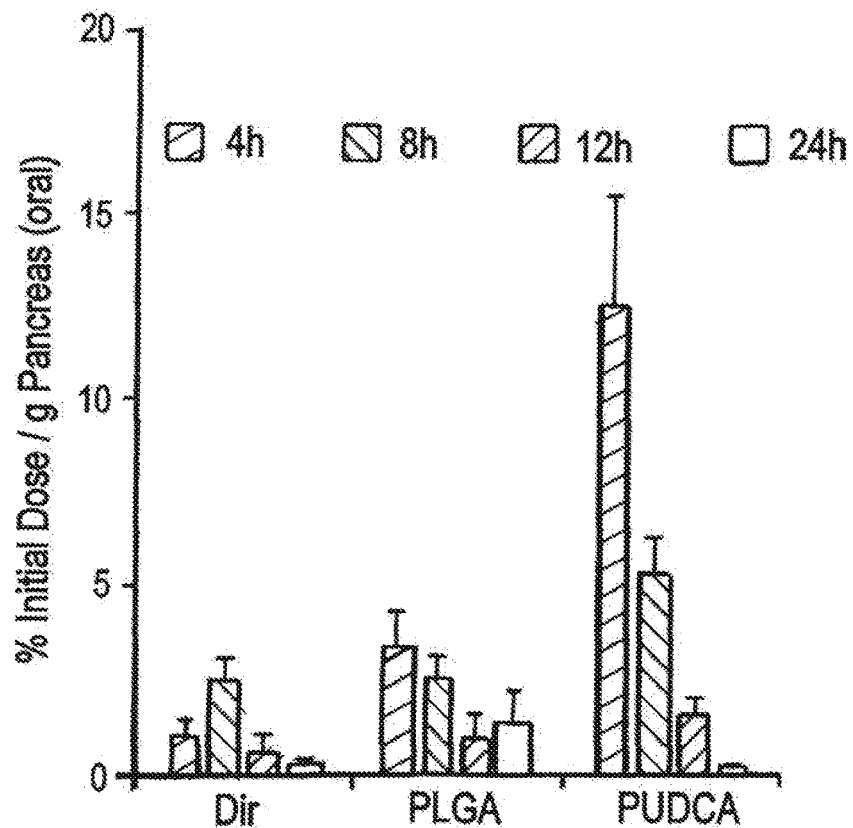
FIG. 4E is a bar graph showing uptake kinetics (% initial dose/g pancreas (oral)) of NP in pancreata depending on particle composition.
Figure 4F:
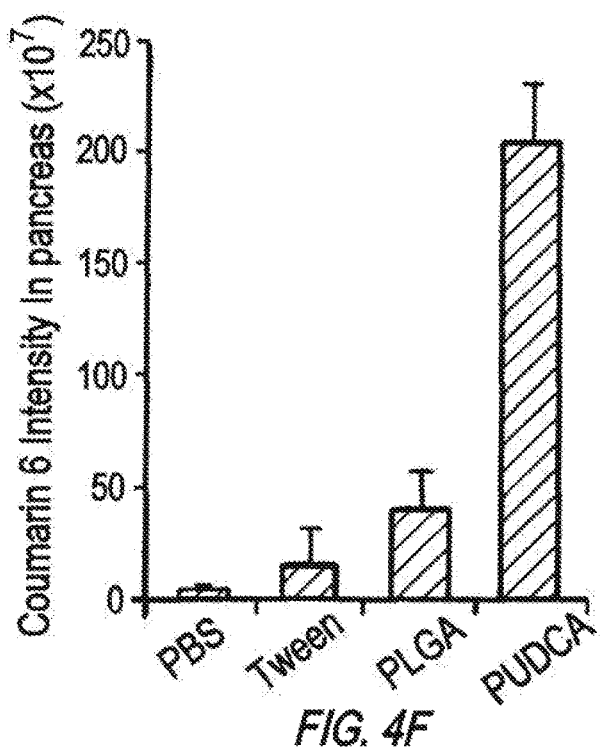
FIG. 4F is a bar graph showing pancreatic uptake of NP loaded with coumarin 6 (coumarin 6 intensity in pancreas ($\times 10^7$)).

A significantly higher NP uptake in the lungs, spleen, and especially pancreas was observed for PBA NPs, while their accumulation was relatively low in the liver, spleen, kidneys, and heart (FIGS. 4D, 4E and 4F). Among PBA NPs, PUDCA NPs showed the highest uptake in all organs, while the uptake of PCA NPs was the lowest. The pancreatic uptake could be related to physical parameters of the monomeric BAs, such as hydrophobicity and dissociation constant (pKa). UDCA is the most hydrophilic BA among BAs tested, while CA has a lower pKa value (4.98) than others assayed (5-6.5). It is known that the biological activity of BAs is closely related to their chemical properties, including the number and orientation of hydroxyl groups, because these parameters directly affect their hydrophobicity, pKa, water solubility, and micelle formation. However, the uptake levels of PBA NPs in organs were not linearly related to BA properties, including hydrophobicity (LCA<DCA<CDCA<CA<UDCA), number of hydroxyl groups (LCA<DCA=CDCA=UDCA<CA), or pKa (LCA<CA<UDCA<DCA<CDCA), likely because of the unpredictability of biological interactions and diversity of organ microenvironments. Control PLGA NPs showed relatively low uptake in the organs, and free Dir dye mostly accumulated in the lungs and spleen.

Example 5. PBA Nanoparticles Target the Pancreas Following Oral Gavage

Materials and Methods

Materials and methods were as described above.

Both the PUDCA and PLGA nanoparticles were loaded with about equal amount of DiR or Coumarin 6 (Table 1).

Histology

Pancreata from mice that received iron oxide-loaded PUDCA NPs (IO-PUDCA NPs) were fixed in 10% neutral buffered formalin for histological analysis by hematoxylin and eosin (H&E) and Prussian Blue stains. Stained sections were prepared by the Yale University Pathology Histology Service (New Haven, Conn., USA). Tissues were imaged on a Nikon TE-2000U microscope with a Nikon DS Fi 1 color camera and NIS Elements AR software (version 2.30).

Results

Figure 5A:
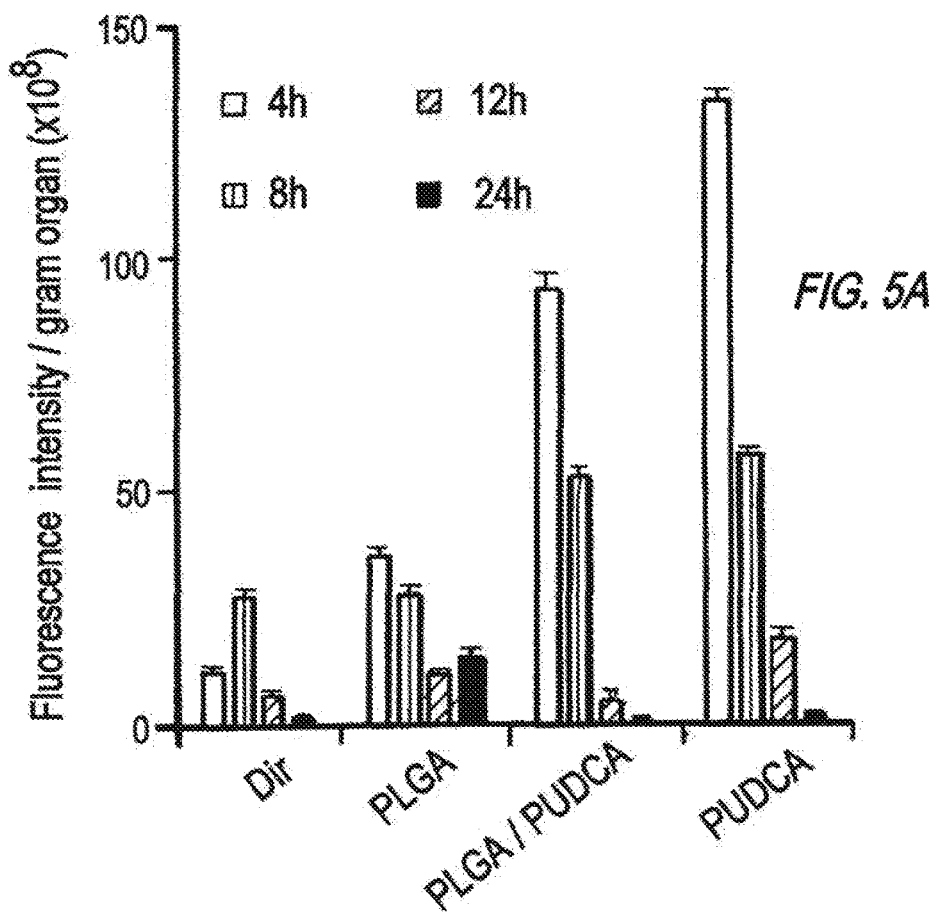
FIG. 5A is a bar graph showing fluorescence intensity per gram pancreas following 4, 8, 12, and 24 hours after oral gavage of free DiR dye, or DiR-loaded nanoparticles formed of PLGA, PLGA and PUDCA blend (50:50, or PUDCA alone.
Figure 5B:
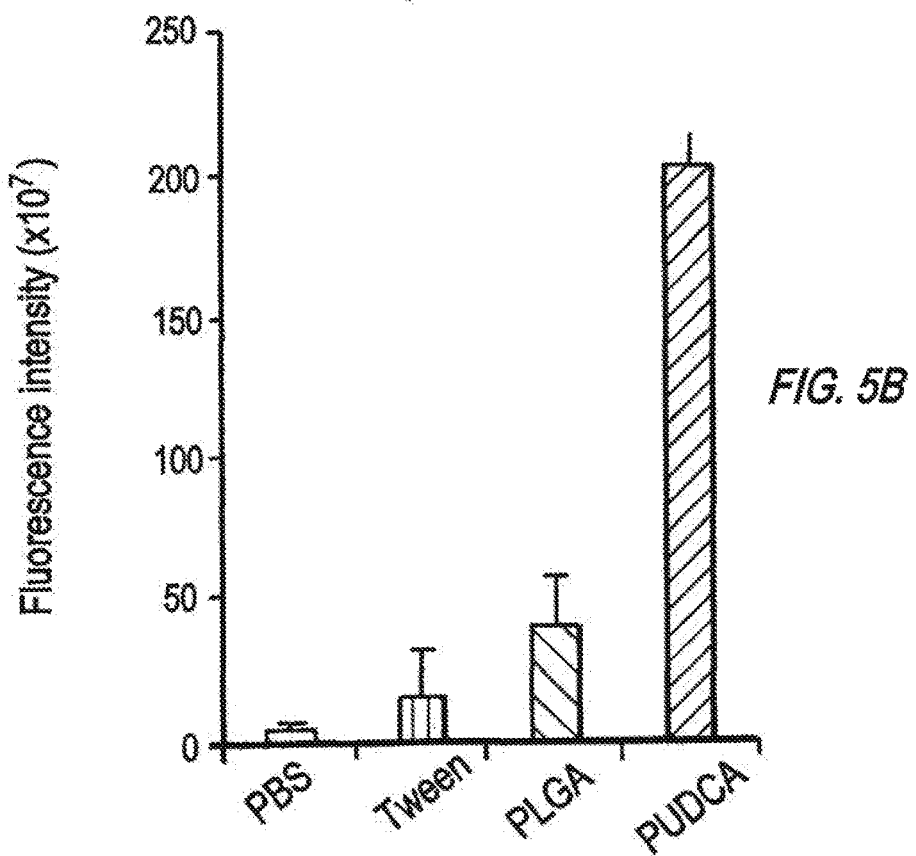
FIG. 5B is a bar graph showing fluorescence intensity of the following oral administration of coumarin 6 dye in PBS, in TWEEN®, or loaded in PLGA or PUDCA nanoparticles.

FIG. 5A demonstrates the uptake kinetics of PLGA, PLGA and PUDCA 50:50 blend, or PUDCA nanoparticles to the pancreas, and indicates that the uptake is dependent on nanoparticle composition. The pancreatic uptake of PUDCA nanoparticles was significantly greater than that for PLGA nanoparticles at 4, 8, and 12 hours post-gavage. This preferential uptake of PUDCA nanoparticles by the pancreas was dependent on the composition of the nanoparticles (FIGS. 5A and 5B). As indicated in FIGS. 5E and 5F, the biodistribution of PLGA and PUDCA nanoparticles was similar. FIG. 5E is % organ uptake of particles and 4B is actual quantitative data, which means absolute amount of PUDCA NP is higher in organs.

Figure 5C:
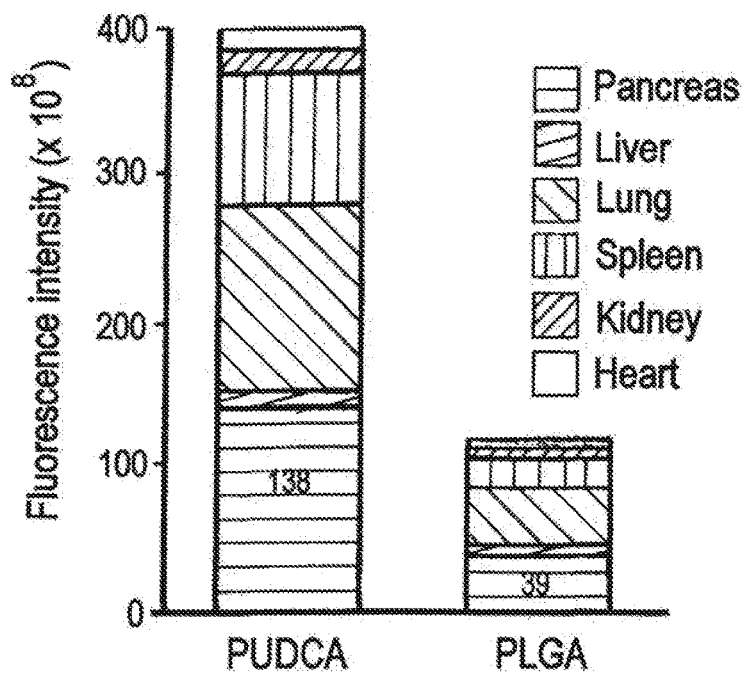
FIG. 5C is a stacked bar graph showing fluorescence intensity of pancreas, liver, lung, spleen, kidney, and heart four hours after oral administration of PLGA or PUDCA nanoparticles.

When normalized per gram of tissue, PUDCA nanoparticles produce greater fluorescence intensity in the respective organs, indicating that significantly greater amount of PUDCA nanoparticles reached these organs when compared to the amount of PLGA nanoparticles (FIGS. 5C and 4C).

Additionally, oral gavage of mice with PBS or superparamagnetic iron oxide (SPIO)-loaded PUDCA nanoparticles showed accumulation of the nanoparticles in the pancreatic cells when examined with Prussian Blue staining for iron oxide.

Figure 5D:
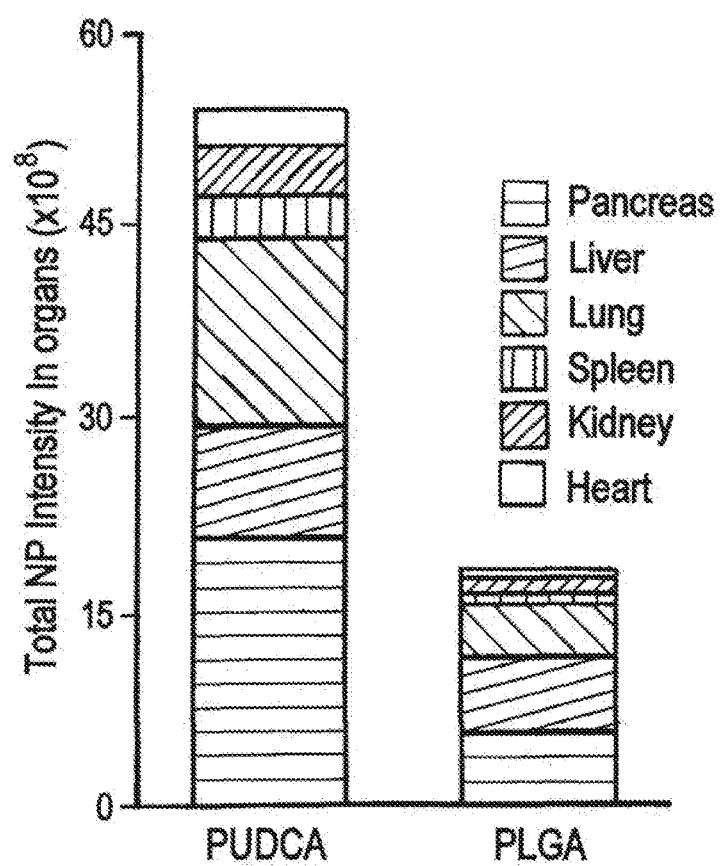
FIG. 5D shows cumulative NP uptake in organs after intestinal absorption.

The kinetics of pancreatic uptake and clearance of PBA and PLGA NPs were examined, finding that the peak uptake was 4 h after feeding, followed by particle clearance (FIG. 4E). Conversely, the pancreatic uptake of free dye was slower. To ensure that the remarkable pancreatic uptake was not a dye-dependent phenomenon, NPs were also formulated with coumarin 6, a dye that is much more hydrophobic than Dir. After varying the physical property of dyes, consistent pancreatic fluorescence readings confirmed that PUDCA NPs traffic to the pancreas to a significantly greater extent than PLGA NPs or suspended dye, regardless of dye properties (FIG. 4F). This pancreatic retention was further verified by dosing with PUDCA NPs encapsulating iron oxide (JO), and H&E staining confirmed that PBA NPs were nontoxic. Interestingly, the proportion of both PLGA and PUDCA NPs that traversed the intestines distributed in similar compartments; there were no significant differences between the biodistribution percentages of NPs that passed through the intestines (FIG. 5F). However, when mice were fed fluorescence-intensity-matched doses of PLGA or PUDCA NPs, substantially greater total fluorescence was recovered in the organs of mice that received PUDCA NPs (FIG. 5D), suggesting that more PUDCA NPs passed through the intestines and trafficked to organs.

Example 6. Trafficking of PBA Nanoparticles from the Gastrointestinal Track to Pancreas is Mediated Via Blood Transport Materials and Methods Each formulation (10 mg/ml, 100 uL injected (total=1 mg)) was also intravenously administered to the mice via tail vein injection (i.v.) to evaluate the biodistribution and fluorescence intensity of organs was measured after 2 h.

The PLGA, PLGA and PUDCA 50:50 blend, or PUDCA nanoparticles were studied for targeting the pancreas when injected intravenously, instead of administered via oral gavage.

Results

Figure 6A:
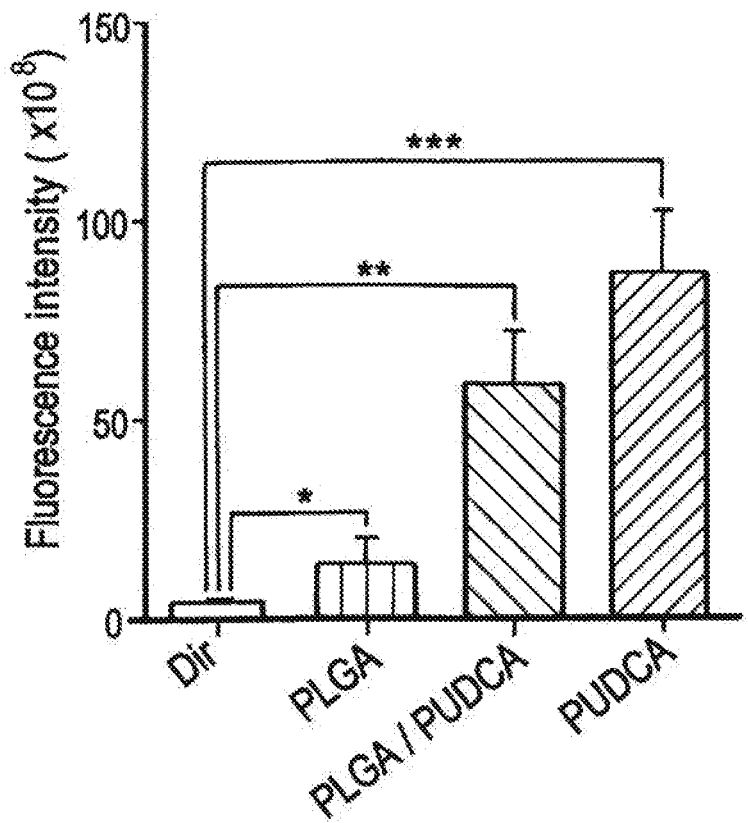
FIG. 6A is a bar graph showing fluorescence intensity of the pancreas two hours after intravenous injection of a free DiR dye, or DiR-loaded (5 mg/ml) nanoparticles formed of PLGA, PLGA and PUDCA blend (50:50), or PUDCA.
Figure 6B:
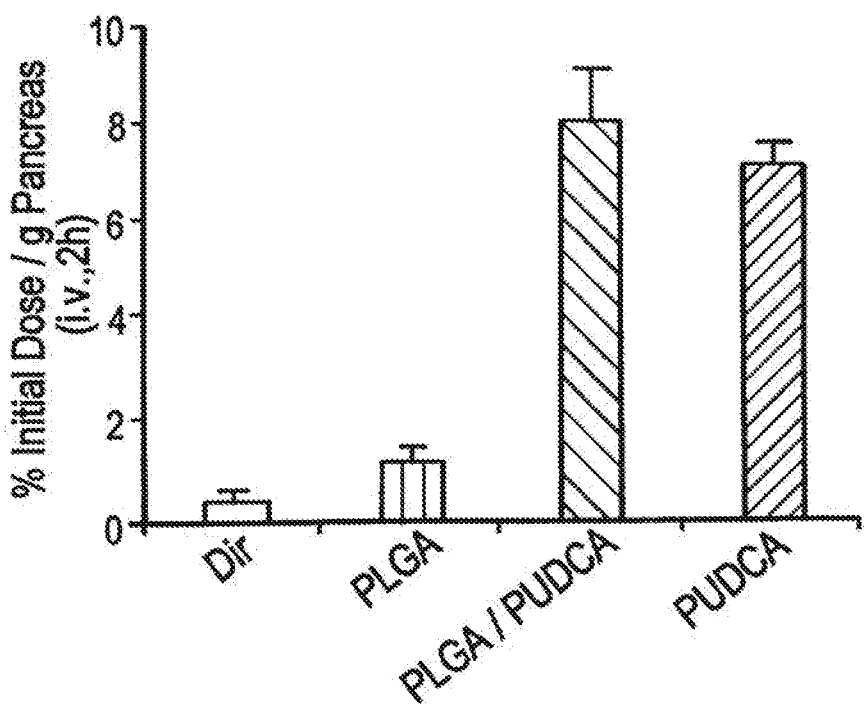
FIG. 6B is a bar graph showing pancreatic uptake of dye or NP 2 h after i.v. injection (% initial dose/g pancreas (i.v., 2 h)).

Two hours following intravenous injection the DiR-loaded PLGA, PLGA and PUDCA 50:50 blend, or PUDCA nanoparticles were retained in the pancreas, and again with greater retention of PUDCA nanoparticles than of the PLGA nanoparticles (FIGS. 6A and 6B). (PLGA: $13.0 \times 10^8$ (p=0.047), 50/50: $58.2 \times 10^8$ (p=0.002), PUDCA: $86.5 \times 10^8$ (p=0.0008)).

Figure 6C:
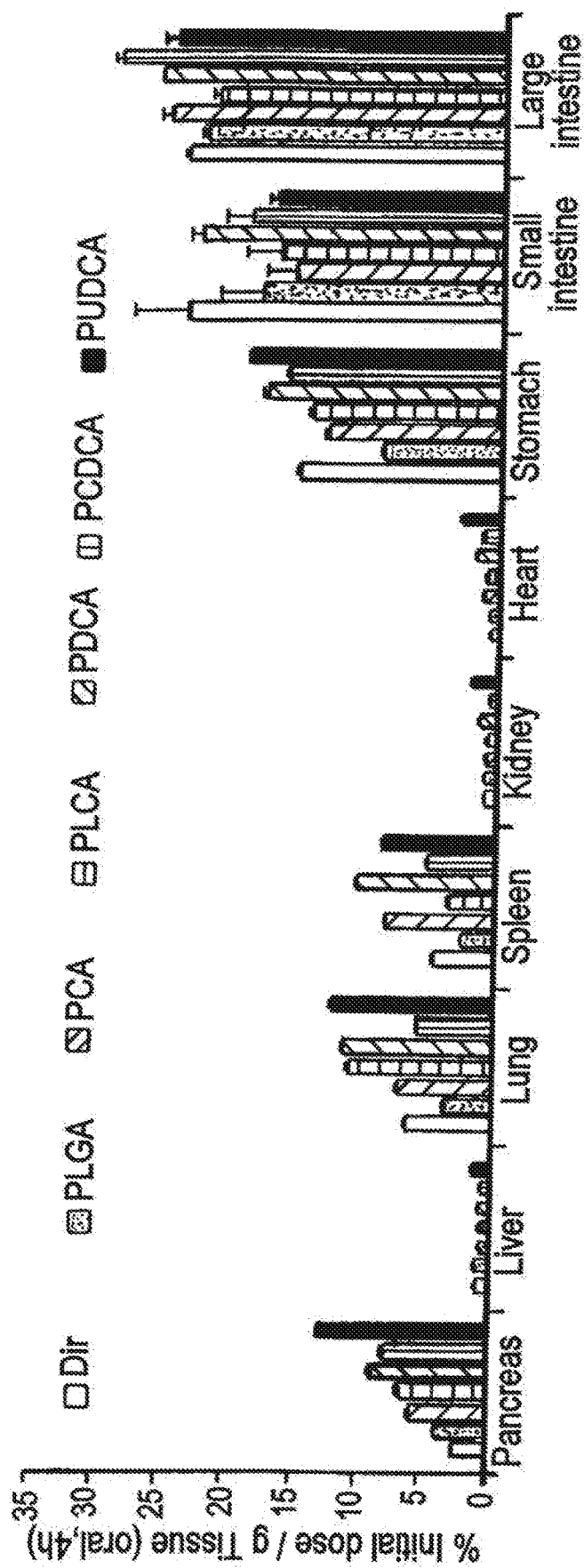
FIG. 6C is a bar graph showing uptake of DiR or NPs in organs after 4 h of oral administration. C57BL/6 mice were fasted for 4 h and treated with Dir-encapsulating NPs by oral gavage (500 mg/kg, 250 µL). Free Dir and PLGA NPs served as controls. Mice were sacrificed at time points of 4 h post-gavage, and the organs were scanned ex vivo to measure fluorescence intensity. Higher NP uptake in the pancreas, lungs, spleen, stomach, and intestines was observed, while their accumulation was relatively low in the spleen, kidneys, and heart.
Figure 6D:
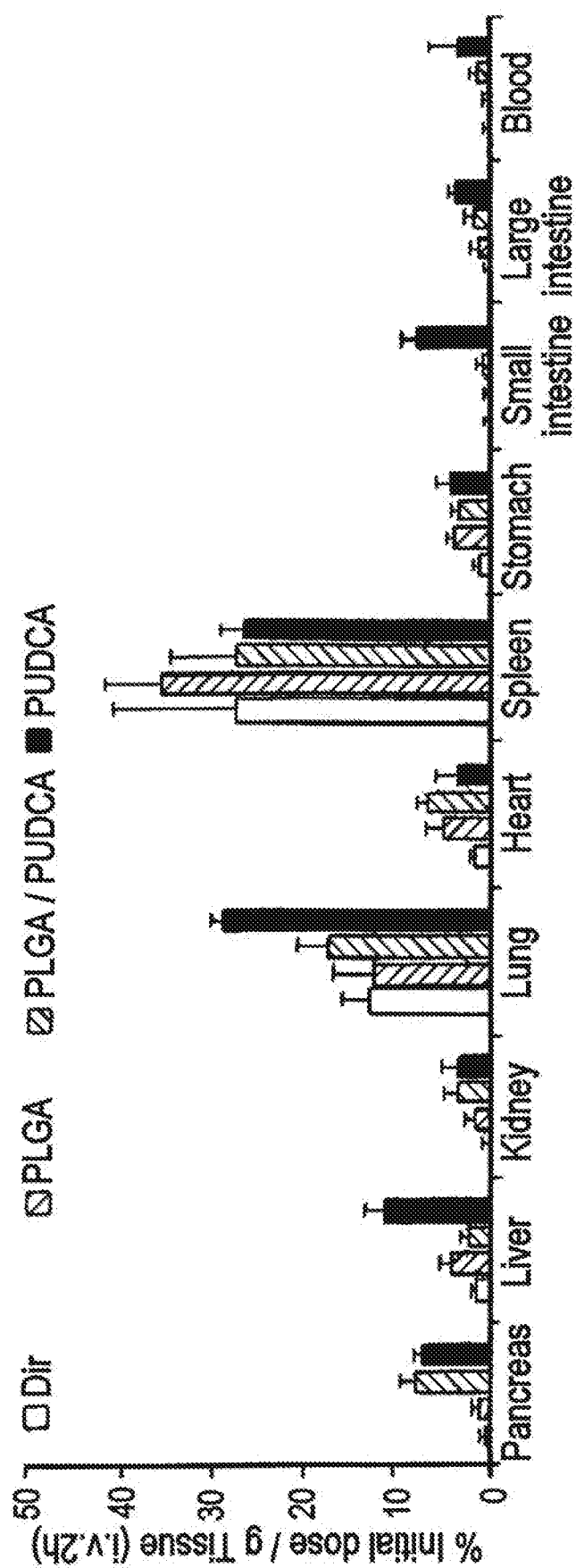
FIG. 6D is a bar graph showing uptake of DiR or NPs in organs after 2 h of i.v. administration. PUDCA, PLGA, and the composite NPs (100 mg/kg, 50 µL) were also intravenously administered (i.v.) to mice via tail vein injection to compare with free Dir. Organs and blood were collected and measured after 2 h. A significant accumulation of PUDCA and composite NPs in the pancreas was observed.

The enhanced organ trafficking of PUDCA NPs was completely explained by superior stomach protection and intestinal permeation by intravenously (i.v.) injecting NPs (PLGA, PUDCA, or composite) to bypass the digestive tract. After i.v. administration, the uptake of PUDCA NP in the pancreas (FIG. 6B), liver, and lungs remained higher than PLGA or composite NPs (FIGS. 6C and 6D). This result indicated that another driving factor of high PUDCA NP oral bioavailability was present in circulation. The macrophages were chosen for further studies because these cells often govern the fate of particles in vivo, playing key roles in internalizing, shuttling, and clearing particles in the bloodstream.

Figure 6E:
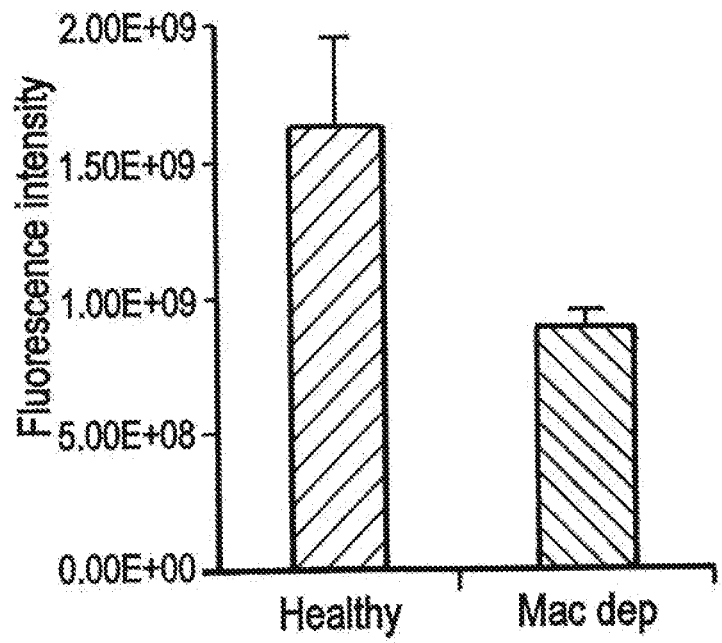
FIG. 6E is a bar graph showing fluorescence intensity of pancreases obtained from healthy or macrophage-depleted mice two hours after intravenous administration of DiR-loaded PUDCA.
Figure 6F:
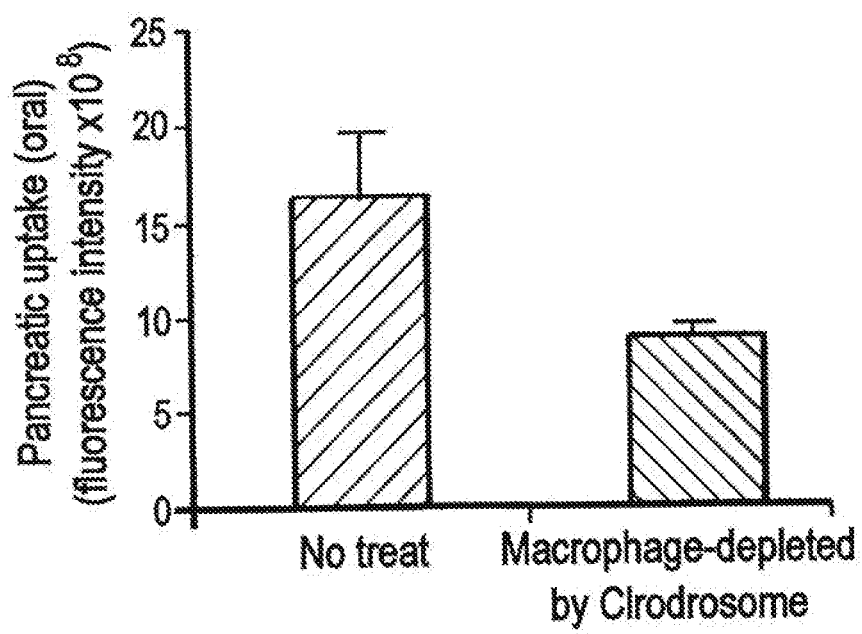
FIG. 6F is a bar graph showing pancreatic uptake of PUDCA NPs in healthy or macrophage depleted mice.

Since PUDCA nanoparticles are preferentially taken up by bone marrow macrophages (FIG. 2I), it was tested whether intravenous injection of the DiR-loaded PUDCA nanoparticles into healthy or macrophage-depleted mice would affect the pancreatic retention of the nanoparticles. As demonstrated in FIGS. 6E and 6F, the pancreases of macrophage-depleted mice retained significantly lower amount of the DiR-loaded PUDCA nanoparticles than did the pancreases of the healthy mice, as indicated by the significantly lower fluorescence intensity (FIGS. 6E and 6F). (Healthy: $2.72 \times 10^8$, mac-dep: $1.45 \times 10^8$, p=0.017).

Figure 6G:
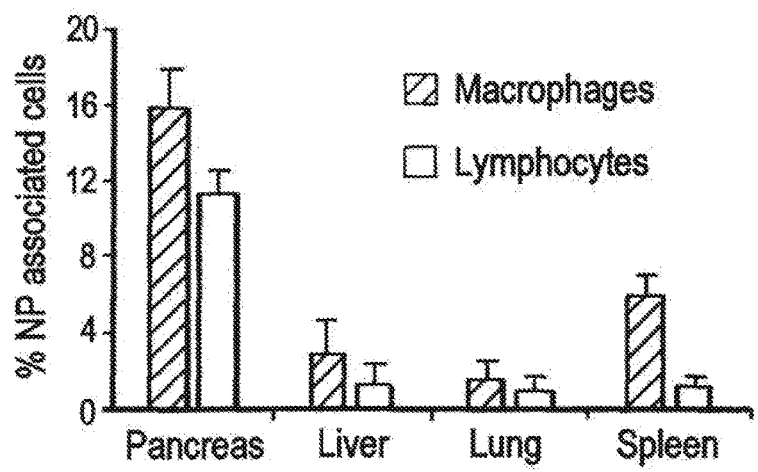
FIG. 6G is a bar graph showing percentage of macrophages and lymphocytes containing NPs in pancreas, liver, lung, and spleen.
Figure 6H:
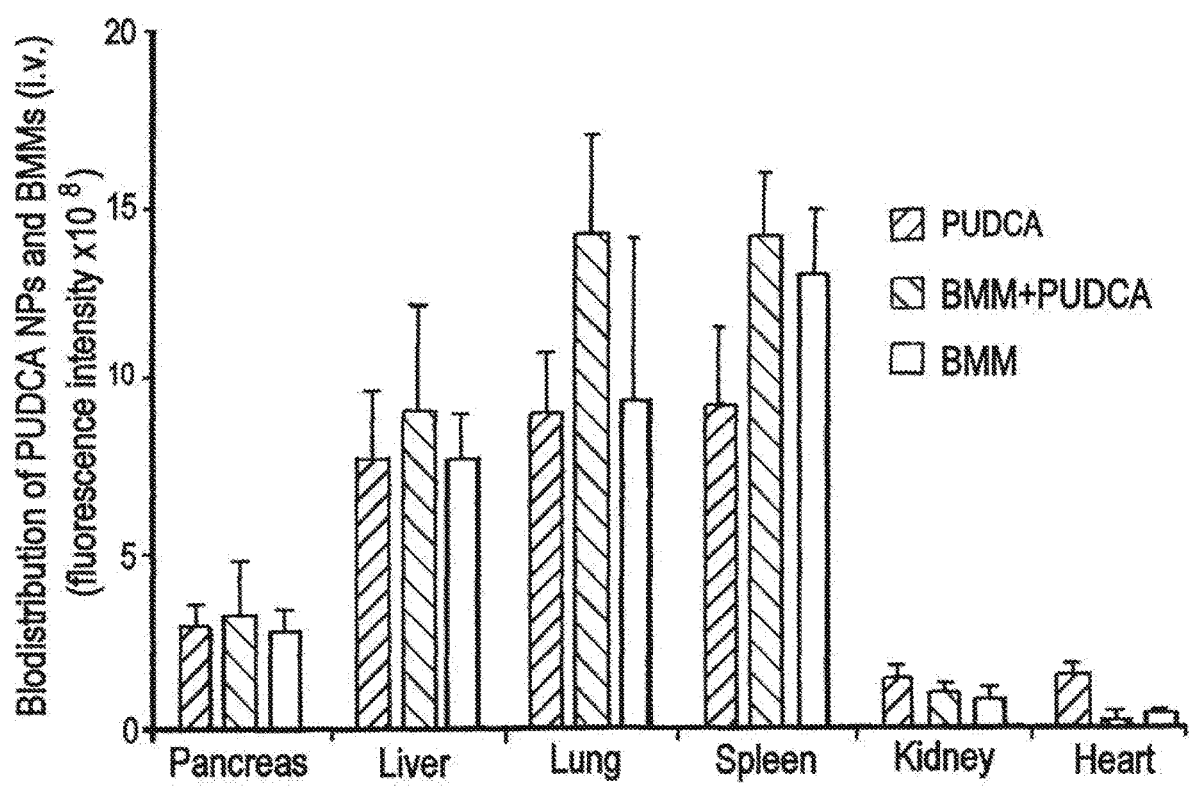
FIG. 6H is a bar graph showing biodistirbution of bone marrow-derived macrophages (BMMs) containing PUDCA NPs. BMMs were incubated with PUDCA NPs to load macrophages ex vivo and washed to remove NPs that were non-specifically bound to cells. BMMs containing PUDCA NPs ($1 \times 10^6$) were labeled with Dir (10 µM) for 15 min and injected intravenously via tail vein to compare biodistribution with PUDCA NPs alone (100 mg/kg, 50 µL) and BMMs alone ($1 \times 10^6$). The biodistribution results among these groups were not statistically significant, indicating that the interaction between macrophages and PUDCA NPs did not redirect these cells to any specific organs.
Figure 6I:
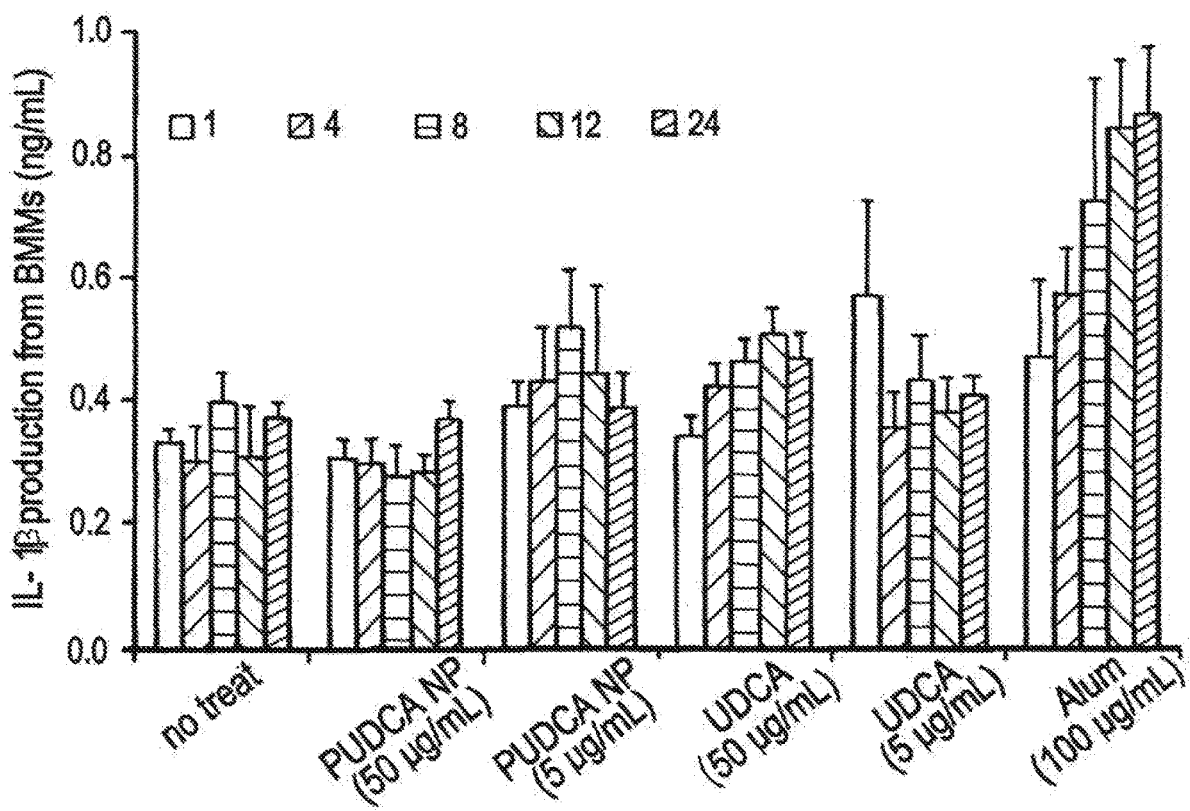
FIG. 6I is a bar graph showing proinflammatory cytokine (IL-1β) production (ng/ml) from BMMs incubated with various concentrations of PUDCA, UDCA, or Alum.

When mice were depleted of macrophages by clodronate liposomes, the pancreatic uptake of PUDCA NPs significantly decreased (FIG. 6F), demonstrating that macrophages indeed played critical roles in depositing PUDCA NPs in the pancreas. Flow cytometry analysis confirmed that 16% of macrophages (11% of total lymphocytes) were associated with PUDCA NPs in the pancreas (FIG. 6G). Next, the bone-marrow derived macrophages (BMMs) were incubated with PUDCA NPs to load macrophages ex vivo, and compared the biodistribution of PUDCA NPs after adoptive transfer of loaded macrophages with direct injection of PUDCA NPs or naïve BMMs. The biodistribution results among these groups were not statistically significant, indicating that the interactions between macrophages and PUDCA NPs did not redirect these cells to any specific organs (FIG. 6H). It was also found that PUDCA NPs did not induce upregulation of proinflammatory cytokine (IL-1β) from BMMs (FIG. 6I).

This data indicated that transport of orally delivered PUDCA nanoparticles could be trafficked to the pancreas via blood either in free form, or engulfed in macrophages.

Figure 6J:
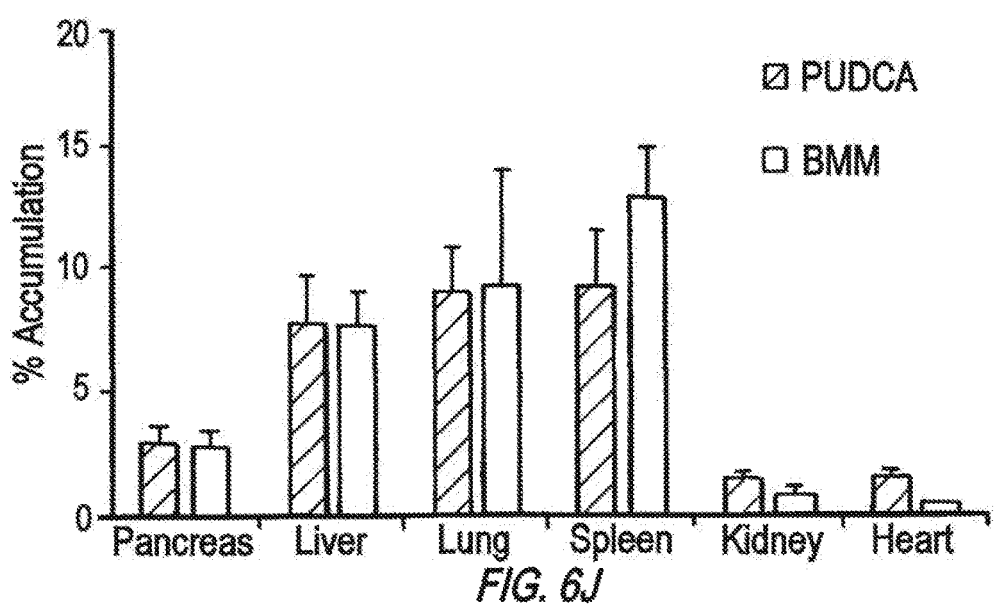
FIG. 6J is a bar graph showing percent accumulation of PUDCA or BMM in organs.

To confirm that macrophages play a role in trafficking and retention of the PBA nanoparticles, percent accumulation of the PUDCA nanoparticles or macrophages in various organs was examined. DiR-loaded PUDCA nanoparticles and DiR-labeled macrophages were intravenously injected into wild type mice, after two hours the mice were sacrificed, and the percentage accumulation examined in pancreas, lung, liver, spleen, kidney and heart. Results are presented in FIG. 6J, and demonstrate that the percentage accumulation of PUDCA nanoparticles and that of macrophages was similar in all organs examined.

Figure 6K:
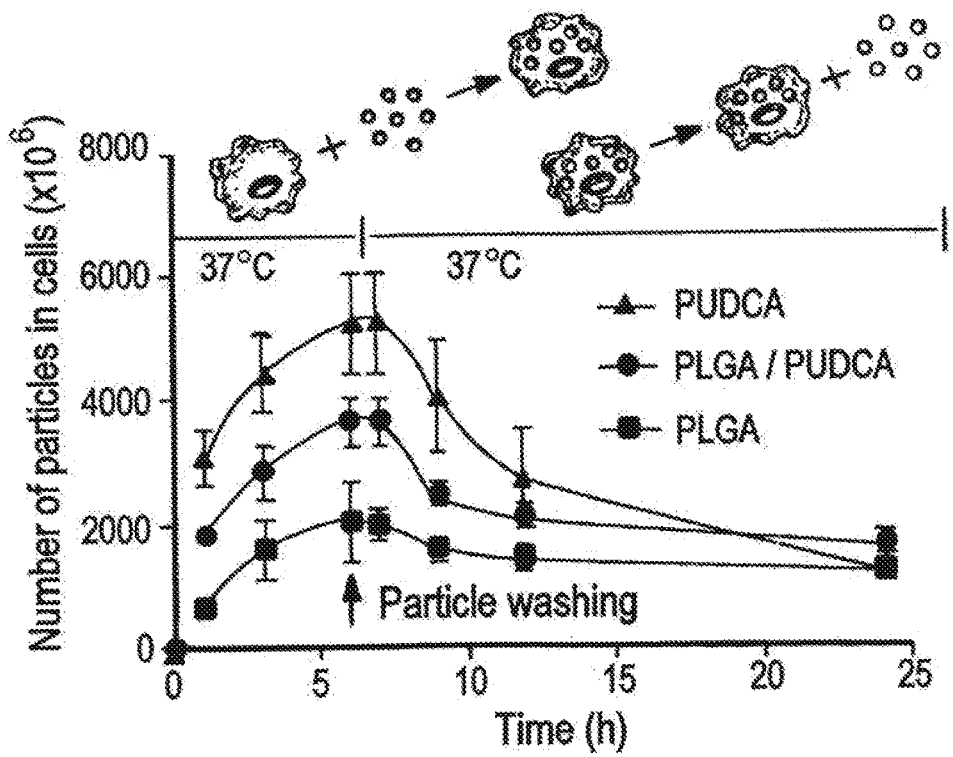
FIG. 6K is a line graph showing the change in the number of particles in cells (×10⁶) over time (h) before and after particle washing when maintained at 37° C. following washing.
Figure 6L:
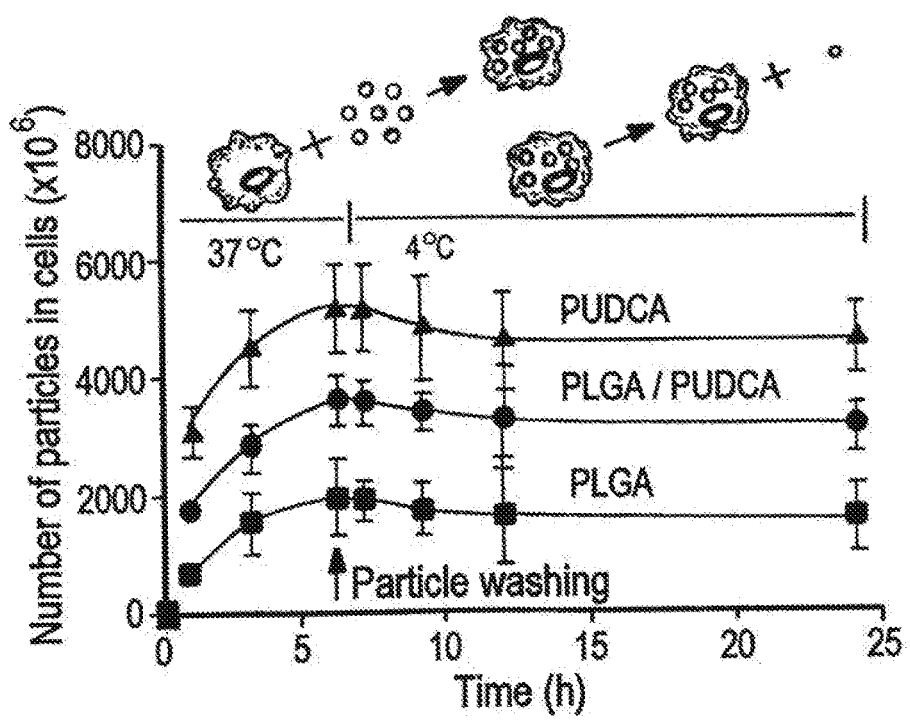
FIG. 6L is a line graph showing the change in the number of particles in cells (×10⁶) over time (h) before and after particle washing when maintained at 4° C. following washing.
Figure 6M:
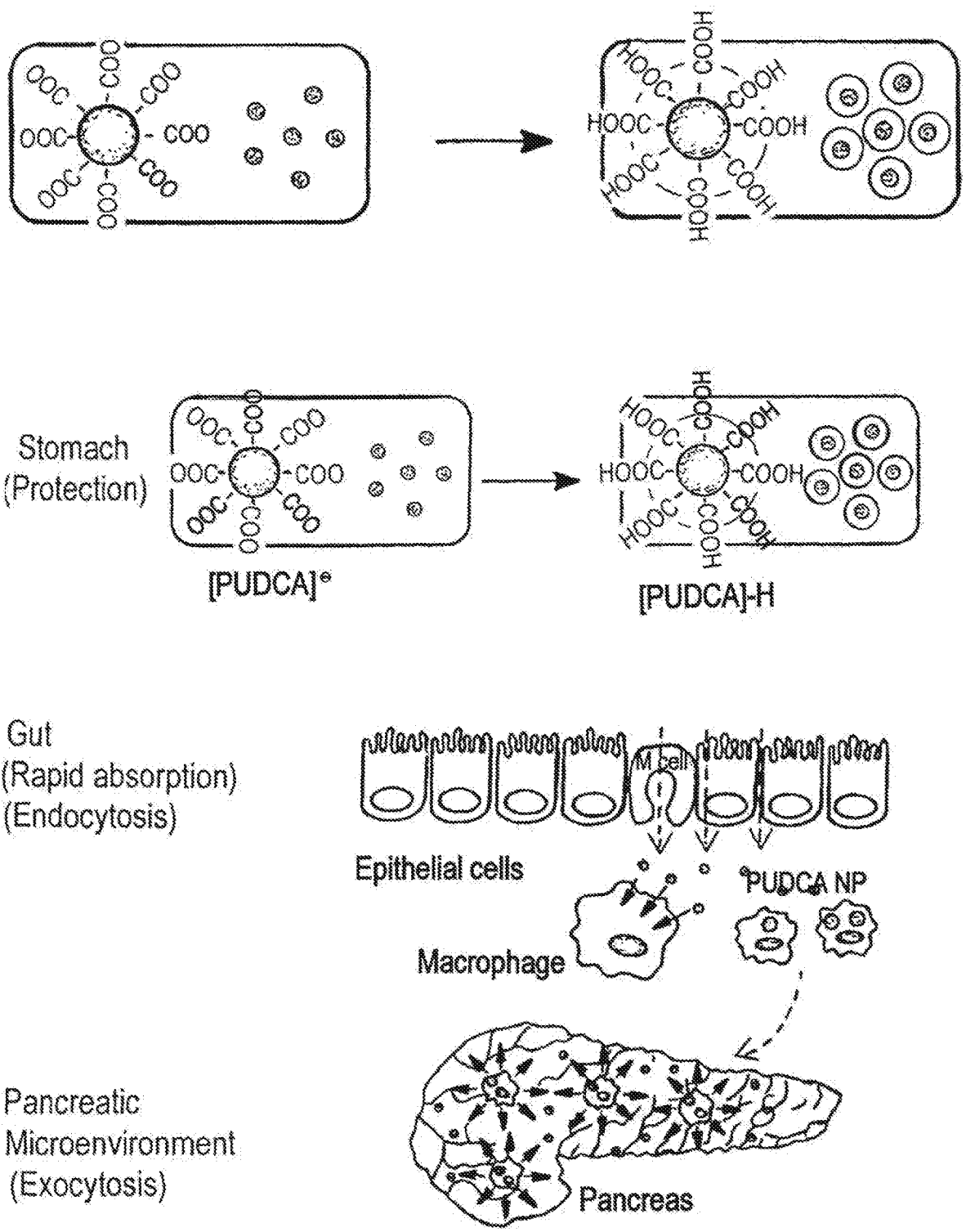
FIG. 6M is a schematic diagram of PUDCA NPs reaching the pancreas following oral administration.

The kinetics of uptake and release of PUDCA, PLGA/PUDCA, and PLGA NPs by macrophage are presented in FIGS. 6K and 6L. A schematic diagram showing PUDCA NPs reaching the pancreas following oral administration is presented in FIG. 6M.

Example 7. Prevention of Type 1 Diabetes with Rapamycin-Loaded PBA Nanoparticles Materials and Methods NOD mice (NOD/ShiLtJ, Jackson Laboratory, 7 weeks old) were intraperitoneally injected with cyclophosphamide (CY, 200 mg/Kg) to induce T1D. After 24 h, the mice were then orally gavaged with rapamycin-loaded NPs (rapa-NPs, 40 mg/mL, 250 4, 0.5 g/Kg, 1 or 2 doses, 0.1 mg rapalmg of NP) and monitored for glycosuria. Two readings (Two days apart) higher than 250 mg/dL were taken as an indication onset of T1D. Dir-NPs were used to image the diabetic pancreases. $CD44_+$ of CD8 cells and CD4+CD25+ Foxp3+ Tregs were acquired using a flow cytometer following CY and NP treatments. Pancreatic draining lymph nodes were harvested and processed using a 40 µm cell strainer to isolate splenocytes. Cell surface markers were stained with fluorescent antibodies for CD8 (PerCP-Cy5.5; 2 ug/ml), CD4 (Pacific Blue; 2 µgimp, CD44 (Alexa Fluor-700; 2 ug/ml), and CD25 (FITC; 1 µg/ml) by incubating for 30 minutes at 4° C. Cells were then fixed, permeabilized, and stained for Foxp3 (PE; 5 ug/ml) using the Foxp3 staining kit from eBiosciences and following the manufacturer's recommended protocol. After the final wash, samples were immediately run on a BD LSR-II multicolor flow cytometer to quantify the percentage of CD44+, CD8+, as well as CD4+ CD25+Foxp3+ T reg cells. Post-analysis was performed using FloJo FACS analysis software.

Results

Figure 7A:
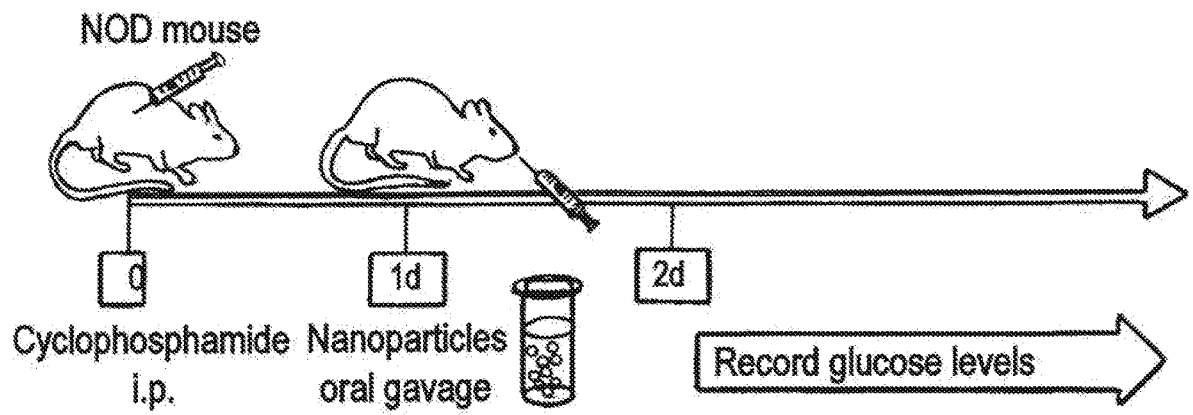
FIG. 7A is a diagram showing a treatment regimen for preventing Type 1 Diabetes in NOD mice.
Figure 7B:
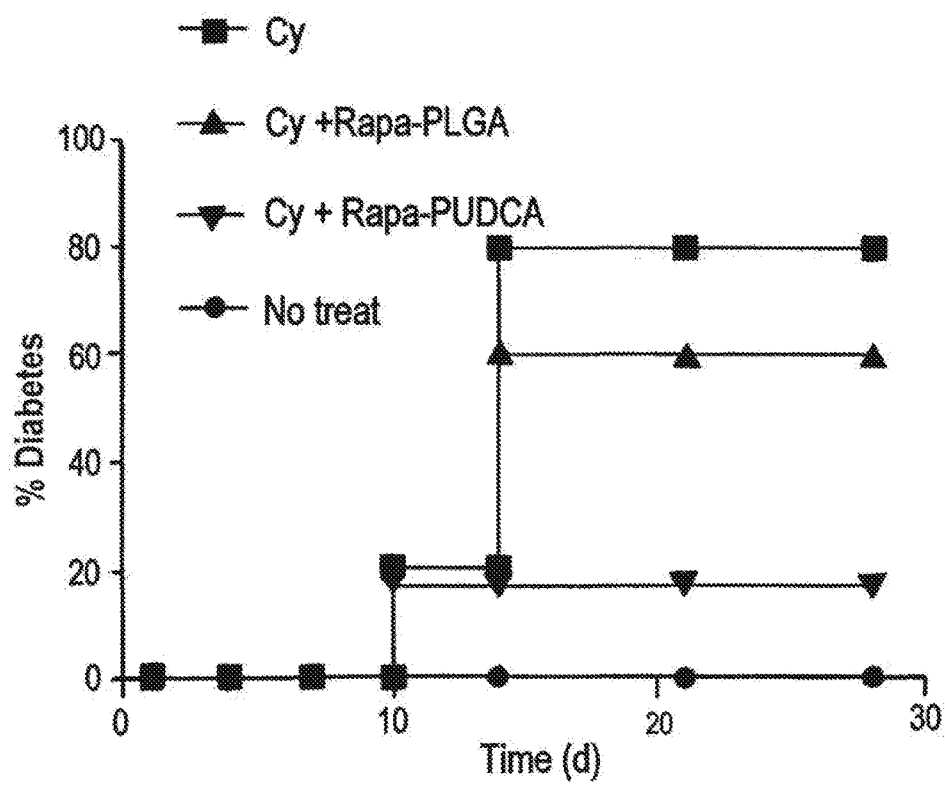
FIG. 7B is a line graph showing percent of mice developing diabetes over time (days) in four different groups: NOD mice without treatment, NOD mice administered CY alone, NOD mice administered CY and rapamycin-PLGA nanoparticles, or NOD mice administered CY and rapamycin-PUDCA nanoparticles.
Figure 7C:
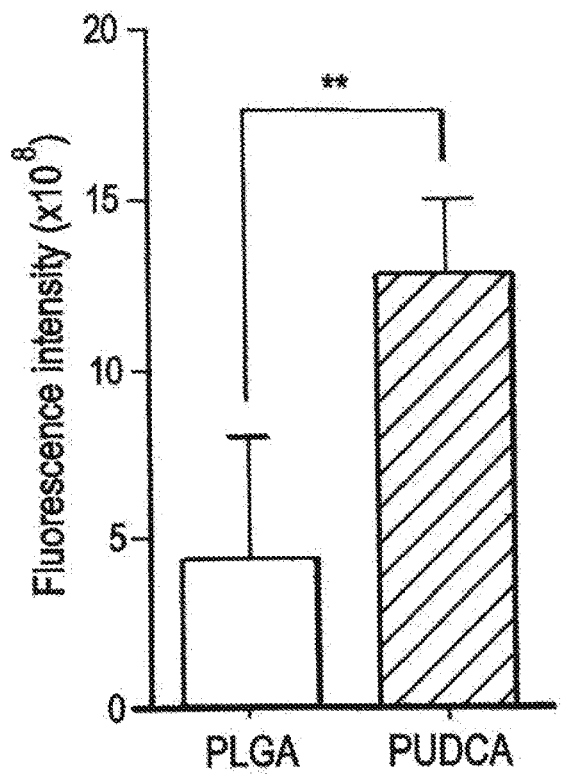
FIG. 7C is a bar graph showing fluorescence intensity of pancreases isolated from the diabetic mice treated with rapamycin-PLGA or rapamycin-PUDCA.

FIGS. 7A-7C demonstrate that rapamycin-loaded PUDCA nanoparticles, but not rapamycin-loaded PLGA nanoparticles, prevent development of T1D in NOD mice. Type 1 Diabetes (T1D) was induced in NOD mice by intraperitoneal injection of cyclophosphamide (CY), leading to rapid synchronous onset of T1D (FIG. 7A). After one day following CY injection, the mice received oral gavage of rapamycin-loaded PLGA or PUDCA nanoparticles once, or twice. Blood glucose levels were measured starting from day two after CY injection.

FIG. 7B demonstrates that while 80% of mice treated with CY developed diabetes after 12 d, disease was partially attenuated by PUDCA NPs encapsulating rapamycin for 30 d. PLGA-rapamycin treatment was, however, not sufficient to suppress disease progression, as 60% of mice succumbed to T1D (FIG. 7B). As indicated in FIG. 7B, only about 20% of the mice receiving rapamycin-PUDCA developed T1D versus about 60% when treated with rapamycin-PLGA. This effect could be attributed to a greater retention of the rapamycin-loaded PUDCA nanoparticles in the inflammatory pancreases of the T1D mice, versus that of rapamycin-loaded PLGA nanoparticles (FIG. 7C).

Figure 7D:
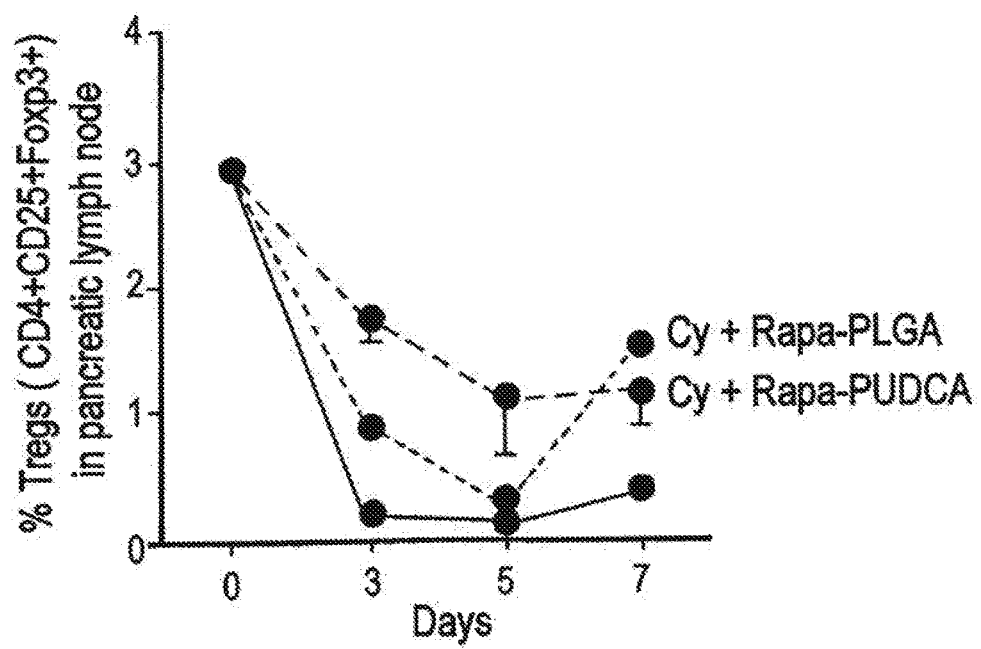
FIG. 7D shows CD4+Foxp3+CD25+ Treg cells in the population of lymphocytes (FIG. 8D) at 0, 3, 5, and 7 days following CY administration (Untreated), or CY and rapamycin-PUDCA nanoparticle administration given orally once or twice as indicated in the Figure.

Also, the percentage of effector memory CD44+CD8 T cells and CD25+FoxP3+CD4 regulatory T cells (Treg) was examined before or 3, 5, and 7 days following cyclophosphamide injection. The percentage of regulatory T cells (Tregs), evaluated by expression of CD4+CD25+FoxP3+, was tracked in the draining lymph nodes, after treatment, over several days (FIG. 7D). While PLGA NP treatment decreased the Treg depletion induced by CY compared to no treatment, PUDCA NP treatment enabled more significant suppression of Treg depletion. Also, rapamycin-PUDCA nanoparticle treatment dampened the loss of Tregs, as the percentage of CD25+FoxP3+CD4 Treg in the lymphocyte population was not reduced as severely as in the untreated mice.

Example 8. Reversal of Type 1 Diabetes with Insulin-Loaded PBA Nanoparticles Materials and Methods NOD mice were housed for approximately 2 month to allow them to develop T1D spontaneously. When two random tail vein blood glucose measurements (two days apart) were higher than 200 mg/dL, the mice were orally treated with free insulin or insulin-loaded NPs (insulin-NPs) every day for a week and monitored for glycosuria and body weight. Plasma and pancreas insulin concentrations were determined with the Mouse Ultrasensitive Insulin ELISA 4, 8, and 24 h after the oral gavage. Seven days post Ins-NP treatments, pancreatic lymph nodes were harvested and analyzed by flow cytometry to quantify the percentage of CD44+CD8+ cells as well as CD4+CD25+Foxp3+ Tregs.

Cell Isolation and Culture.

Long bones and spleens were harvested from mice (C57BL/6 or Rag2/OT-II) post-cervical dislocation. Bone marrow eluted from long bones, or spleens, were macerated with 1 mL plastic syringes in RPMI-1640 (Life Technologies) media supplemented with 10% FBS (Atlanta Biologicals). RBCs were lysed using Tris-NH4Cl buffer. Bone-marrow derived macrophages (BMMs) were cultured in RPMI media with macrophage colony-stimulating factor (M-CSF, 10 ng/mL) at 37° C. in a humidified atmosphere with 5% CO2. BMDCs were generated using a conventional expansion protocol in which 5☐105 cells/mL were plated in RPMI supplemented with 20 ng/mL GM-CSF and cultured for 5 days. On day 5, non-adherent cells were collected and replated in GM-CSF media for an additional 2 days. Non-adherent cells were harvested, and CD11c expression confirmed DC phenotype. T cells were purified from splenocyte populations using CD4+ negative selection kits (EasySep).

Functional Characterization of Cellular Responses to PUDCA

Purified CD4+ T cells (C57BL/6, 1×10$^5$ cells/well, 96 well plate) were stimulated with anti-CD28 and anti-CD3 antibodies, and incubated with 50 pg/mL or 5 µg/mL PUDCA NPs. On day 3, cell proliferation was measured using CFSE labeling, and cytokine secretion in supernatants was quantified by ELISA assays. For antigen-specific studies, OVA-specific CD4+ cells were used in OTII co-culture assays. BMDCs (2.5·10$^4$) were pretreated with PUDCA NPs for 24 h, washed, and then stimulated with LPS (10 ng/mL) and ovalbumin (20 µg/mL) for 24 h, followed by co-culture with OTII CD4+ T cells (5·10$^4$) for 3 d. Cell proliferation and cytokine production were then quantified.

Flow Cytometry

The CD44+ populations of CD8+ cells and the number of CD4+CD25+Foxp3+ Tregs were determined by flow cytometry following NP treatments. Pancreatic lymph nodes were harvested and processed using a 40 µm cell strainer. Cell surface markers were stained with fluorescent antibodies for CD8 (PerCP-Cy5.5), CD4 (Pacific Blue), CD44 (Alexa Fluor-700), and CD25 (FITC) by incubating for 30 minutes at 4° C. Cells were then fixed, permeabilized, and stained for Foxp3 (PE) using the Foxp3 staining kit from eBiosciences and following the manufacturer's recommended protocol. After the final wash, samples were immediately run on a BD LSR-II multicolor flow cytometer. Data analysis was performed using FlowJo analysis software.

CD11c-F4/80+ macrophages were characterized by flow cytometry following treatment with 1,1'-dioctadecyl-3,3,3', 3'-tetramethylindodicarbocyanine perchlorate (DiD) loaded PUDCA NPs for uptake studies. Spleens, pancreatic lymph nodes, lungs, and livers were harvested and processed by homogenization using a 40 µm cell strainer and syringe plunger. Cell surface markers were stained with fluorescent antibodies for F4/80 (Alexa Fluor-700), and CD11c (PE-Cy7) by incubating for 30 minutes at 4° C. After 3 washes with FACS buffer (2% FBS in PBS), samples were immediately run on an Attune NxT multicolor flow cytometer (Life Technologies, Guilford, USA).

Following NP treatments of cultured BMDCs, cells were isolated, washed using FACS buffer (2% FBS in PBS), and then stained using primary Abs diluted in FACS buffer for 30 minutes at 4° C. Antibodies used in these studies included CD11c (eFluor450), MHC Class I (APC), MHC Class II (PerCP-Efluor710), CD40 (FITC), and CD86 (PE). Samples were then fixed in 2% paraformaldehyde and run on an LSRII flow cytometer. 10,000 events were counted for each sample and then analyzed using FlowJo software. All samples were initially gated on forward and side scatter gates followed by gating on CD11c+ singlets. These cellular events were then assessed for expression of MHC Class I, MHC Class II, CD40, and CD86 surface markers using geometric mean fluorescent intensities for statistical analyses.

Results

Mice with established diabetes (verified by consistent blood glucose readings of over 200 mg/dL) were fed fluorescent PLGA or PUDCA NPs. After 4 h, a greater amount of fluorescence was detected in mice given PUDCA, and in contrast to PLGA-treated mice, fluorescence was detected 24 h later, showing high retention of PUDCA NPs.

Figure 8A:
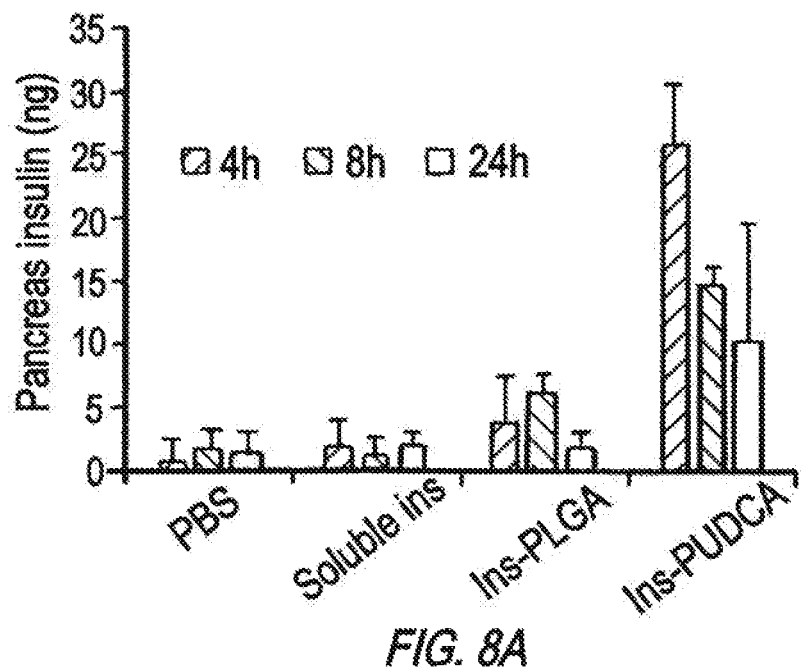
FIG. 8A is a bar graph showing the amount of insulin (ng) in pancreases of T1D mice receiving PBS, soluble insulin, or insulin-loaded PLGA or PUDCA nanoparticles via oral administration (gavage) at 4, 8, and 24 hours (h) following administration.
Figure 8B:
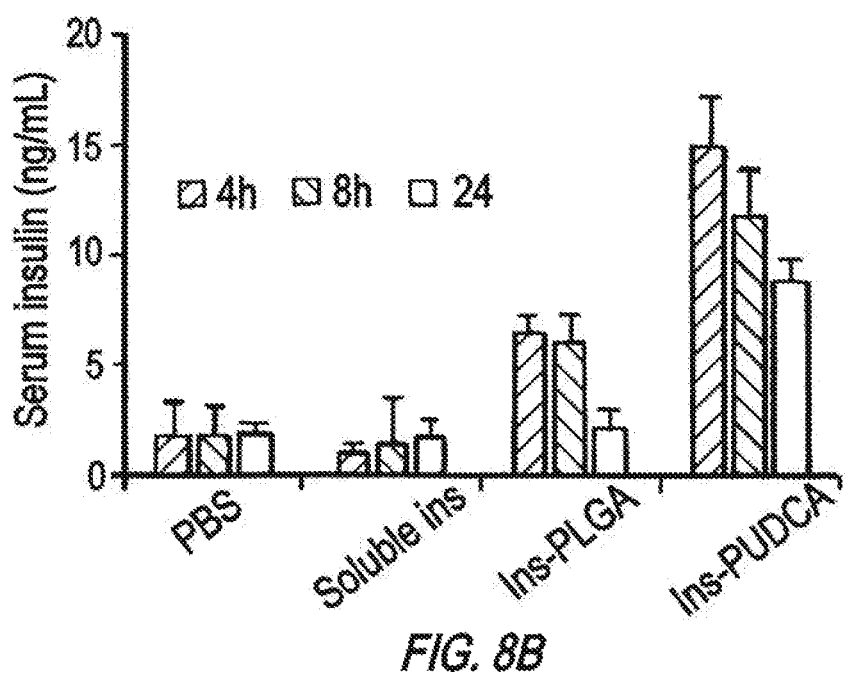
FIG. 8B is a bar graph showing insulin concentration (ng/ml) in the serum of T1D mice receiving PBS, soluble insulin, or insulin-loaded PLGA or PUDCA nanoparticles via oral administration (gavage) at 4, 8, and 24 hours (h) following administration.
Figure 8C:
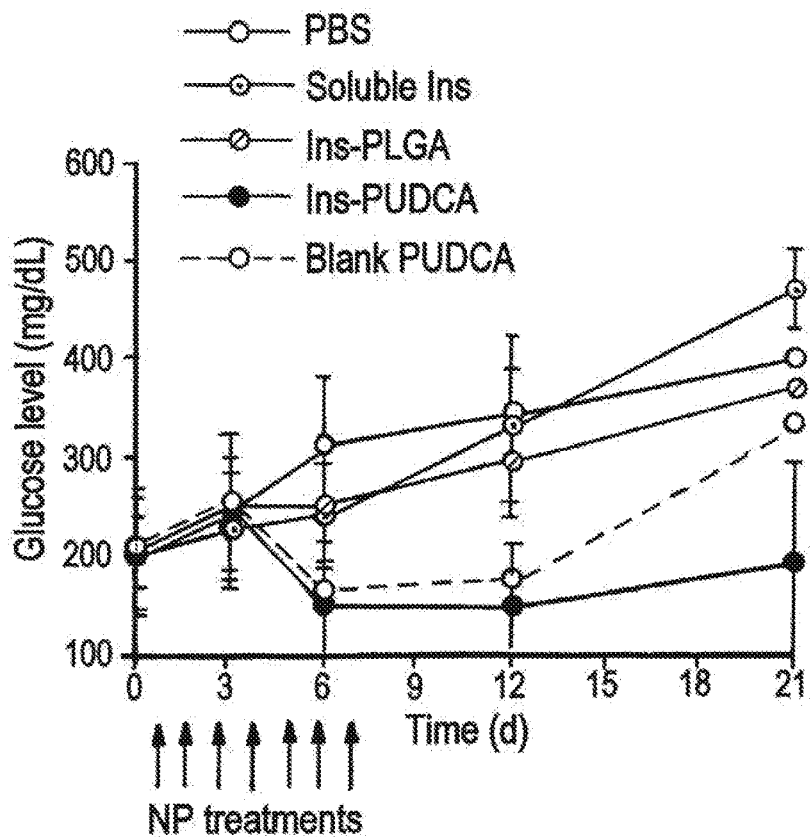
FIG. 8C is a line graph showing changes in blood glucose level (mg/dL) over time (days, d) in T1D mice receiving PBS, soluble insulin, or insulin-loaded PLGA or PUDCA nanoparticles via oral administration (gavage.
Figure 8D:
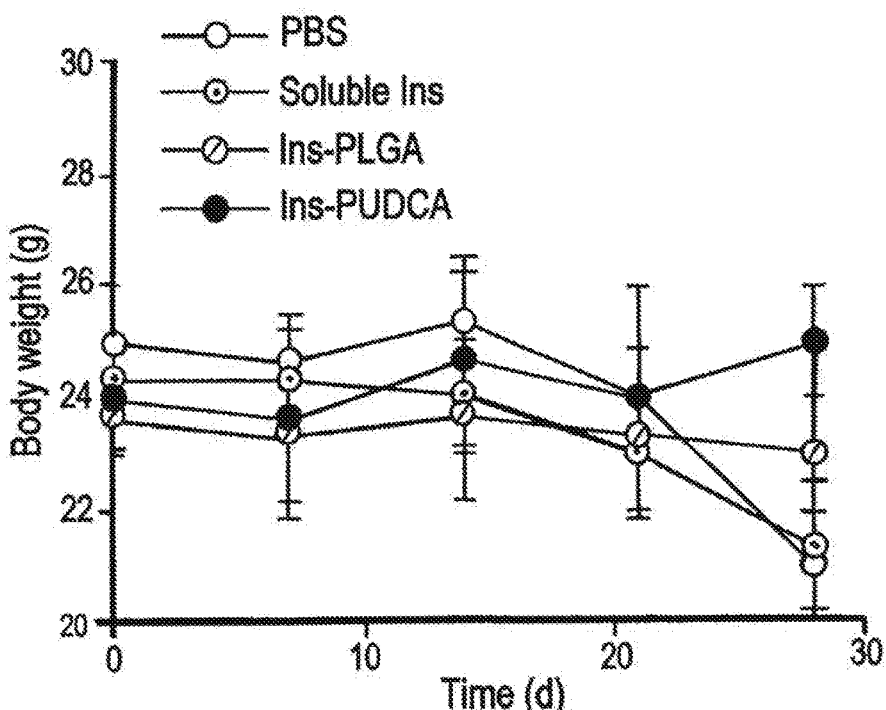
FIG. 8D is a line graph showing change in body weight (grams, g) over time (days, d) of T1D mice receiving PBS, soluble insulin, or insulin-loaded PLGA or PUDCA nanoparticles via oral administration (gavage).
Figure 8E:
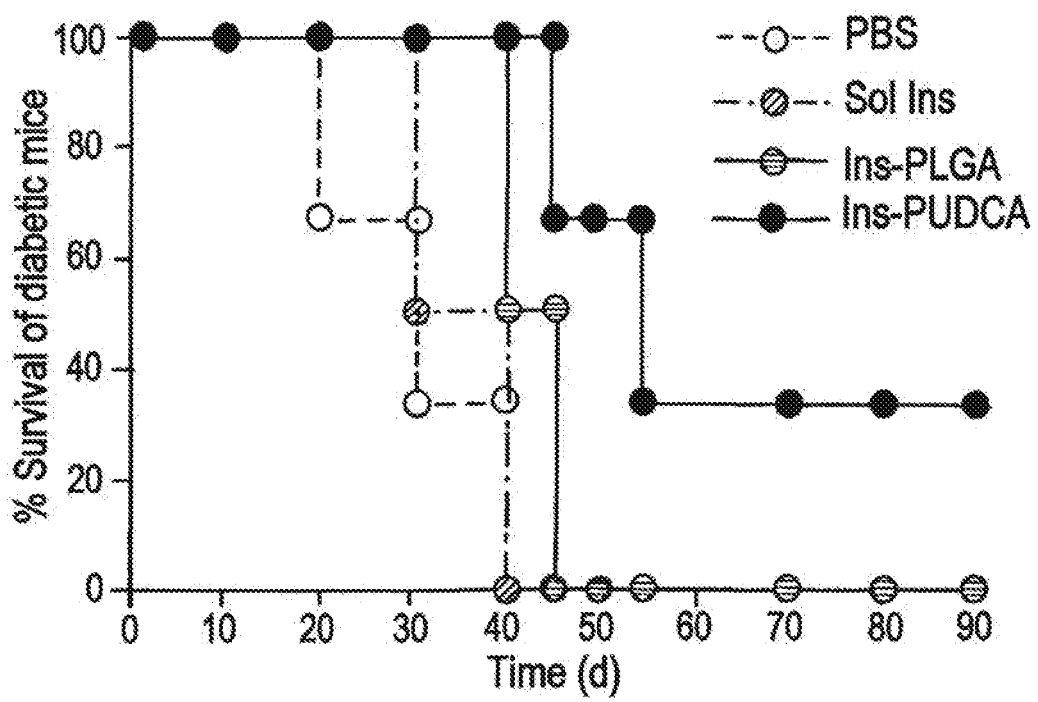
FIG. 8E is a Kaplan-Meier survival curve showing percent survival (%) over time (days, d) of T1D mice receiving PBS, soluble insulin, or insulin-loaded PLGA or PUDCA nanoparticles via oral administration (gavage).

FIG. 8C demonstrates that oral gavage of insulin-loaded PUDCA nanoparticles, but not insulin-loaded PLGA nanoparticles (a total of seven doses administered daily for the first week of diabetes), sustains blood sugar levels for at least 21 days and reverses T1D. During the treatment period, the body weight of the mice remained largely unchanged (FIG. 8D). Significantly, insulin-loaded PUDCA nanoparticles doubled the expected survival of the T1D mice (FIG. 8E).

The beneficial therapeutic effect of the pancreas-targeting insulin-loaded PUDCA nanoparticles could be explained by significantly greater insulin levels in the pancreases of mice treated with insulin-loaded PUDCA nanoparticles, when compared to that of mice treated with insulin-loaded PLGA nanoparticles, at 4 and 8 hours following oral administration of nanoparticles (FIG. 8A). (PLGA 4h: 4.10 ng, PLGA 8h: 6.41 ng, PUDCA 4h: 25.9 ng, PUDCA 8h: 14.9 ng, p<0.001, n=5) Similarly, the concentration of insulin in serum of the mice treated with insulin-loaded PUDCA nanoparticles was significantly greater when compared to that of mice treated with insulin-loaded PLGA nanoparticles, at 4 and 8 hours following oral administration of nanoparticles (FIG. 8B) (PLGA 4h: 6.55 ng/mL, PLGA 8h: 6.14 ng/mL, PUDCA 4h: 14.94 ng/mL, PUDCA 8h: 11.80 ng/mL, p<0.01, n=5).

Figure 9A:
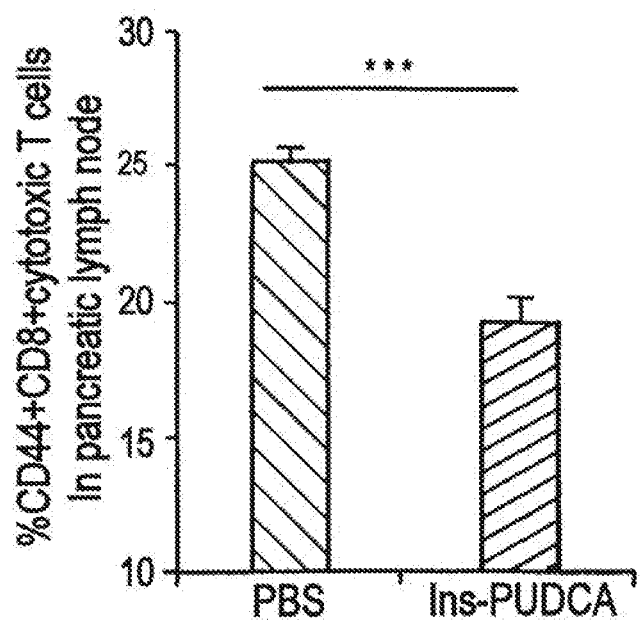
FIG. 9A is bar graph showing the percentage of activated (CD44+) CD8 cells and FIG. 9B showing the percentage of CD4+CD25+Foxp3+ Tregs in pancreatic lymph nodes after treatments FIG. 9C showing IFN-γ production of CD4+ T cells, directly treated with PUDCA NPs, and stimulated with anti-CD3 and anti-CD28, FIG. 9D response of OT-II CD4+ T-cells after coculture with PUDCA-treated DCs that were stimulated by LPS and ovalbumin.
Figure 9B:
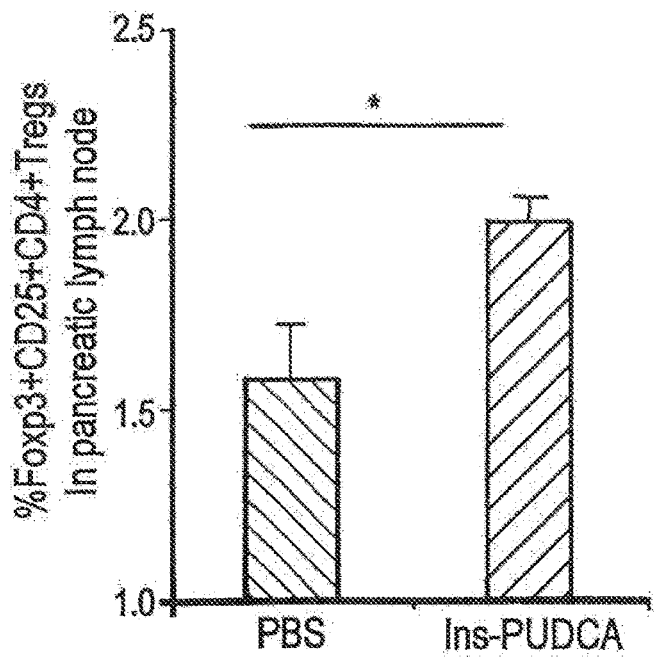
FIG. 9E is a bar graph showing concentration of IL-2 secreted by purified CD4+ T cells (C57BL/6, 1.0·10⁵ cells/well, 96 well plate) were stimulated with anti-CD28 and anti-CD3 antibodies, and incubated with PUDCA NPs for 3 d to measure IL-2.
FIG. 9F is a bar graph showing concentration of IL-2 secreted by BMDCs. Bone-marrow derived dendritic cells (BMDCs) (2.5·10⁴) were pretreated with PUDCA NPs for 24 h, washed, and then stimulated with LPS (10 ng/mL) and ovalbumin (OVA, 20 µg/mL) for 24 h, followed by co-culture with OVA-specific OT-II CD4+ T cells (50·10³) for 3 d, followed by quantification of IL-2 by ELISA (FIGS. 9G, 9H, and 9I). BMDCs (1.0·10⁵ cells per well) were stimulated using LPS and OVA for 24 h. Cells were then washed and treated with PUDCA for 3 d, then BMDCs were stained for surface markers (MHC Class II, CD86, and CD40) for flow cytometry. IL-2 production and DC surface marker expression were not affected by treatment with PUDCA NPs.

To determine if this substantial and lengthy retention of PUDCA NPs in diabetic mice could enhance their insulin levels, insulin levels were analyzed in pancreata and serum at several time points after oral gavage of insulin-loaded NPs. While PLGA-treated groups exhibited modest insulin increases, PUDCA delivery of insulin resulted in significantly greater amounts of insulin in both the pancreata (FIG. 8A) and blood (FIG. 8B). This efficient insulin delivery enabled stable blood glucose levels in the nondiabetic range for several weeks, while soluble insulin and PLGA-encapsulated insulin showed no therapeutic benefit (FIG. 8B). Disease remediation was corroborated by the stabilization of body weight of Ins-PUDCA-treated mice, in contrast to declining body weights of other treatment groups (FIG. 8D). Survival of diabetic mice further confirmed the utility of orally delivering insulin using PUDCA NPs; only PUDCA NPs led to survival of up to 90 days after beginning treatment, over twice the survival time of other groups (FIG. 8E). As expected, the number of activated CD8+ T cells was downregulated (FIG. 9A), and depletion of CD4+CD25+ FoxP3+ Tregs was suppressed (FIG. 9B) in the pancreatic lymph nodes when diabetic mice received Ins-PUDCA.

Figure 9C:
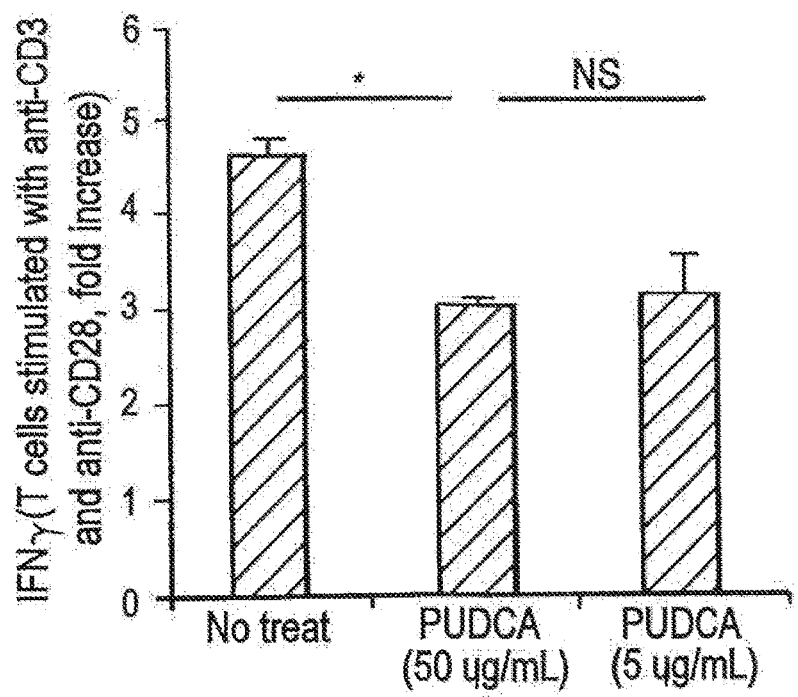
Figure 9D:
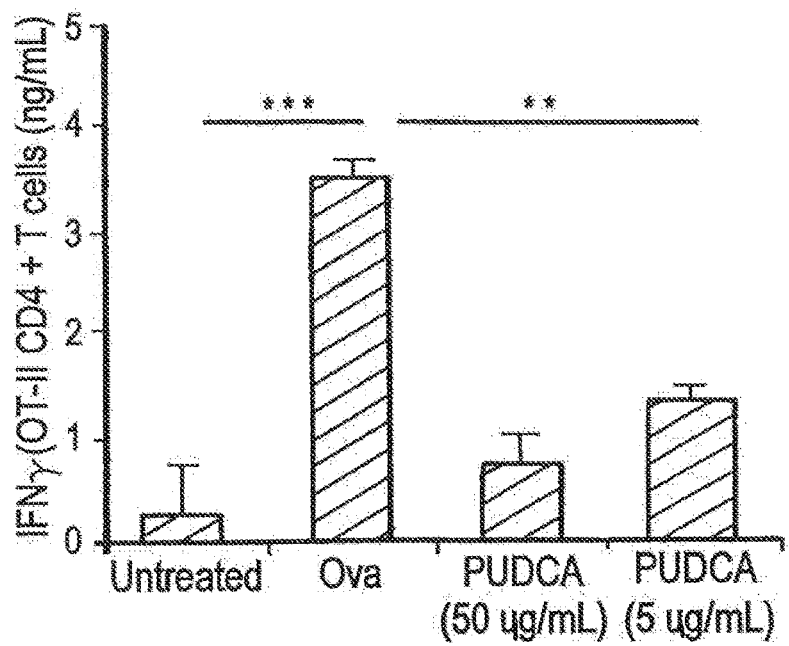
Figure 9E:
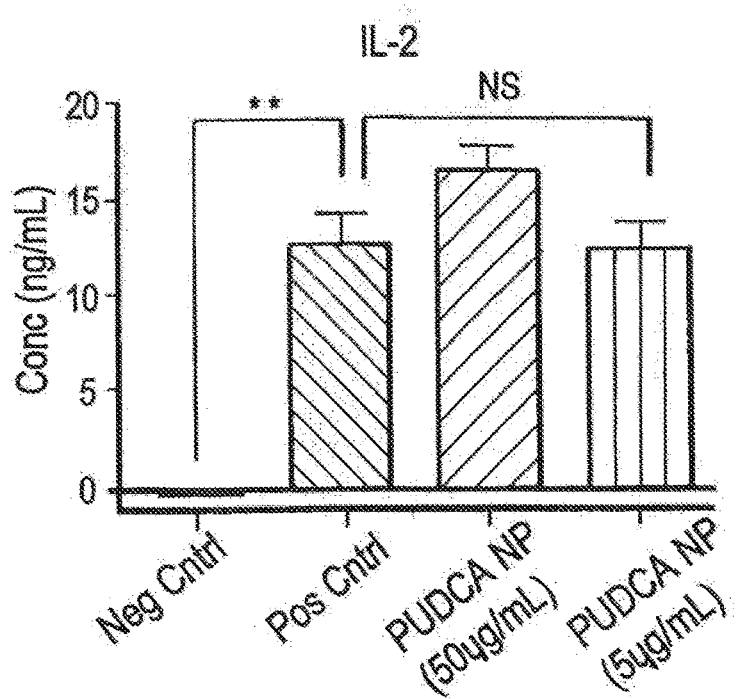
Figure 9F:
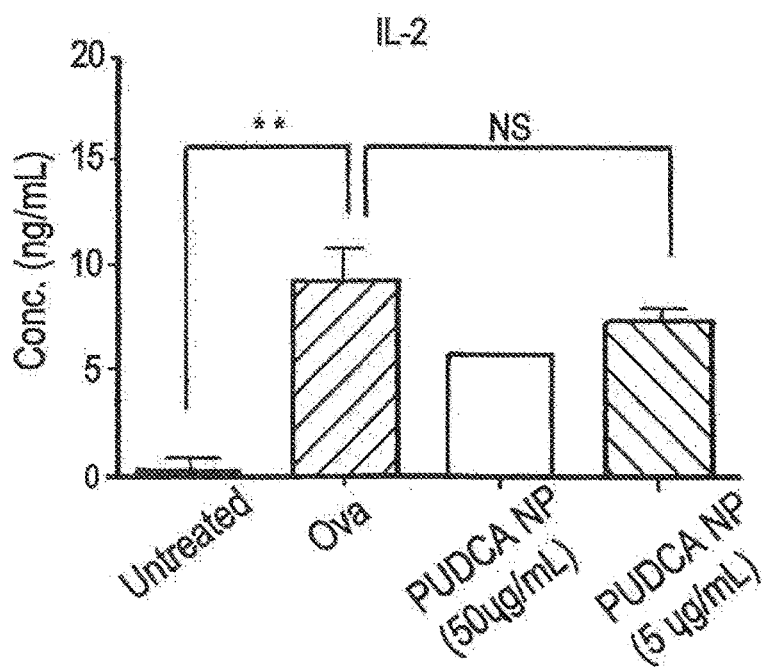
Figure 9G:
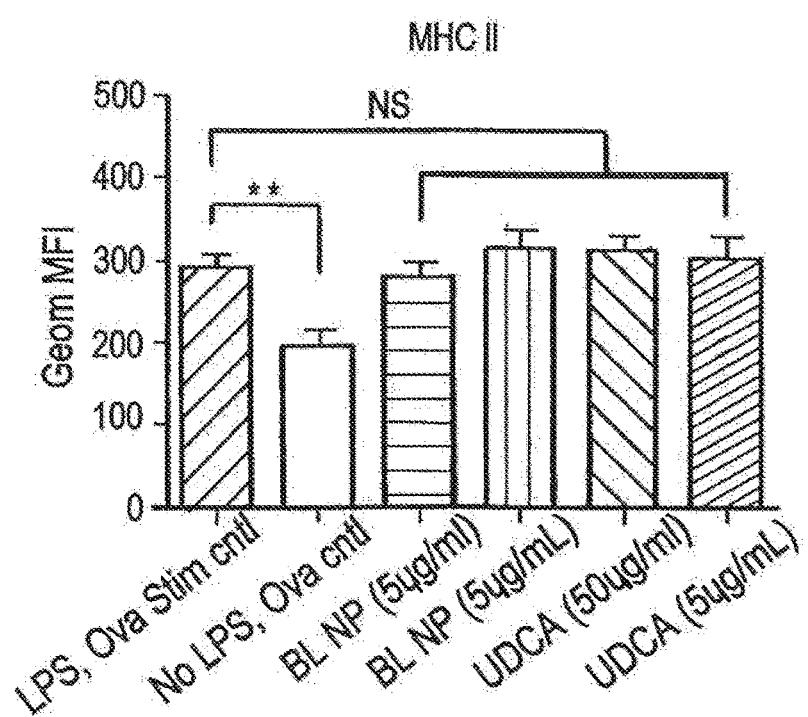
Figure 9H:
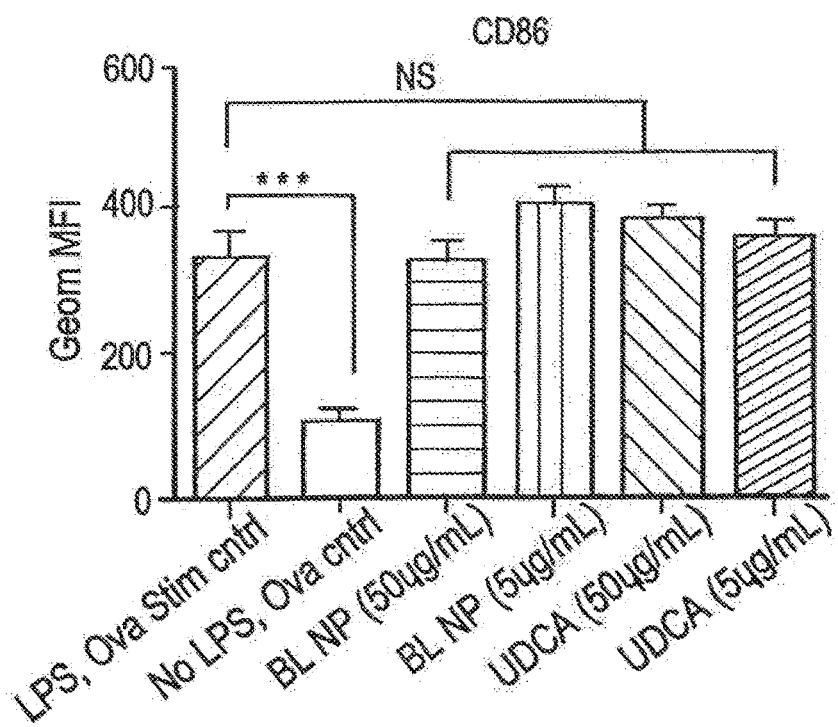
Figure 9I:
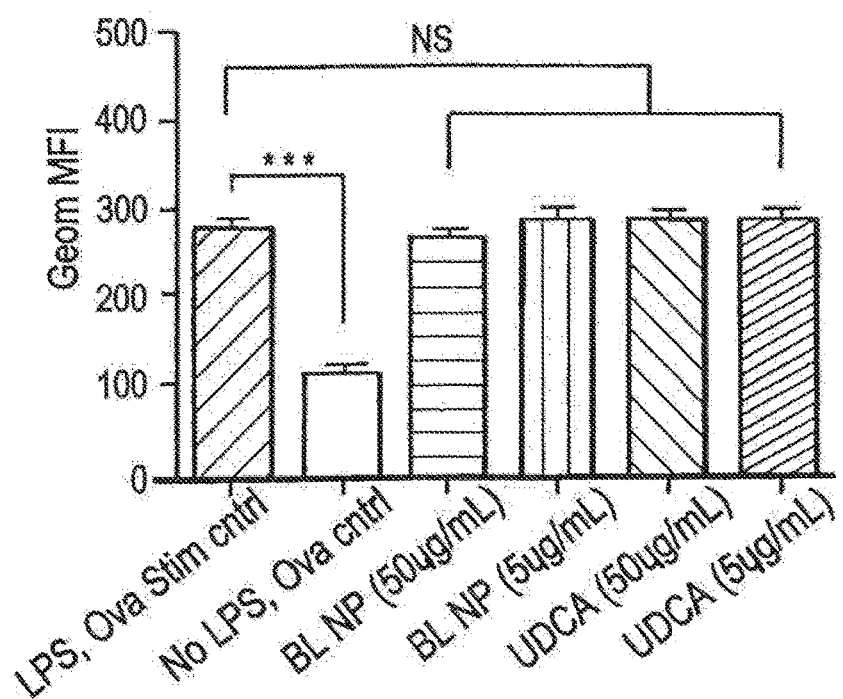

The mitigation of T1D disease progression (FIG. 8C) by treatment of empty (blank) PUDCA NPs suggested that these particles might confer an immunosuppressive effect on the pancreatic microenvironment, perhaps synergizing with encapsulated insulin. The cellular responses of CD4+ T cells and bone marrow-derived dendritic cells (BMDCs) to PUDCA NP treatment in vitro were investigated. Pretreatment of CD4+ T cells with both high (50 μg/mL) and low (5 μg/mL) doses of PUDCA NPs resulted in lower overall IFN-γ production when cells were non-specifically stimulated using anti-CD3 and anti-CD28 antibodies (FIG. 9C). Similarly, antigen-specific OT-II CD4+ cells produced lower IFN-γ when DCs and T cells were co-cultured following pre-treatment of DCs with LPS and antigen ovalbumin (FIG. 9D). In both cases, IL-2 production was unchanged regardless of treatment with PUDCA (FIGS. 9E and 9F). Furthermore, monoculture of BMDCs in the presence of PUDCA following LPS and ovalbumin stimulation did not result in phenotypic changes to DC surface marker expression (FIGS. 9G, 9H, and 9I). These results show that PUDCA may suppress CD4+ effector activity of T cells while leaving DC activation intact.

Taken together, these results demonstrate that PUDCA NPs are a promising platform for both prevention and treatment of T1D. The data in FIGS. 8A-9I show that oral administration of insulin-loaded PUDCA nanoparticles reverses type 1 diabetes in NOD mice.

Example 9. PBA Nanoparticles Target Inflamed Intestines in Inflammatory Bowel Disease Materials and Methods Colitis was induced in balb/c mice by feeding water medicated with dextran sulfate sodium (DSS) (10 mg/mL) for 2 weeks. IBD mice receiving DiR-loaded PLGA nanoparticles after 3 and 24 hour following oral administration (gavage) of 250 uL of 4 mg/ml solution suspended in buffered saline pH 7.4 (50 mg/Kg).

Results

Figure 10A:
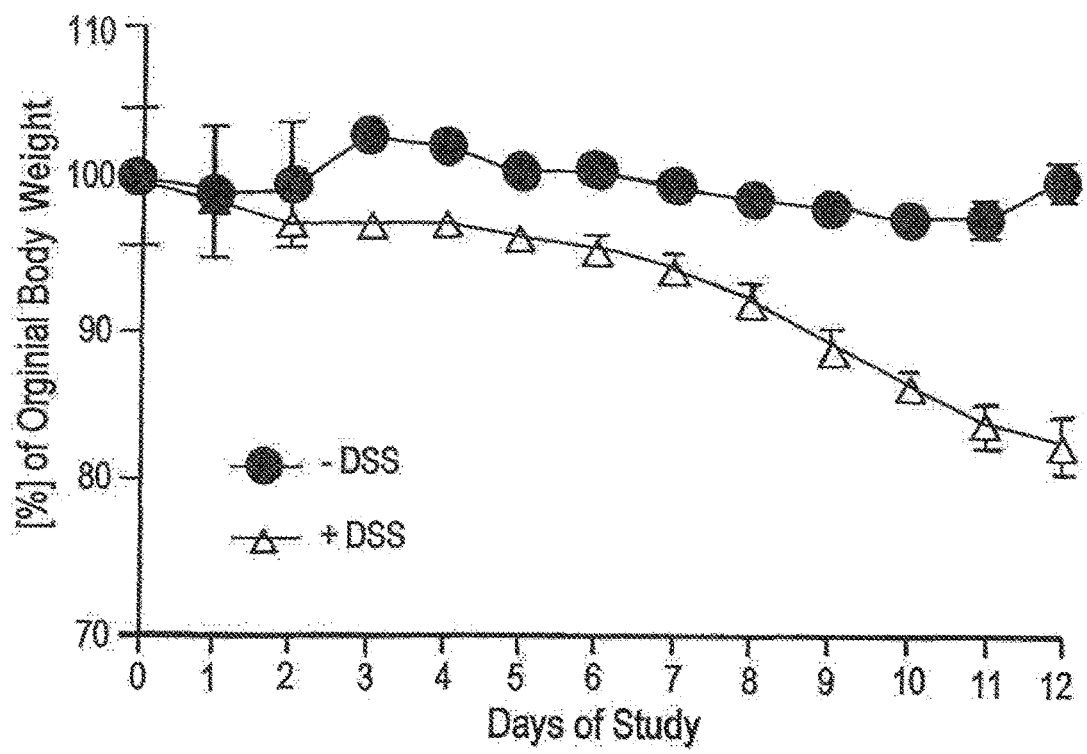
FIG. 10A is a line graph showing a change in the percentage of original body weight as a function of time (days) in wild type mice and in mice with dextran sulfate sodium (DSS)-induced colitis.

Mice with DSS-induced colitis serve as models of inflammatory bowel disease (IBD). In these models, there is progressive loss of body weight over time, if the condition is left untreated (FIG. 10A).

Figure 10B:
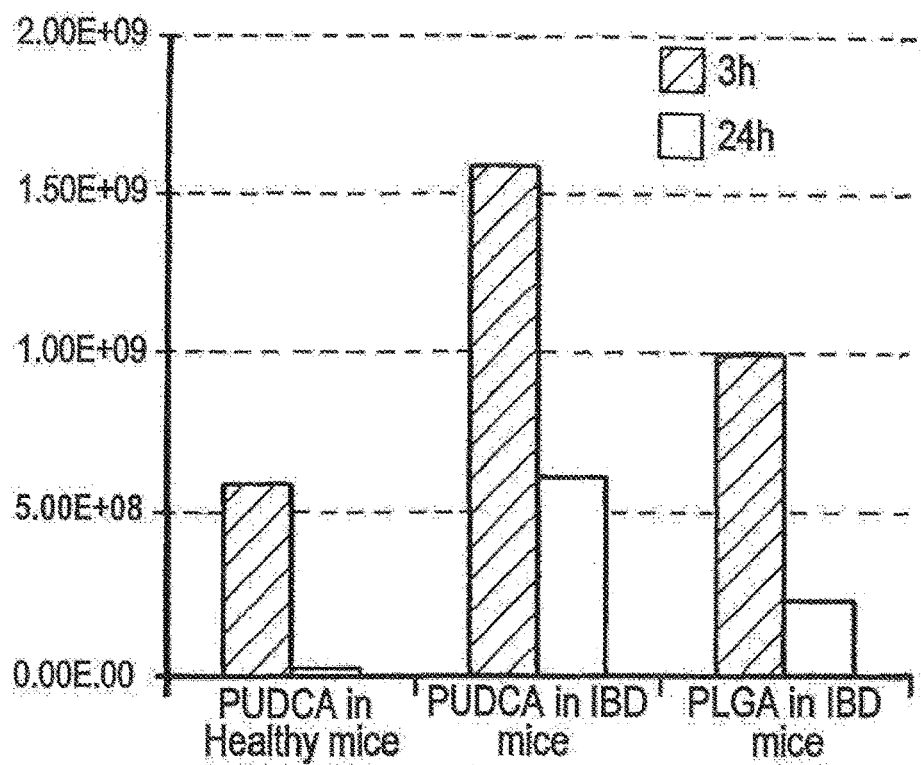
FIG. 10B is a bar graph showing the fluorescence intensity of the gastrointestinal track of healthy mice receiving DiR-loaded PUDCA nanoparticles, IBD mice receiving DiR-loaded PUDCA nanoparticles, or IBD mice receiving DiR-loaded PLGA nanoparticles after 3 and 24 hour following oral administration (gavage) of 250 µL of 4 mg/ml solution suspended in buffered saline pH 7.4. (Jungseok, Please confirm).

The inflammation in the intestines of IBD mice could be targeted with the PBA nanoparticles. As shown in FIG. 10B, oral gavage of 250 μl of 4 mg/ml PUDCA or PLGA nanoparticles in healthy or IBD mice shows that significantly greater amount of PUDCA nanoparticles than of PLGA nanoparticles is retained in the inflamed intestines of IBD mice at 3 and 24 hours following oral gavage. Therefore, the PUDCA nanoparticles could target the inflamed intestines of the mouse model of IBD with greater efficiency, and are retained there longer (compare the fluorescence intensity at 24 hours) than the PLGA nanoparticles. (PLGA: $2.26 \times 10^8$, PUDCA: $6.20 \times 10^8$, n=3, p<0.01)

This work represents a modular, versatile NP platform for efficient oral delivery of a variety of molecules, as poly(bile acid) (PBA) NPs have the ability to encapsulate hydrophobic or amphiphilic small molecule drugs in addition to proteins like insulin. These biologically-inspired NPs accumulated in inflamed pancreata by means of stomach protection, enhanced intestinal permeability, and macrophage carriage. Additionally, therapeutic efficacy of NPs formed with PBA polymers may arise from synergy between this GI protection and pancreatic trafficking, as well as by triggering anti-inflammatory signaling processes.

In conclusion, the demonstrated rationally designed PBA NPs survive the GI tract, accumulate in the pancreas, and prevent and treat T1D. This platform technology may be leveraged for several other pancreatic diseases with growing incidence and grim outcomes, including pancreatitis and pancreatic cancer, which has an extremely high mortality rate.

We claim:

1. A formulation of nanoparticles comprising a polymeric matrix formed of polymers consisting of esterified bile acid monomers (PBA polymers), wherein the bile acid monomers have a structure of Formula I,

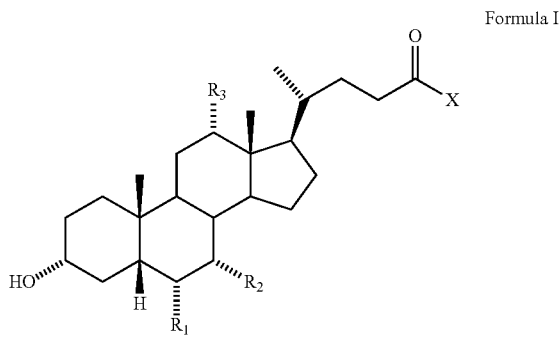

Formula I wherein $R_1$, $R_2$, and $R_3$ are independently hydrogen or —OH, and X is —OH or —O⁻, or are selected from the group of taurine or glycine conjugates thereof consisting of glycocholic acid, taurocholic acid, glycodeoxycholic acid, taurodeoxycholic acid, taurolitholic acid, taurochenodeoxycholic acid, tauroursodeoxycholic acid, glycolithocholic acid, glycochenodeoxycholic acid; or taurine conjugates of 3-alpha-7-alpha-12-alpha-22-xi-tetrahydroxy-5-beta-cholestan-26-oic acid or taurine conjugates of 3-alpha-12-alpha-22 xitrihydroxy-5-beta-cholestan-26-oic acid, wherein the PBA polymers have a molecular weight between 500 Da and 250,000 Da, wherein the nanoparticles comprise one or more therapeutic, prophylactic or diagnostic agents encapsulated within or entrapped in to the PBA polymers.

2. The formulation of claim 1, wherein the nanoparticles are formed by emulsifying the PBA polymers.

3. The formulation of claim 1 selectively taken up by the pancreas, liver, or colon after oral administration.

4. The formulation of claim 1, wherein the nanoparticles further comprise one or more targeting moieties to specific cell types.

5. The formulation of claim 1, wherein the agent is selected from the group consisting of proteins and peptides, sugars and polysaccharides, nucleic acids, lipids, small molecules having a molecular weight of less than 2000 Daltons, and combinations thereof.

6. The formulation of claim 5, wherein the agent is selected from the group consisting of antigens, cytokines, hormones, anti-infectives, anti-proliferatives, anti-inflammatory agents, and immunomodulatory agents.

7. The formulation of claim 1 for inducing tolerance, wherein the agent is a tolerogenic antigen selected from the group consisting of allergen, self-protein, and autoimmune antigen; a tolerogenic agent selected from the group consisting of TGF-beta, rapamycin and analogs thereof, retinoic acid, TLR agonists, cyclosporin, methotrexate, steroids, azathioprine, and tacrolimus; or a combination of the tolerogenic antigen and the tolerogenic agent.

8. The formulation of claim 1, wherein the agent is insulin.

9. The formulation of claim 1, wherein the agent is an anti-proliferative or chemotherapeutic agent for treatment of cancer.

10. The formulation of claim 1 for non-invasively imaging pancreatic, liver, or colon inflammation in a subject in need thereof, wherein the agent is an imaging agent.

11. The formulation of claim 10, wherein the nanoparticles comprise one or more imaging agent(s) selected from the group consisting of superparamagnetic iron oxide (SPIO), gadolinium, europium, diethylene triamine pentacetic acid (DTPA), 1,4,7,10-tetraazacyclododecane-1,4,7,10-tetraacetic acid (DOTA), gas, and positron-emitting radionuclides.

12. The formulation of claim 1 in a liquid dosage form.

13. A method of delivering a therapeutic, prophylactic or diagnostic agent, comprising orally administering to a subject in need thereof an effective amount of the formulation of claim 1.

14. The method of claim 13 for treatment of type 1 or type 2 diabetes, wherein the agent in the formulation is insulin.

15. The method of claim 13 for inducing tolerance, wherein the agent in the formulation comprises a tolerogenic antigen selected from the group consisting of allergen, self-protein, and autoimmune antigen; a tolerogenic agent selected from the group consisting of TGF-beta, rapamycin and analogs thereof, retinoic acid, TLR agonists, cyclosporin, methotrexate, steroids, azathioprine, and tacrolimus; or a combination of the tolerogenic antigen and the tolerogenic agent.

16. The method of claim 13, wherein the agent in the formulation is selected from the group consisting of anti-inflammatory agents, anti-proliferatives and anti-infectives, wherein the subject has pancreatitis, colitis, or a proliferative disorder.

17. A method of making the formulation of claim 1 comprising mixing the agent with the PBA polymers and forming the PBA polymers into nanoparticles.

18. The method of claim 17 wherein the PBA polymers are in a solution.

19. The method of claim 17 wherein the agent is added to the PBA polymers in powder or aggregated form.

20. The formulation of claim 1 in a dosage form for oral administration to an individual in need thereof.

21. The formulation of claim 20 wherein the dosage form is a tablet, capsule or powder.

22. The formulation of claim 1 wherein the dosage form is a solution for nasal, pulmonary, rectal or vaginal administration.

23. The formulation of claim 7, wherein the analogs of rapamycin are selected from the group consisting of everolimus, ridaforolimus, remsirolimus, umirolimus, and zotarolimus.

24. The formulation of claim 1, wherein the PBA polymers have a structure of Formula VII,

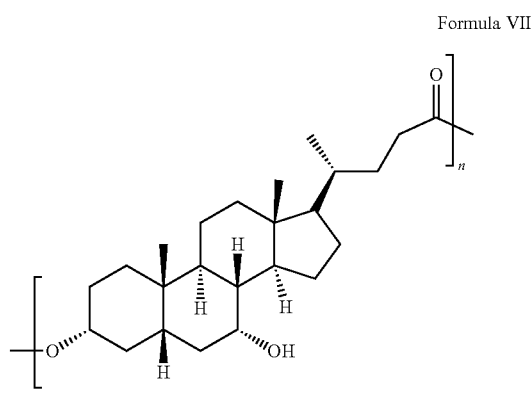

Formula VII wherein n is a number ranging from between 2-600.

25. The formulation of claim 1, wherein the bile acid monomers are selected from the group consisting of cholic acid (CA), lithocholic acid (LCA), deoxycholic acid (DCA), cheno-deoxycholic acid (CDCA), and urso-deoxycholic acid (UDCA), and combinations thereof.

* * * * *